US008318951B2

(12) United States Patent
Olson et al.

(10) Patent No.: US 8,318,951 B2
(45) Date of Patent: Nov. 27, 2012

(54) STEM CELL DIFFERENTIATING AGENTS AND USES THEREFOR

(75) Inventors: Eric N. Olson, Dallas, TX (US);
Douglas Frantz, Boerne, TX (US);
Jenny Hsieh, Irving, TX (US); Steven L. McKnight, Dallas, TX (US); Jay Schneider, Coppell, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/116,574

(22) Filed: May 26, 2011

(65) Prior Publication Data
US 2012/0029200 A1  Feb. 2, 2012

Related U.S. Application Data

(60) Division of application No. 12/183,884, filed on Jul. 31, 2008, now Pat. No. 7,981,935, and a continuation-in-part of application No. 11/974,479, filed on Oct. 12, 2007, now Pat. No. 8,193,225.

(60) Provisional application No. 60/953,182, filed on Jul. 31, 2007.

(51) Int. Cl.
| C07D 405/14 | (2006.01) |
| C07D 413/04 | (2006.01) |
| A61K 31/4155 | (2006.01) |
| A61K 31/422 | (2006.01) |
| A61P 29/00 | (2006.01) |
| C12N 5/0775 | (2010.01) |
| C12N 5/0797 | (2010.01) |

(52) U.S. Cl. ............ 548/365.7; 514/378; 514/406; 548/248

(58) Field of Classification Search ............ None
See application file for complete search history.

(56) References Cited

U.S. PATENT DOCUMENTS
5,201,932 A  4/1993  Maywald et al. .......... 504/271

FOREIGN PATENT DOCUMENTS
| EP | 0 418 667 | 3/1991 |
| JP | 08-027130 | * 1/1996 |
| WO | WO 03/013517 | 2/2003 |
| WO | WO 2009/006267 | 1/2009 |

OTHER PUBLICATIONS

Machine Translation of JP 08-027130, Jan. 30, 1996.*
Registry No. 921177-00-6, entered into Registry file on STN on Feb. 15, 2007.*
Registry No. 857283-79-5, entered into Registry file on STN on Jul. 27, 2005.*
Registry No. 922343-19-9, entered into Registry file on STN on Feb. 22, 2007.*

Chandrasekhar et al., "Direct conversion of tosylhydrazones to tert-butyl ethers under bamford-stevens reaction conditions," *Synlett.*, 1779-1780, 2001.
Chi et al., Production of green fluorescent protein transgenic embryonic stem cells using the GENSAT bacterial artificial chromosome library, *PNAS*, 102:13490-13495, 2005.
Creemers et al., "Myocardin is a direct transcriptional target of Mef2, Tead and Foxo proteins during cardiovascular development," *Development*, 133:4245-4256, 2006.
Database Chemcats Chemical Abstract Service, XP002509165 retrieved from STN order numbers: AKL-P-1661072, AKL-P-1660956, AKL-P-1661210, AKL-P-1413044, AKL-P-1660951, AKL-P-1753501, Feb. 7, 2006.
Elliot et al., "A tyrosine-rich domain within homeodomain transcription factor Nkx2-5 is an essential element in the early cardiac transcriptional regulatory machinery," *Development*, 133:1311-22, 2006.
Hidaka et al., "Chamber-specific differentiation of Nkx2.5-positive cardiac precursor cells from murine embryonic stem cells," *The FASEB Journal*, published online Feb. 19, 2003.
Hsieh et al., "Histone deacetylase inhibition-mediated neuronal differentiation of multipotent adult neural progenitor cells," *Proc. Natl. Acad. Sci. USA*, 101:16659-16664, 2004.
Hsieh et al., "IGF-I instructs multipotent adult neural progenitor cells to become oligodendrocytes," *J. Cell Biol.*, 164:111-122, 2004.
Larabi et al., "Synthesis, structural study and electrochemical properties of copper(II) complexes derived from benzene- and p-toluenesulphonylhydrazones," *J. Serb. Chem. Soc.*, 68:85-95, 2003.
Leopoldo et al., "Design, synthesis, and binding affinities of potential positron emission tomography (PET) ligands for visualization of brain dopamine D-3 receptors," *J. Med. Chem.*, 49:358-365, 2006.
Morissette et al., "High-throughput crystallization: polymorphs, salts, co-crystals and solvates of pharmaceutical solids," *Advanced Drug Delivery Reviews*, 56:275-300, 2004.
Munshi et al., "Synthesis of aryl sulphonyl hydrazones and I-aryl sulphonyl 4-substituted thiosemicarbzaides," *Indian J. Chem.*, 1:311-313, 1963.
Office Action issued in U.S. Appl. No. 11/974,479, mail date May 1, 2009.
Office Action issued in U.S. Appl. No. 11/974,479, mail date Dec. 17, 2009.
Office Action issued in U.S. Appl. No. 11/974,479, mailed Sep. 1, 2010.
Office Action issued in U.S. Appl. No. 12/183,884, mailed Jan. 10, 2011.
Office Action issued in U.S. Appl. No. 12/183,884, mailed Sep. 3, 2010.
Özmen et al., "Synthesis, characterization and antibacterial activity of new sulfonyl hydrazone derivatives and their nickel(II) complexes," *Spectrochimica Acta Part A*, 70:641-645, 2008.
PCT International Preliminary Report on Patentability issued in International Application No. PCT/US2007/081304, mailed Apr. 23, 2009.

(Continued)

*Primary Examiner* — Fiona T Powers
(74) *Attorney, Agent, or Firm* — Parker Highlander PLLC

(57) ABSTRACT

The present invention relates to screens for compounds that can induce stem cell differentiation. In addition, isoxazoles and sulfonyl hydrazones are identified as general classes of compounds that can induce differentiation of stem cells into cells of neuronal and cardiac fate, respectively.

3 Claims, 23 Drawing Sheets

OTHER PUBLICATIONS

PCT International Preliminary Report on Patentability issued in International Application No. PCT/US2008/071843, mailed Feb. 11, 2010.

PCT International Search Report and Written Opinion issued in International Application No. PCT/US2007/081304, mailed Oct. 7, 2008.

PCT International Search Report and Written Opinion issued in International Application No. PCT/US2008/071843, mailed Apr. 28, 2009.

PCT Invitation to Pay Additional Fees issued in International Application No. PCT/US2008/071843, dated Jan. 26, 2009.

PCT Invitation to Pay Additional Fees issued in International Application No. PCT/US2007/081304, mailed Jul. 8, 2008.

Pipes et al., "The myocardin family of transcriptional coactivators: versatile regulators of cell growth, migration, and myogenesis," *Genes and Develop.*, 20:1545-1556, 2006.

Rawat et al., "Study of photochomism in benzenesulfonylhydrazones," *Chemical Abstracts*, 110:74706, 1989.

Response to Office Action issued in U.S. Appl. No. 11/974,479, submitted Oct. 1, 2009.

Response to Office Action issued in U.S. Appl. No. 11/974,479, submitted Jun. 17, 2010.

Response to Office Action issued in U.S. Appl. No. 11/974,479, submitted Sep. 8, 2010.

Response to Office Action issued in U.S. Appl. No. 12/183,884, submitted Apr. 13, 2011.

Response to Office Action issued in U.S. Appl. No. 12/183,884, submitted Feb. 9, 2011.

Response to Office Action issued in U.S. Appl. No. 12/183,884, submitted Dec. 3, 2010.

Sasaki et al., "Novel generation and cycloaddition reactivity of n-phenylsulfonylbenzonitrilimine via thermal decomposition of n-(phenylsulfonyl)benzohydrazonoyl chloride," *Tetrahedrom*, 36:1565-1569, 1980.

Schneider and Olson, "Small molecules and the pharmacology of cardiac cell fate," Circulation Research 99 (5): pE37, Conference/meeting—3rd Annual Symposium of the American-Heart-Association-Council-on-Basic-Cardiovascular-Sciences, Keystone, CO, USA, Jul. 31-Aug. 3, 2006.

Shyam et al., "Antitumor 2-(Aminocarbonyl)-1,2-bis(methylsulfonyl)-1-(2-chloroethyl)- hydrazines," *J. Med. Chem.*, 39:796-801, 1996.

Siemann et al., "N-arylsulfonyl hydrazones as inhibitors of Imp-1 metallo-β-lactamase," *Antimicrobial Agents and Chemotherapy*, 46:2450-2457, 2002.

Souillac and Rytting, "Characterization of delivery systems, differential scanning calorimetry," *In:* Encyclopedia of Controlled Drug Delivery, John Wiley and Sons, pp. 212-227, 1999.

Suk Kim et al., "Expression of ErbB receptors in ES cell-derived cardiomyocytes," *Biochem. Biophys. Res. Commun.*, 309:241-6, 2003.

Takahashi et al., "Ascorbic acid enhances differentiation of embryonic stem cells into cardiac myocytes," *Circulation*, 107:1912-1916, 2003.

Tomishima et al., "Production of green fluorescent protein transgenic embryonic stem cells using the GENSAT bacterial artificial chromosome library," *Stem Cells.*, 25:39-45, 2007.

Vippagunta et al., "Crystalline solids," *Advanced Drug Delivery Reviews*, 48:3-26, 2001.

Yamashita et al., "Prospective identification of cardiac progenitors by a novel single cell-based cardiomyocyte induction," *FASEB J.*, 19:1534-1536, 2005.

* cited by examiner

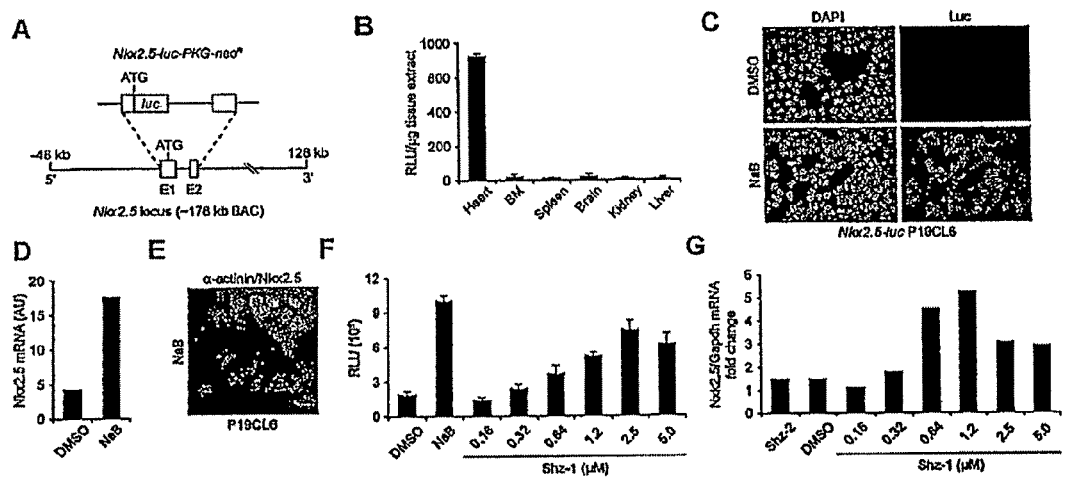
FIG. 1A-G

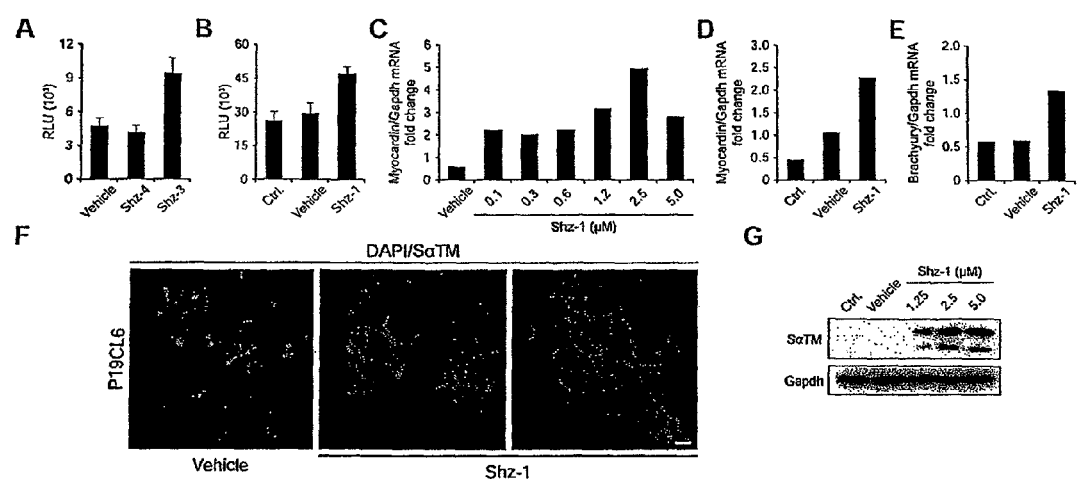
FIG. 2A-G

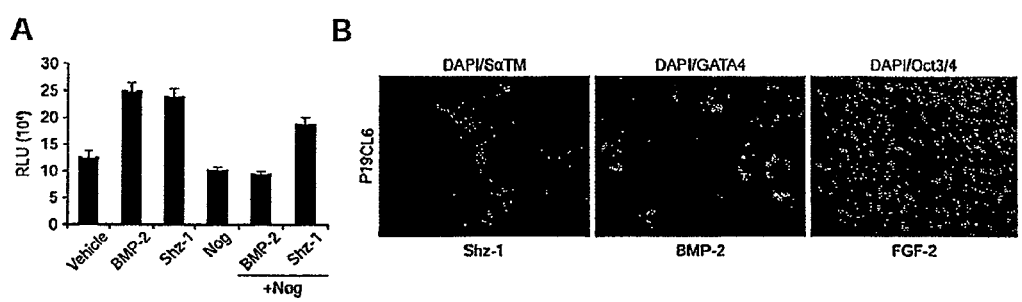
FIG. 3A-B

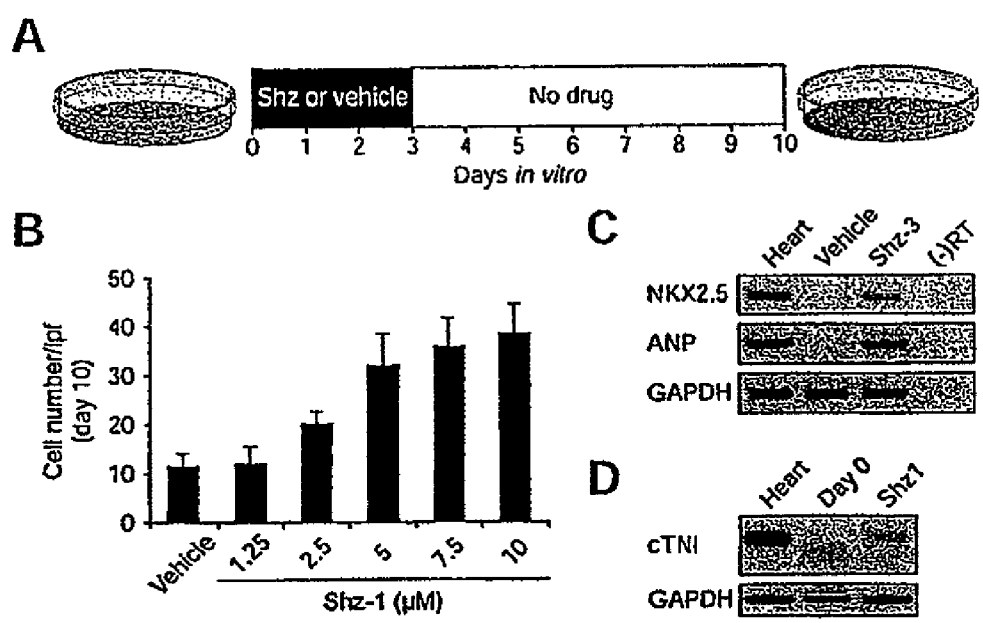
FIG. 4A-D

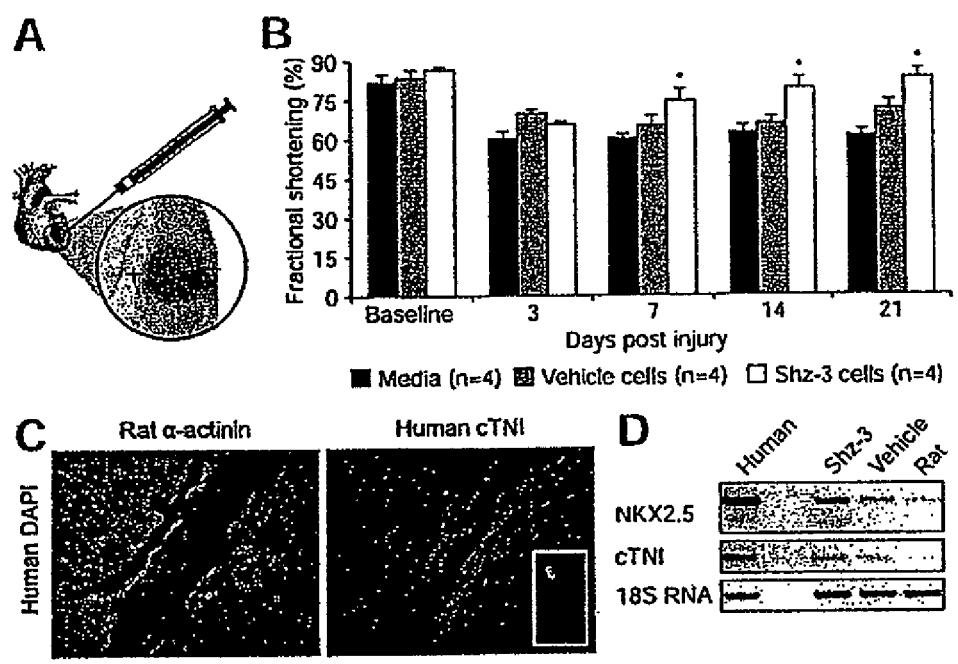
FIG. 5A-D

FIG. 10A-B

Sulfonyl-hydrazones from primary screen:
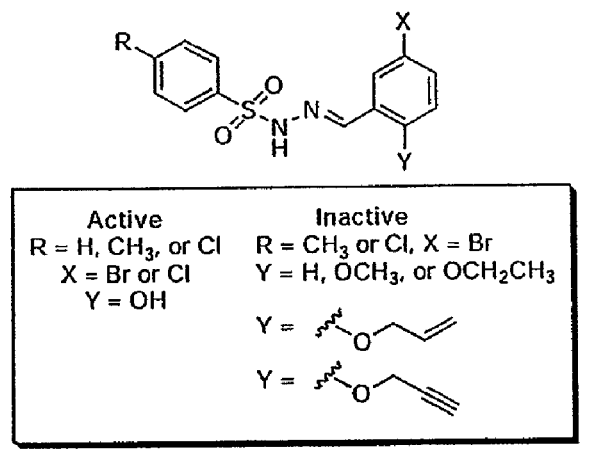
Re-synthesis of sulfonyl-hydrazones:
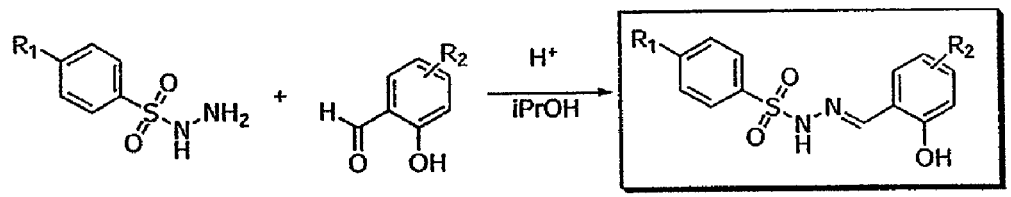
FIG. 11

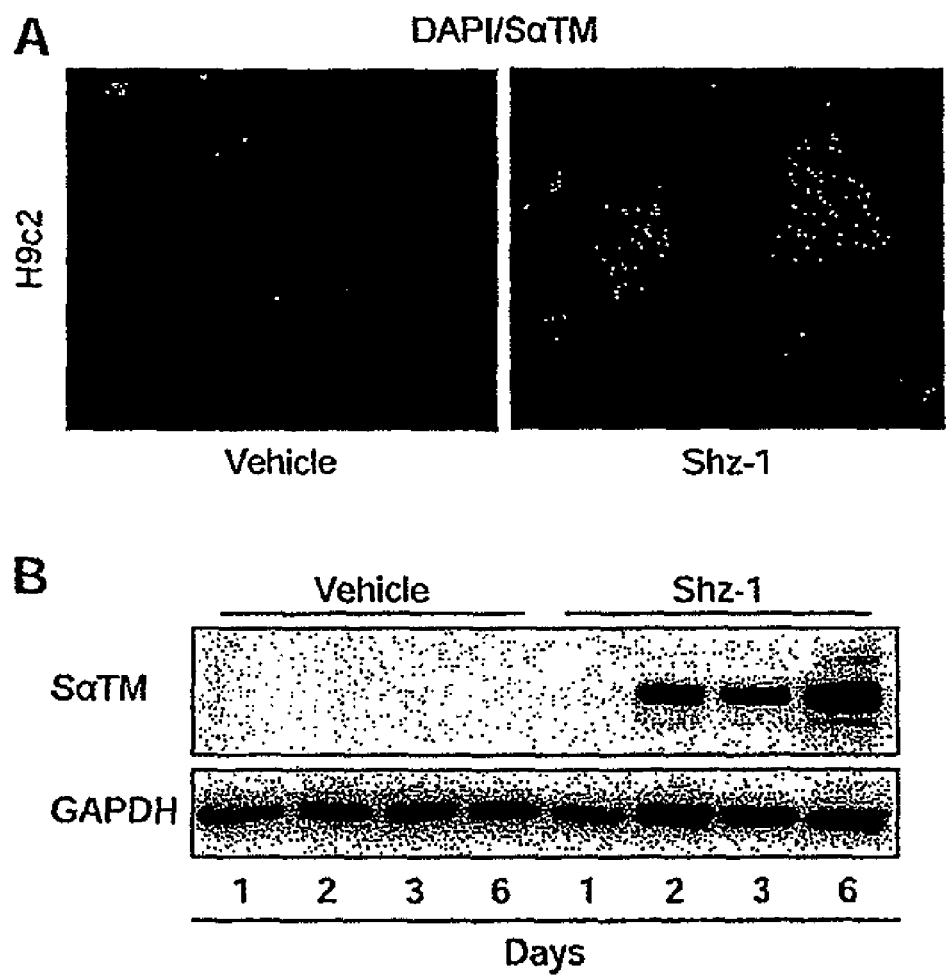
FIG. 12A-B

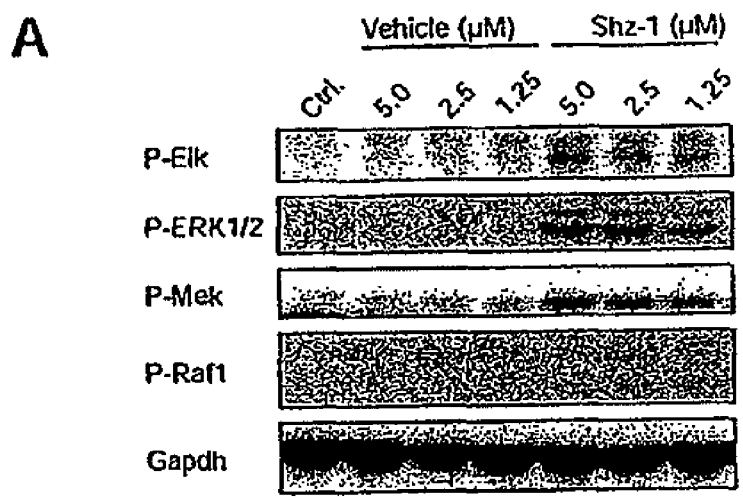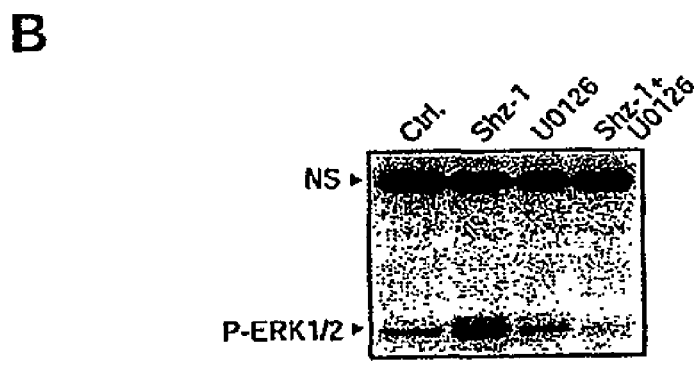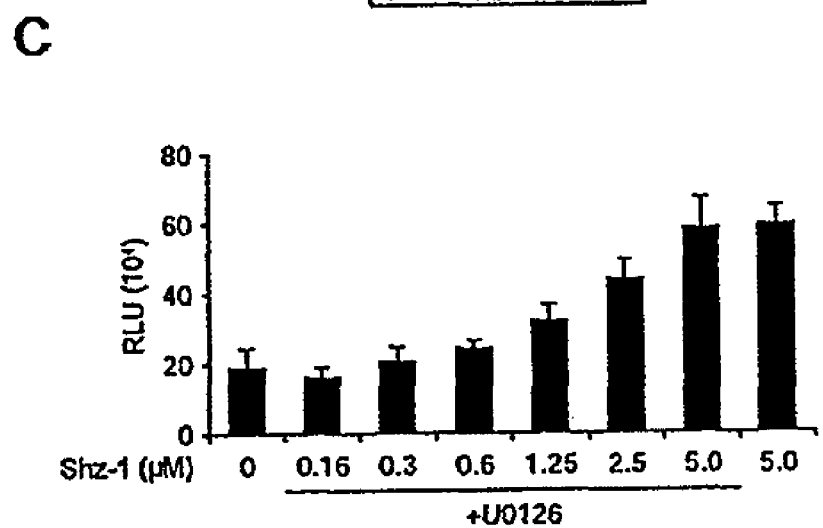
FIG. 13A-C

Fig. 14A
Isx reduce anchorage-independent growth
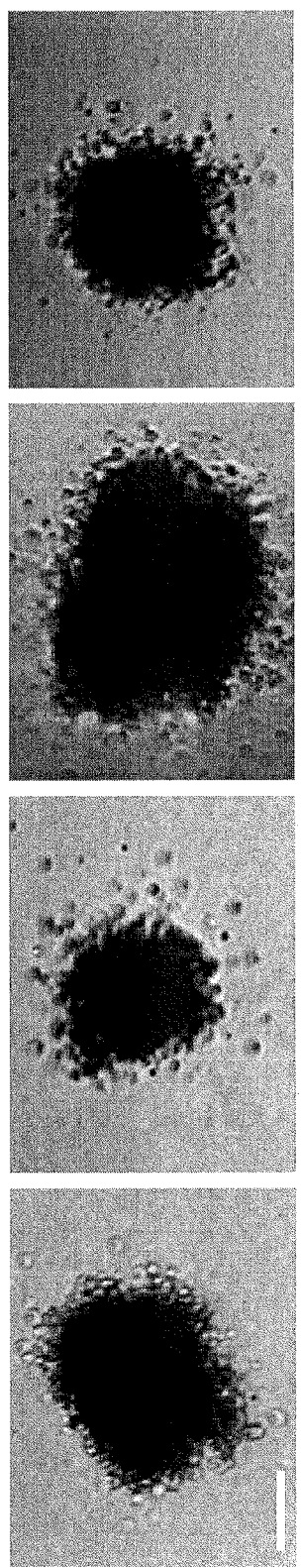
Vehicle
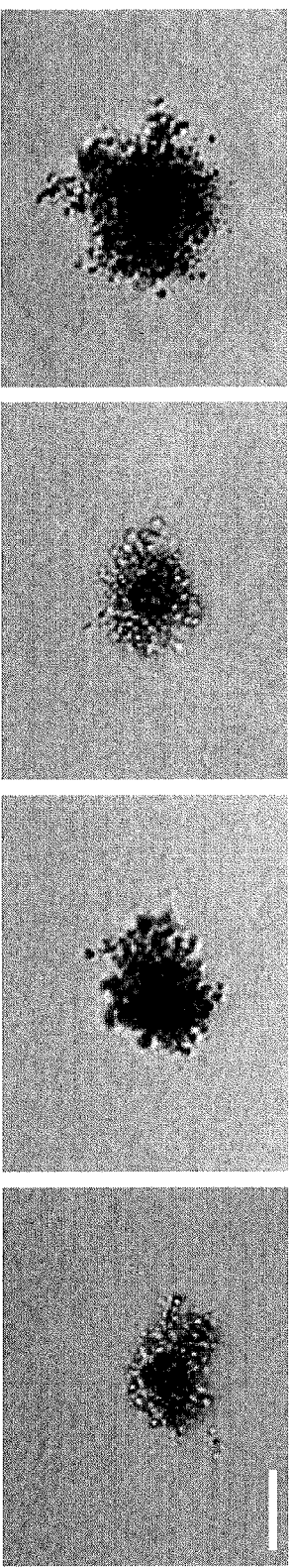
50 µM isoxazole-10
U87MG 4 weeks Fig. 14D
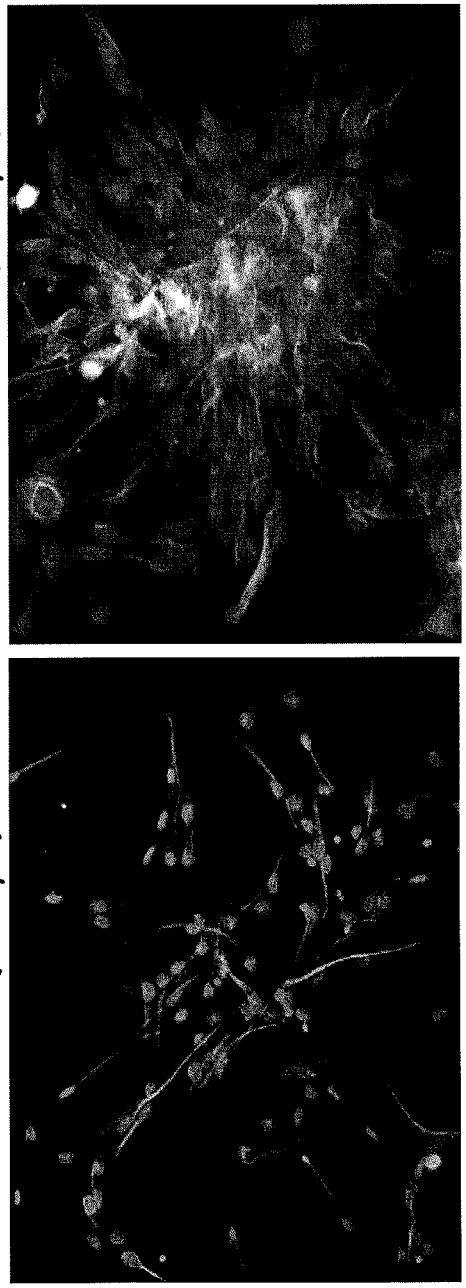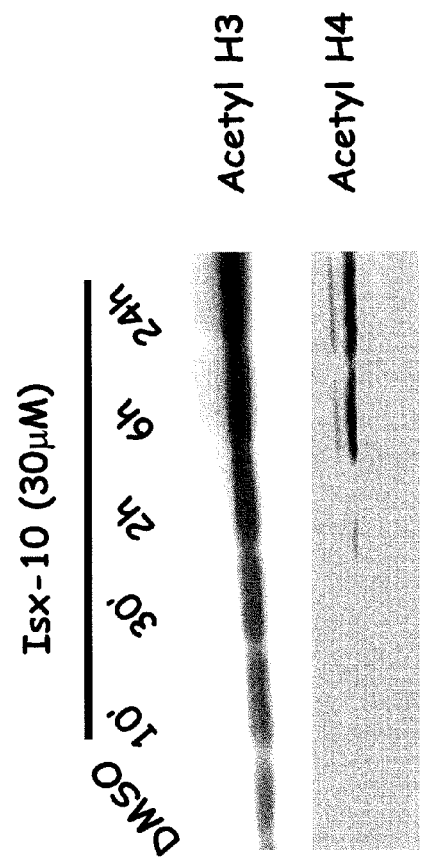

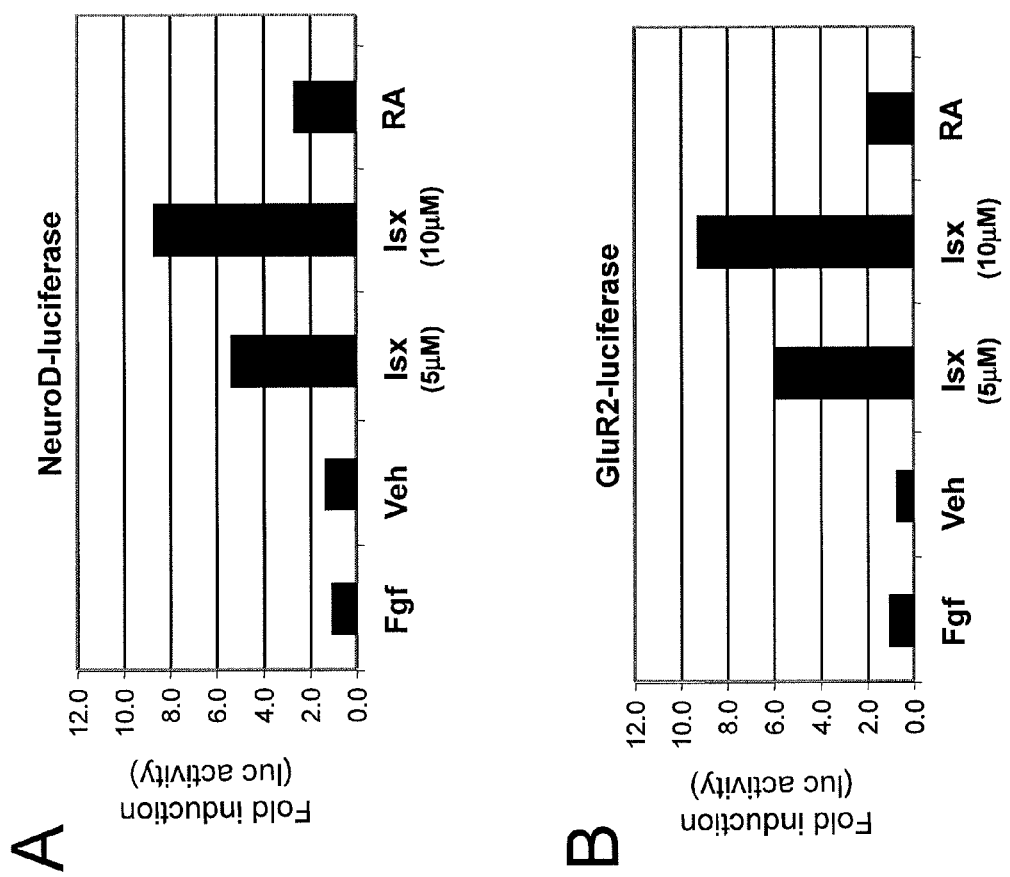
Fig. 15A-B

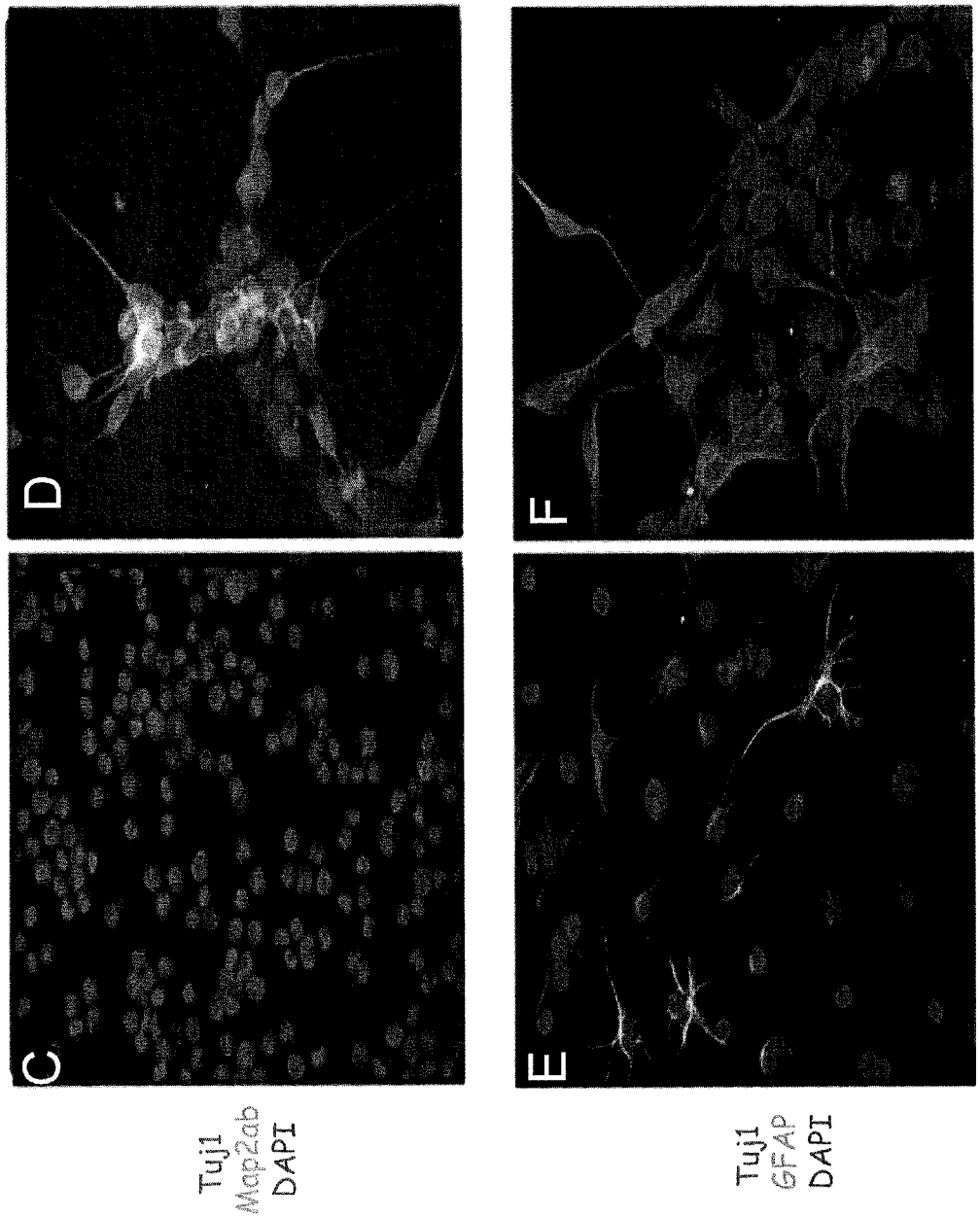
Fig. 15C-F

SEQUENCE LISTING

<160> NUMBER OF SEQ ID NOS: 1

<210> SEQ ID NO 1
<211> LENGTH: 12
<212> TYPE: DNA
<213> ORGANISM: Artificial
<220> FEATURE:
<223> OTHER INFORMATION: Synthetic primer

<400> SEQUENCE: 1
ttatttattt ag                                                        12

STEM CELL DIFFERENTIATING AGENTS AND USES THEREFOR

The present application is a divisional application of U.S. Ser. No. 12/183,884, filed on Jul. 31, 2008, now U.S. Pat. No. 7,981,935, which claims benefit of U.S. Provisional Application Ser. No. 60/953,182, filed Jul. 31, 2007. The present application is also a continuation-in-part of U.S. Ser. No. 11/974,479, filed Oct. 12, 2007now U.S. Pat. No. 8,193,225. The entire contents of each of these applications are hereby incorporated by reference.

This invention was made with government support under grant nos. AI 20069 and AI 058162 awarded by the National Institutes of Health. The government has certain rights in the invention.

BACKGROUND OF THE INVENTION

I. Field of The Invention

The present invention relates generally to the fields of cell biology, developmental biology, cardiology and neurobiology. More particularly, it concerns methods and compositions relating to the differentiation of stem cells into cardiogenic or neurogenic cell types.

II. Description of Related Art

A. Cardiogenesis

Stem cell therapy and regenerative medicine are promising new frontiers in the treatment of myocardial infarction (MI) and heart failure. Yet, endogenous stem cell repair mechanisms are underpowered for repair of the tissue destruction associated with ischemic and non-ischemic cardiomyopathies. Thus, there is intense interest in developing therapeutic strategies or drugs to enhance the endogenous regenerative potential of the adult human myocardium. Alternatively, cardiogenic stem cell populations can be supplied to the heart exogenously, when and where needed to repair myocardial injury. Pre-delivery enhancement of stem/progenitor cell function by promoting cell growth, differentiation, survival, homing, or a combination of these, using small-molecule drugs or growth factors is an exciting new strategy that has been successful in clinical trials of peripheral vascular disease (Seeger et al., 2005; 2007; Sasaki et al., 2006; Dimmeler et al., 2001; Yamaguchi et al., 2003; Wojakowski et al., 2007). Cytokine mobilized PBMCs are a universally accessible source of autologous human stem/progenitor cells (Wojakowski et al., 2007). Despite the uncertainty regarding the cardiogenic plasticity of bone marrow-derived cells, clinical trials have moved forward at a rapid pace. Initial results from over a dozen worldwide trials using bone marrow-derived cells in MI and heart failure have demonstrated feasibility, safety and modest but definite clinical benefits, generating considerable optimism for the future of this therapy (Rosenzweig, 2006; Assmus et al., 2006; 2007; Schachinger et al., 2006a). Still, many basic scientific questions remain unanswered. To fulfill the clinical promise of stem/progenitor cells in cardiovascular repair, it is essential to clarify the roles of cardiomyogenesis, neovascularization, cell fusion (Nygren et al., 2004) and paracrine growth factor secretion (Dell'Era et al., 2003), since all of these mechanisms could contribute to the recovery of cardiac function (Dimmeler et al., 2005).

An enhanced understanding of cell fate mechanisms will also translate into greater clinical success of cardiovascular cell therapy (Assmus et al., 2006; Schachinger et al., 2006a; 2006b; Nadal-Ginard & Fuster, 2007). Recent studies indicate that cardiac muscle, vascular smooth muscle and endothelial cells share a common multi-potent progenitor heritage, the cardiovascular master stem cell, which has been identified in human myocardium (Wu et al., 2006; Moretti et al., 2006; Garry & Olson, 2006). However, despite decades of intensive investigation using traditional molecular, cellular and genetic experimental approaches, in vertebrate, invertebrate and stem cell models (Garry & Olson, 2006), much remains to be learned about the circuitry that drives cardiovascular fate specification.

Chemical genetics offers a new investigative approach to cardiovascular fate in stem cells (Ding & Schultz, 2004; Chen et al., 2006). High throughput technology allows libraries of hundreds of thousands of synthetic organic chemicals to be rapidly screened, identifying small-molecules that perform specific functions, through highly targeted interactions with proteins. Small-molecules can provide new probes to explore complex signaling networks and pathways. Importantly, bioactive small-molecules identified in chemical screens provide both highly versatile experimental probes to interrogate mechanistic hypotheses and serve as platforms for new drugs.

B. Neurogenesis/Brain Cancer

Unlike the heart, the brain has several repositories of stem/progenitor cells available to participate in repair and regeneration, yet much needs to be learned regarding the ability of these cells to proliferate, differentiate and migrate in response to physiologic and pathophysiologic stimuli within the central nervous system. Hippocampal neurogenesis, a mechanism for maintaining cellular homeostasis in the adult brain, plays an important functional role in higher cerebral activities like learning and memory. While exercise and exposure to an enriched environment promote adult hippocampal neurogenesis, chronic stress, depression, sleep deprivation and aging can decrease neural stem/progenitor cell proliferation in the adult hippocampus. Chemistry has an established role in governing neurogenesis; the stress-related glucocorticoid hormones inhibit, whereas anti-depressant medications enhance hippocampal neurogenesis. The ability to grow and maintain neural stem/progenitor cells in vitro in an undifferentiated, highly proliferative state provide a unique experimental system and opportunity to study chemical triggers of cell fate. Importantly, chemicals can be identified that not only strongly favor neuronal differentiation, but also actively suppress astrocyte and oligodendrocyte differentiation, two alternative fate choices available to these stem cells. Explorations of the chemical biology of adult neurogenesis have important implications for understanding the mechanisms of cell fate and provide new drug candidates to treat neurological conditions that involve neurogenesis.

As a corollary to the ability of a chemical compound to induce neurogenesis in a neural stem/progenitor cell, this sort of compound might also be an effective differentiation-inducing anti-neoplastic agent. Increasing evidence indicates that stem cells lie at the root of brain tumors like glioblastoma multiforme. Small-molecules that are active in neural stem/progenitor cells might therefore also have bioactivity against the brain tumor stem cell. Thus, small-molecules that induce neural stem cell differentiation might also be useful for arresting growth, killing or differentiating glioblastoma multiforme (GBM) cancer stem cells, currently thought to be the cause of one of the most devastating and incurable of human malignancies.

SUMMARY OF THE INVENTION

In accordance with the present invention, there is provided a composition comprising a compound having the formula, or a compound of the formula:

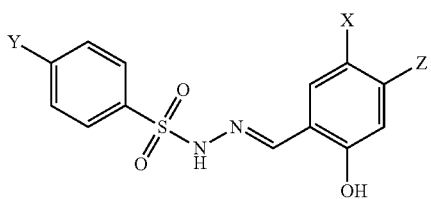

wherein X is H, a substituted or unsubstituted $C_1$-$C_6$ alkyl, $C_2$-$C_6$ alkenyl, $C_2$-$C_6$ alkynyl or an aromatic ring structure, Y is H, a substituted or unsubstituted $C_1$-$C_6$ alkyl, $C_2$-$C_6$ alkenyl, or $C_2$-$C_6$ alkynyl, halogen, a $C_1$-$C_6$ alcohol or a substituted or unsubstituted $C_1$-$C_6$ alkoxy, and Z is H or methyl, with the provisos that X and Y cannot both be H; and if Z is methyl, then X is H.

In particular embodiments, X is (i) a substituted or unsubstituted $C_1$-$C_6$ alkyl and Y is halogen; or (ii) aromatic and Y is halogen. In particular embodiments, X and Z are H; Y and Z are H; X is aromatic and Y is halogen; X is aromatic and Y is a substituted or unsubstituted $C_1$-$C_6$ alkyl; X is aromatic and Y is a substituted or unsubstituted $C_1$-$C_6$ alkoxy; and Y is a substituted or unsubstituted $C_1$-$C_6$ alkyl, halogen or a substituted or unsubstituted $C_1$-$C_6$ alkoxy.

In another embodiment, there is provided a method of inducing cardiogenic differentiation in a stem cell comprising contacting said stem cell with a compound having the formula as shown above, or as shown below:

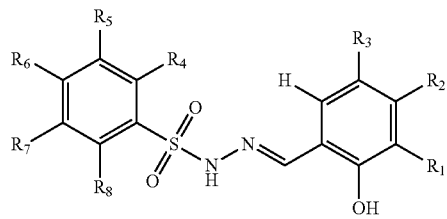

wherein $R_1$, $R_2$ and $R_3$ are each independently selected from the group consisting of hydrogen, substituted or unsubstituted $C_1$-$C_6$ alkyl, $C_3$-$C_6$ cycloalkyl, hydroxyl, halogen, $C_1$-$C_6$ alkoxy, substituted or unsubstituted aromatic or heteroaromatic ring, cyano, nitro, acyl and thioacyl; $R_4$-$R_8$ are each independently selected from the group consisting of hydrogen, $C_1$-$C_6$ alkyl, $C_3$-$C_6$ cycloalkyl, halogen, hydroxyl, amino, aminoalkyl, $C_1$-$C_6$ alkoxy, substituted or unsubstituted aromatic or heteroaromatic ring, cyano, nitro, carboxylic acid and carboxylic ester.

In particular embodiments: $R_3$ is not hydrogen and $R_6$ is hydrogen (optionally, the other R groups are all hydrogen); $R_3$ is hydrogen and $R_6$ is not hydrogen (optionally, the other R groups are all hydrogen); $R_2$ is methyl (optionally, the other R groups are all hydrogen); $R_3$ is nitro and $R_6$ is halogen (optionally, the other R groups are all hydrogen); $R_3$ and $R_6$ are halogen (optionally, the other R groups are all hydrogen); $R_3$ is aromatic and $R_6$ is halogen, an alcohol, a substituted or unsubstituted $C_1$-$C_6$ alkyl or a substituted or unsubstituted alkoxy (optionally, the other R groups are all hydrogen); or $R_6$ is a substituted or unsubstituted $C_1$-$C_6$ alkyl, halogen or a substituted or unsubstituted alkoxy (optionally, the other R groups are all hydrogen). The stem cell may be located in an animal subject, or the stem cell may be contacted ex vivo.

In yet another embodiment, there is provided a composition comprising the formula, or a compound of the formula:

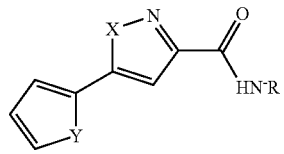

wherein X is O or NH, Y is S or O and R is H, a substituted or unsubstituted $C_1$-$C_6$ alkyl, $C_2$-$C_6$ alkenyl, $C_2$-$C_6$ alkynyl or $C_3$-$C_6$ cycloalkyl, with the provisos that if X is O, then R must be a substituted or unsubstituted $C_3$-$C_6$ cycloalkyl; and if X is NH, then R must not be pyrazinyl substituted $C_1$-$C_6$ alkyl.

In particular embodiments, Y is S and R is a substituted or unsubstituted $C_1$-$C_6$ alkyl; Y is S and R is a substituted or unsubstituted $C_3$-$C_6$ cycloalkyl; Y is O and R is a substituted or unsubstituted $C_3$-$C_6$ cycloalkyl; Y is O and R is a substituted or unsubstituted $C_1$-$C_6$ alkyl; R is a substituted or unsubstituted $C_2$-$C_6$ alkenyl; R is a substituted or unsubstituted $C_2$-$C_6$ alkynyl; R is H; X is O, Y is O and R is a substituted or unsubstituted cycloalkyl; or X is O, Y is S and R is a substituted or unsubstituted cycloalkyl.

In still yet a further embodiment, there is provided a method of inducing neurogenic differentiation in a stem cell comprising contacting said stem cell with a compound having the formula:

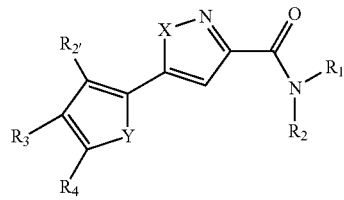

wherein $R_1$ and $R_2$ are both hydrogen or $R_1$ is hydrogen and $R_2$ is selected from the group consisting of substituted or unsubstituted $C_1$-$C_6$ alkyl, $C_3$-$C_6$ cycloalkyl, $C_2$-$C_6$ alkenyl, $C_2$-$C_6$ alkynyl, and benzyl, or where $R_1$ and $R_2$ may be joined together to form a ring selected from azetidinyl, pyrrolidinyl, piperidinyl, piperazinyl, or morpholinyl; $R_2'$, $R_3$ and $R_4$ are independently selected from the group consisting of hydrogen, halogen, $C_1$-$C_6$ alkyl, $C_3$-$C_6$ cycloalkyl, substituted or unsubstituted aromatic or heteroaromatic ring, cyano, nitro, and acyl; X is O, NH or S; and Y is O, NH or S.

In particular embodiments, Y is S and $R_2$ is a substituted or unsubstituted $C_1$-$C_6$ alkyl; Y is S and $R_2$ is a substituted or unsubstituted $C_3$-$C_6$ cycloalkyl; Y is O and $R_2$ is a substituted or unsubstituted $C_3$-$C_6$ cycloalkyl; Y is O and $R_2$ is a substituted or unsubstituted $C_1$-$C_6$ alkyl; Y is S and $R_2$ is a substituted or unsubstituted $C_2$-$C_6$ alkenyl, $C_2$-$C_6$ alkynyl or benzyl; Y is O and $R_2$ is a substituted or unsubstituted $C_2$-$C_6$ alkenyl, $C_2$-$C_6$ alkynyl or benzyl; or $R_1$ is H. The stem cell may be located in an animal subject, or the stem cell may be contacted ex vivo.

In still another embodiment, there is provided a method of screening for a molecule having stem cell differentiating activity comprising the steps of (a) providing an embryonal carcinoma cell line having integrated into cellular genomes thereof a bacterial artificial chromosome (BAC) comprising a Nkx2.5 gene locus including all regulatory elements therefor, and a luciferase coding region, wherein said luciferase coding region is under the control of the Nkx2.5 promoter, said BAC being located at other than the site of the endogenous Nkx2.5 gene locus; (b) contacting said cell line with a candidate substance; and (c) assessing expression of a luciferase gene product encoded by said luciferase coding region, wherein expression of said luciferase gene product indicates that said candidate substance is a molecule that has stem cell differentiating activity. The embryonal carcinoma cell line is P19CL6. Assessing may comprise measuring mRNA expression activity of one or more cell differentiation markers, or immunologic detection of one or more cell differentiation markers, such as with microscopy.

In a further embodiment, there is provided a transgenic animal, cells of which comprise a bacterial artificial chromosome (BAC) comprising a Nkx2.5 gene locus including all regulatory elements therefor, and a luciferase coding region, wherein said luciferase coding region is under the control of the Nkx2.5 promoter, said BAC being located at other than the site of the endogenous Nkx2.5 gene locus. The animal may be a mouse. The invention also comprises an isolated cell from this transgenic animal.

In yet still another embodiment, there is provided an embryonal carcinoma cell which comprises in its genome a bacterial artificial chromosome (BAC) comprising a Nkx2.5 gene locus including all regulatory elements therefor, and a luciferase coding region, wherein said luciferase coding region is under the control of the Nkx2.5 promoter, said BAC being located at other than the site of the endogenous Nkx2.5 gene locus.

Another general aspect of the present invention contemplates a method of treating a subject with a brain tumor comprising administering to a said subject a compound having the formula:

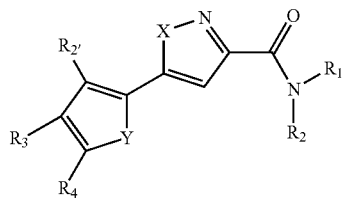

wherein $R_1$ and $R_2$ are both hydrogen or $R_1$ is hydrogen and $R_2$ is selected from the group consisting of substituted or unsubstituted $C_1$-$C_6$ alkyl, $C_3$-$C_6$ cycloalkyl, $C_2$-$C_6$ alkenyl, $C_2$-$C_6$ alkynyl, and benzyl, or where $R_1$ and $R_2$ may be joined together to form a ring selected from azetidinyl, pyrrolidinyl, piperidinyl, piperazinyl, or morpholinyl; $R_{2'}$, $R_3$ and $R_4$ are independently selected from the group consisting of hydrogen, halogen, $C_1$-$C_6$ alkyl, $C_3$-$C_6$ cycloalkyl, substituted or unsubstituted aromatic or heteroaromatic ring, cyano, nitro, and acyl; X is O, NH or S; and Y is O, NH or S. In certain embodiments, the brain tumor is selected from the group consisting of a glioma, a glioblastoma, an astrocytoma, an oligodendroglioma, an ependymoma, a meningioma, or a medulloblastoma. In particular embodiments, the brain tumor is glioblastoma multiforme, anaplastic astrocytoma, infiltrative astrocytoma, pilocytic astrocytoma, mixed oligoastrocytoma, or mixed glioma. The compound may be administered intratumorally, for example. Such methods may further comprise resection of the tumor. In such embodiments, the compound may be administered to the tumor bed after the tumor has been resected.

It is contemplated that any method, compound or composition described herein can be implemented with respect to any other method or composition described herein.

For any embodiment that refers to a composition, a compound may be used, and vice versa, unless specifically noted otherwise.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-G—Nkx2.5 cardiogenic small-molecule HTS in P19CL6 cells. (FIG. 1A) Schematic of reporter transgene with *luciferase* inserted by homologous recombination into the Nkx2.5 locus on an ~178 kb mouse BAC. (FIG. 1B) in vitro luciferase assay of Nkx2.5-luc BAC transgenic mouse confirming cardiac tissue-restricted expression. (FIG. 1C) Nkx2.5-luc BAC transgenic P19CL6 cell line, clone #5-1, with specific induction of luciferase protein (detected by immunostaining) following exposure to 2.5 mM NaB for three days (lower right panel), compared to DMSO vehicle control which showed a lack of luciferase staining (upper right panel). (FIG. 1D) NaB-mediated induction of Nkx2.5 mRNA by real-time RT-PCR in parental P19CL6 cells and (FIG. 1E) NaB-mediated induction of Nkx2.5 protein (FITC) in spontaneously beating cardiomyocytes, co-stained with α-actinin (Rhodamine). (FIG. 1F) Dose-responsive activation of Nkx2.5-luc BAC by Shz-1 in clone #5-1 P19CL6 reporter cells at 48 hours drug exposure. Each data point represents the average plus S.D. of 12 wells from a 96-well plate. (FIG. 1G) Dose-responsive activation of Nkx2.5 mRNA by Shz-1 in P19CL6 cells at 48 hours drug exposure, measured by real time RT-PCR and normalized to GAPDH mRNA levels. Scale bars=25 μm.

FIGS. 2A-G—Shz activation of myocardin reporter genes in P19CL6 and mouse ES cells. (FIG. 2A) Activation of myocardin-luc BAC by Shz-3 but not Shz-4 @ 2.5 μM in transgenic P19CL6 reporter cells at 48 hours drug exposure. Each data point represents the average plus S.D. of 12 wells from a 96-well plate. (FIG. 2B) Activation of endogenous myocardin tagged by homologous recombination with luciferase in SM1 mouse ES cell genome by Shz-1. Luciferase activity was measure 48 hours after removal of LIF and exposure to Shz-1 @ 2.5 μM. Each data point represents the average plus S.D. of 12 wells from a 96-well plate. (FIG. 2C) Dose-responsive activation of myocardin mRNA by Shz-1 in P19CL6 cells at 48 hours drug exposure, measured by real time RT-PCR and normalized to GAPDH mRNA levels. (FIG. 2D) Activation of endogenous myocardin mRNA in SM1 ES cells by Shz-1 @ 2.5 µM at 48 hours after drug exposure and removal of LIF, measured by real time RT-PCR and normalized to GAPDH mRNA levels. (FIG. 2E) Activation of endogenous brachyury-T mRNA in SM1 ES cells by Shz-1 @ 2.5 µM at 48 hours drug exposure and removal of LIF, measured by real time RT-PCR and normalized to GAPDH mRNA levels. (FIG. 2F) Expression of sarcomeric α-tropomyosin detected by CH1 mAb in vehicle (left panel) or Shz-1 treated (middle and right panels) P19CL6 cells@ 2.5 µM following 72 hours drug exposure. (FIG. 2G) Dose-responsive activation of SαTM in P19CL6 cells by protein blot with CH1 mAb; GAPDH protein levels are shown to document equal loading. Scale bar=30 µm.

FIGS. 3A-B—Interrogation of known cardiogenic signaling pathways. (FIG. 3A) Like Shz-1, BMP-2 (50 ng/ml) activated the Nkx2.5-luc BAC in P19CL6 cells. However, the BMP-antagonist Noggin (500 ng/ml) did not significantly block Shz-1 mediated signaling at 48 hours. Each data point is the average+S.D. of 12 wells from 96-well plate. (FIG. 3B) Representative cell staining demonstrating induction of SαTM by Shz-1 (2.5 µM) (left panel), GATA-4 by BMP-2 (50 ng/ml) (middle panel) and Oct3/4 by FGF-2 (20 ng/ml) (right panel) after exposure to agent for 48 hours. Scale bar=25 µm.

FIGS. 4A-D—Small-molecule treatment of human M-PBMCs in vitro. (FIG. 4A) Schematic of human M-PMNCs treatment protocol, 3 days with drug (10 µM) or vehicle control, then 7 days in drug-free media with media changes every 2-3 days. (FIG. 4B) Dose-responsive increase in M-PBMCs attachment/survival with increasing concentration of Shz-1 for first 3 days or vehicle control; average cell counts on day 10 of at least ten representative low power fields (lpf)+/−S.D. (FIG. 4C) Activation of cardiac differentiation by Shz small-molecules in human M-PBMCs in vitro. M-PBMCs were treated with vehicle or Shz-3 for 3 days, followed by 7 days in drug-free media, harvested and analyzed by RT-PCR for Nkx2.5, ANP and GAPDH transcripts; adult human heart mRNA was used a positive control (FIG. 4D) M-PBMCs from a different donor were harvested before treatment (day 0) or treated with Shz-1 for 3 days, followed by 7 days in drug-free media, harvested and analyzed with heart muscle control by RT-PCR for cTnI and GAPDH transcripts.

FIGS. 5A-D—Functional rescue of cryo-injured rat heart by Shz treated human M-PBMC xenografts. (FIG. 5A) Viable human M-PBMCs pre-treated for 3 days with compound Shz-3 (at 5 µM) or vehicle control, followed by 7 days in drug-free media, were injected by needle into the healthy myocardial perimeter of liquid nitrogen probe-mediated trans-mural burn injury. (FIG. 5B) Serial echocardiography was done at baseline (preinjury) and on days 3, 7, 14 and 21 after injury/xenografting, and the fractional shortening was calculated for each animal (n=4, each group) and was compared to hearts that had received mock injection with media alone (no cells). At days 7, 14 and 21, the difference between Shz-3 small-molecule and vehicle treated human M-PBMC xenografts was statistically significant, P=0.00183, P=0.00023 and P=0.000238 respectively. (FIG. 5C) IHC of chimeric juxta-burn myocardial tissue from rat injected with in vitro DAPI-stained Shz-3 treated human M-PBMCs using an α-actinin mAb that detects α-actinin exclusively in host rat myocardium (human cells evident by DAPI stained nuclei are negative) (left panel) versus a human-specific cTnI mAb that exclusively detects viable human drug-induced (cardiac gene expressing) cells in the needle-track (right panel). Scale bar=25 µm. The inset panel (FIG. 5C) shows that human M-PBMCs treated with drug and immunostained in vitro appear morphologically very similar to their in vivo counterparts. Scale bar=10 µm. (FIG. 5D) RT-PCR of RNA from chimeric juxta-burn tissue of hearts injected with Shz-3 or vehicle treated cells under high stringency conditions that favor amplification of human versus rat Nkx2.5 or cTnI sequences. 18S ribosomal RNA is the control for RNA loading. Human and rat hearts are used as positive and negative controls, respectively.

(FIG. 6B) A typical plate from the HTS. Positive hits, like Shz-1 shown here, were selected as having ≧2 fold higher RLU activity (red line) than the plate median (black line). NaB levels typically were 4-fold higher than plate median (green line) and DMSO/vehicle was at the median (yellow line). The Z' value for this particular plate was 0.65.

(FIG. 10B) DNA sequence of human cDNAs cloned from chimeric juxta-burn myocardial tissue confirmed the presence of human-specific gene transcripts for Nkx2.5 and cTnI.

FIG. 11—Sulfonyl-hydrazones from primary screen (top). Chemical structure map of active and a subset of inactive small-molecules containing Shz core motif that resulted from the screen. Note that Y must be OH for activity in this assay. Re-synthesis of sulfonyl-hydrazone (bottom). Chemical reaction used to re-synthesize original hits and novel Shz small-molecules for this study. iPrOH is isopropanol.

FIGS. 12A-B—Activation of SαTM in H9c2 embryonic rat cardiomyogenic cells. (FIG. 12A) H9c2 cells in serum-containing media treated with vehicle (left panel) or Shz-1 (right panel) detected by immunostaining with CH1 mAb. Scale bar=25 µm. (FIG. 12B) Protein time course for vehicle or Shz-1 induction of H9c2 cells and with GAPDH protein levels to document equal loading.

FIGS. 13A-C—Shz-mediated ERK-MAPK signaling in P19CL6 and H9c2 cells. (FIG. 13A) P19CL6 EC cells were briefly serum-starved (1 hr), then stimulated for 20 min with increasing concentrations of Shz-1 or vehicle control, and then extracts were prepared for blotting with ERK-MAPK pathway phosphoprotein antibodies or GAPDH as loading control. (FIGS. 13B-C) The MEK inhibitor U0126 blocked Shz-1 pharmacological activation of ERK1/2 (FIG. 13B), but did not attenuate the ability of Shz-1 to induce the Nkx2.5-luc BAC reporter gene in P19CL6 cells (FIG. 13C). NS=non-specific band in (FIG. 13B) that confirms equivalent protein loading.

FIGS. 14A-D—Activity of isoxazoles (Isx) against brain cancer stem cells. Isx treatment blocks the ability of human glioma cells (U87MG cell line from ATCC) to proliferate and form colonies in soft agar (FIG. 14A) and causes death of lung adenocarcinoma cells from human patients, but not control immortalized bronchial epithelial cells from the same patient (FIG. 14B). Within three days of Isx treatment (30 mM), there are profound morphological changes indicative of neuronal differentiation, confirmed by IHC staining (Tuj1, an early neuronal marker) (green) and protein expression (Tuj1 and DCX, both markers of immature neurons). Isx also blocks the growth of astrocytoma cells, demonstrated by the rarity of BrdU-positive cells (red) and these cultures (FIG. 14C). Finally, Isx rapidly induces chromatin modification (hyperacetylation of histones H3 and H4) with 24 hours in human glioblastoma cancer stem cells, and these changes are associated with marked neuronal differentiation (Map2ab and Tuj1 are tow neuronal markers) (FIG. 14D).

FIGS. 15A-I—Isoxazole-induced neuronal differentiation in adult hippocampal neural stem/progenitor cells. Isoxazoles induce neuronal fate commitment. (FIGS. 15A-B) 5 or 10 μM Isx treatment for 24 hours triggered at least a 5-fold induction of NeuroD- and GluR2-luciferase compared to FGF-2 or vehicle (DMSO) controls, and compared to 1 μM retinoic acid (RA), a positive control for inducing neuronal differentiation. (FIGS. 15C,D) Treatment of NPCs with vehicle (FIG. 15C) or 20 μM Isx (FIG. 15D) for 4 days and stained with Tuj1 (red) and Map2ab (green). (FIGS. 15E,F) Treatment of NPCs with 50 ng/ml LIF+50 ng/ml BMP-2 with vehicle (FIG. 15E) or together with 20 μM Isx (FIG. 15F) for 4 days and stained with Tuj1 (red) and GFAP (green). DAPI-stained nuclei (blue) and scale bar is 25 μm. (FIG. 15G) Quantification of Tuj1+ neurons with vehicle (white bars) or 20 μM Isx treatment (black bars) from 1-4 days. All data shown are from at least two experiments in parallel cultures with error bars representing standard deviations. (FIG. 15H) RT-PCR of NeuroD, GluR2, Tuj1, and NR1 in NPCs treated with FGF-2, vehicle (DMSO) or 20 μM Isx for 3 hrs, 1 and 3 days. (FIG. 15I) Protein blotting time-course analysis of NPCs at time 0 or treated with 20 μM Isx for up to 8 days. For RT-PCR and protein blotting, Gapdh mRNA and protein levels were used as normalization controls.

DESCRIPTION OF ILLUSTRATIVE EMBODIMENTS

Figure 6A:
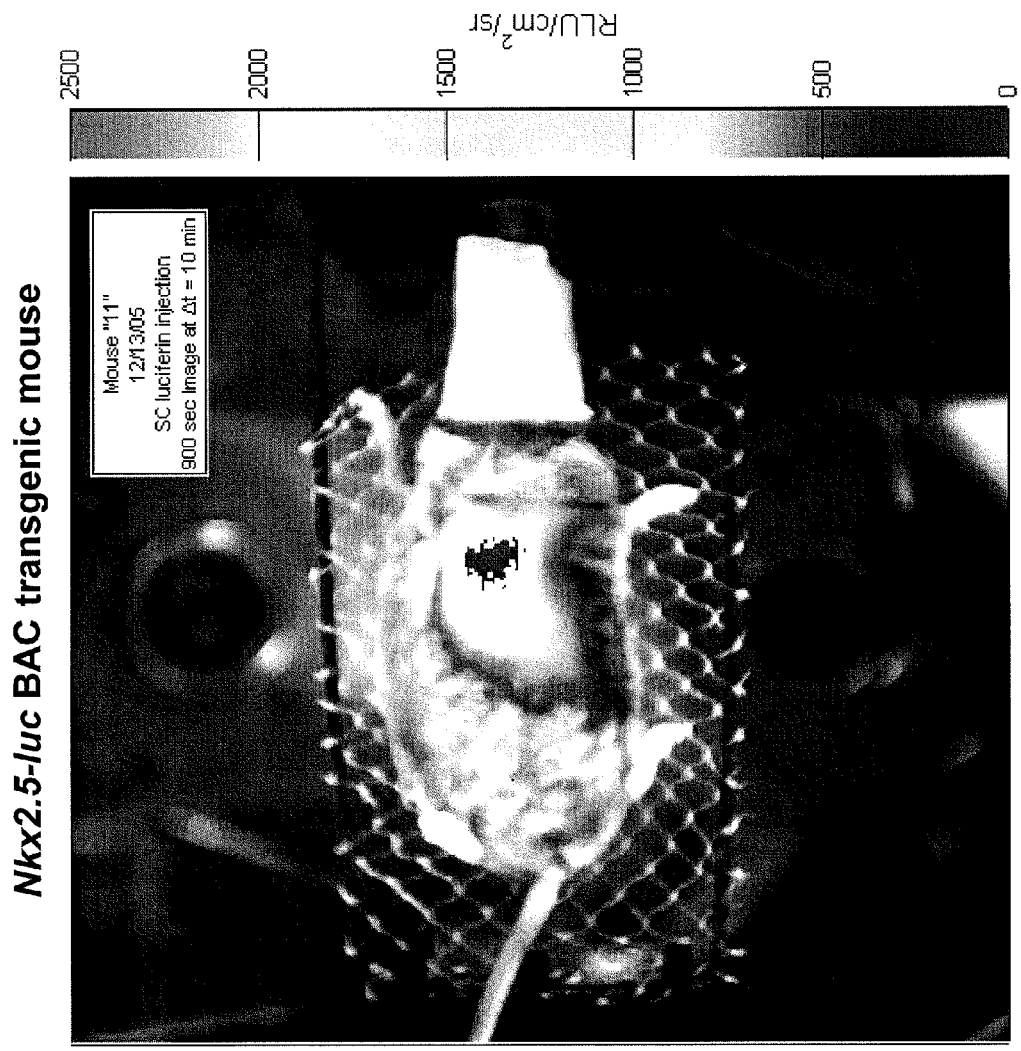
FIGS. 6A-B—(FIG. 6A) Bioluminescence of Nkx2.5-luc BAC transgenic mouse confirming cardiac tissue-restricted expression.

Increasing clinical success of stem cell therapy for myocardial repair is coupled to the need for better understanding of cardiac fate mechanisms. Here, the inventors report the identification of small-molecules involved in cardiac fate by screening a chemical library for activators of the signature gene, Nkx2.5, using a luciferase knock-in bacterial artificial chromosome (BAC) in mouse P19CL6 pluripotent stem cells. This family of sulfonyl-hydrazone (Shz) small-molecules can trigger cardiac mRNA and protein expression in a variety of embryonic and adult stem/progenitor cells, including human mobilized peripheral blood mononuclear cells (M-PBMCs). Small-molecule enhanced M-PBMCs engrafted into the rat heart in proximity of an experimental injury improved cardiac function better than control cells. Recovery of cardiac function correlated with persistence of viable human cells, expressing human-specific cardiac mRNAs and proteins. Shz small-molecules are thus promising drugs to promote myocardial repair/regeneration by activating cardiac differentiation in stem.

The inventors also discovered, as part of the same screening endeavor, compounds that are able to induce neuronal differentiation in the same stem cell populations. The compounds, generally described as isoxazoles, can be used to trigger neuronal mRNA and protein expression in a variety of embryonic and adult stem/progenitor cells, including human bone marrow stromal cells (BMSCs). Small-molecule enhanced BMSCs engrafted into the brain or spinal chord may assist with the recovery of neuronal function following injury or disease. Isoxazoles are thus promising drugs to promote neuronal repair/regeneration by activating neuronal differentiation in stem cells.

Over the past several years the concept of cancer stem cells has been extended from hematological malignancies to epithelial cancers including gliomas. Although the mechanistic understanding of cancer stem cells remains limited, the concept raises fundamental issues about the cellular origins of cancer as well as tumor progression and maintenance, and therefore has important implications for the development of therapeutics. At its core, the cancer stem cell hypothesis proposes that a small (<1-5%) fraction of the tumor cells are exclusively responsible for maintaining tumor burden and represent the most recalcitrant cell types to conventional radiotherapy and chemotherapy. The clear implications are that effective cancer therapies must be able to target and destroy the cancer stem cells. Discovery of this small molecule family, which contains an isoxazole core structural motif, provides both an important mechanistic clue to the cancer stem cell hypothesis as it applies to gliomas, and provides for development of novel chemotherapeutic agents that can specifically target cancer stem cells.

These, and other aspects of the invention, are set out in detail below.

I. Compounds

A. Sulfonyl Hydrazone Compounds

The sulfonyl hydrazone compounds of the present invention will generally have the following formula:

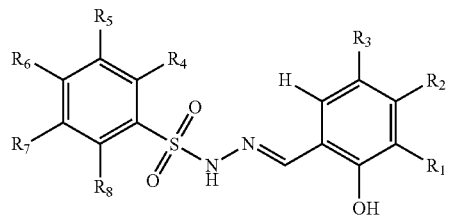

wherein $R_1$, $R_2$ and $R_3$ are each independently selected from the group consisting of hydrogen, substituted or unsubstituted $C_1$-$C_6$ alkyl, $C_3$-$C_6$ cycloalkyl, hydroxyl, halogen, $C_1$-$C_6$ alkoxy, substituted or unsubstituted aromatic or heteroaromatic ring, cyano, nitro, acyl and thioacyl; $R_4$-$R_8$ are each independently selected from the group consisting of hydrogen, $C_1$-$C_6$ alkyl, $C_3$-$C_6$ cycloalkyl, halogen, hydroxyl, amino, aminoalkyl, $C_1$-$C_6$ alkoxy, substituted or unsubstituted aromatic or heteroaromatic ring, cyano, nitro, carboxylic acid and carboxylic ester.

A representative synthesis of a sulfonyl hydrazone compound is as follows:

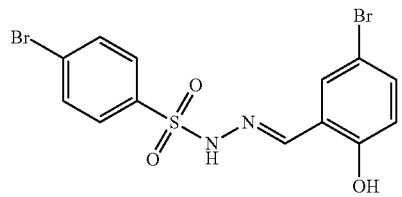

(E)-4-bromo-N'-(5-bromo-2-hydroxybenzylidene) benzenesulfonohydrazide

A mixture of 4-bromobenzenesulfonyl hydrazide (250 mg, 1.0 mmol), 5-bromosalicylaldehyde (120 mg, 1.0 mmol) and catalytic H₂SO₄ (1 drop) in isopropanol (5 mL) was heated to 90° C. for 6 hours. The reaction was cooled to room temperature and which point water (2 mL) was added dropwise to precipitate out the desired product. The product was collected by vacuum filtration and dried in vacuo to give the title compound (245 mg, 89% yield). $\delta_H$ (400 MHz, d⁶ DMSO): 11.71 (1H, br s), 10.41 (1H, s), 8.10 (1H, s), 7.82 (2H, d), 7.76 (2H, d), 7.58 (1H, d), 7.38 (1H, dd), 6.81 (1H, d).

B. Isoxazole Compounds

An isoxazole compound of the present invention will generally have the formula:

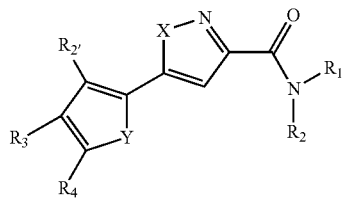

wherein $R_1$ and $R_2$ are both hydrogen or $R_1$ is hydrogen and $R_2$ is selected from the group consisting of substituted or unsubstituted $C_1$-$C_6$ alkyl, $C_3$-$C_6$ cycloalkyl, $C_2$-$C_6$ alkenyl, $C_2$-$C_6$ alkynyl, and benzyl, or where $R_1$ and $R_2$ may be joined together to form a ring selected from azetidinyl, pyrrolidinyl, piperidinyl, piperazinyl, or morpholinyl; $R_2'$, $R_3$ and $R_4$ are independently selected from the group consisting of hydrogen, halogen, $C_1$-$C_6$ alkyl, $C_3$-$C_6$ cycloalkyl, substituted or unsubstituted aromatic or heteroaromatic ring, cyano, nitro, and acyl; X is O, NH or S; and Y is O, NH or S.

A representative synthesis of an isoxazole compounds is provided below:

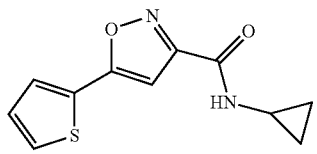

N-cyclopropyl-5-(thiophen-2-yl)isoxazole-3-carboxamide

To a solution of ethyl 5-(thiophen-2-yl)isoxazole-3-carboxylate (220 mg, 1 mmol) in absolute ethanol (5 mL) was added cyclopropylamine (285 mg, 5 mmol). The reaction was sealed and heated to 80° C. for 24 hours. The reaction was allowed to cool to room temperature and water (1 mL) was added. The product was collected by vacuum filtration as a white crystalline solid (150 mg, 64% yield). $\delta_H$ (400 MHz, d⁶ DMSO): 8.85 (1H, d), 7.83 (1H, d), 7.76 (1H, d), 7.24 (1H, d), 7.18 (1H, s), 2.83 (1H, m), 0.58-0.71 (4H, m).

C. Definitions

As used herein, the term "amino" means —NH₂; the term "nitro" means —NO₂; the term "halo" designates —F, —Cl, —Br or —I; the term "mercapto" means —SH; the term "cyano" means —CN; the term "azido" means —N₃; the term "silyl" means —SiH₃, and the term "hydroxy" means —OH.

The term "alkyl" includes straight-chain alkyl, branched-chain alkyl, cyclic alkyl, heteroatom-unsubstituted alkyl, heteroatom-substituted alkyl, heteroatom-unsubstituted $C_n$-alkyl, and heteroatom-substituted $C_n$-alkyl. The term "heteroatom-unsubstituted $C_n$-alkyl" refers to a radical, having a linear or branched structure, further having no carbon-carbon double or triple bonds, further having a total of n carbon atoms, all of which are nonaromatic, 3 or more hydrogen atoms, and no heteroatoms. For example, a heteroatom-unsubstituted $C_1$-$C_{10}$-alkyl has 1 to 10 carbon atoms. The groups, —CH₃ (Me), —CH₂CH₃ (Et), —CH₂CH₂CH₃ (n-Pr), —CH(CH₃)₂ (iso-Pr), —CH(CH₂)₂ (cyclopropyl), —CH₂CH₂CH₂CH₃ (n-Bu), —CH(CH₃)CH₂CH₃ (sec-butyl), —CH₂CH(CH₃)₂ (iso-butyl), —C(CH₃)₃ (tert-butyl), —CH₂C(CH₃)₃ (neo-pentyl), are all non-limiting examples of heteroatom-unsubstituted alkyl groups. The term "heteroatom-substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a heteroatom-substituted $C_1$-$C_{10}$-alkyl has 1 to 10 carbon atoms. The following groups are all non-limiting examples of heteroatom-substituted alkyl groups: trifluoromethyl, —CH₂F, —CH₂Cl, —CH₂Br, —CH₂OH, —CH₂OCH₃, —CH₂OCH₂CF₃, —CH₂OC(O)CH₃, —CH₂NH₂, —CH₂NHCH₃, —CH₂N(CH₃)₂, —CH₂CH₂Cl, —CH₂CH₂OH, CH₂CH₂OC(O)CH₃, —CH₂CH₂NHCO₂C(CH₃)₃, and —CH₂Si(CH₃)₃. It is specifically contemplated that for any alkyl group reciting $C_{1-6}$ carbons or any range derivable therein, that that alkyl group may contain 1, 2, 3, 4, 5, or 6 carbon atoms, or any range derivable therein. Alkyl groups containing 1, 2, 3, 4, 5, or 6 carbon atoms or any range derivable therein, are contemplated for any embodiment discussed herein. An "aminoalkyl" group is a version of a heteroatom-substituted alkyl group that comprises an NH₂ group. A C1-C6 alcohol is a version of a heteroatom-substituted alkyl group that comprises a hydroxy group.

The term "alkenyl" includes straight-chain alkenyl, branched-chain alkenyl, heteroatom-unsubstituted alkenyl, heteroatom-substituted alkenyl, heteroatom-unsubstituted $C_n$-alkenyl, and heteroatom-substituted $C_n$-alkenyl. The term "heteroatom-unsubstituted $C_n$-alkenyl" refers to a radical, having a linear or branched structure, further having at least one nonaromatic carbon-carbon double bond, but no carbon-carbon triple bonds, a total of n carbon atoms, three or more hydrogen atoms, and no heteroatoms. For example, a heteroatom-unsubstituted $C_2$-$C_{10}$-alkenyl has 2 to 10 carbon atoms. Heteroatom-unsubstituted alkenyl groups include: —CH=CH₂ (vinyl), —CH=CHCH₃, —CH=CHCH₂CH₃, —CH₂CH=CH₂ (allyl), —CH₂CH=CHCH₃, and —CH=CH—C₆H₅. The term "heteroatom-substituted $C_n$-alkenyl" refers to a radical, having a single nonaromatic carbon atom as the point of attachment and at least one nonaromatic carbon-carbon double bond, but no carbon-carbon triple bonds, further having a linear or branched structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkenyl has 2 to 10 carbon atoms. The groups, —CH=CHF, —CH=CHCl and —CH=CHBr, are non-limiting examples of heteroatom-substituted alkenyl groups.

The term "alkynyl" includes straight-chain alkynyl, branched-chain alkynyl, heteroatom-unsubstituted alkynyl, heteroatom-substituted alkynyl, heteroatom-unsubstituted $C_n$-alkynyl, and heteroatom-substituted $C_n$-alkynyl. The term "heteroatom-unsubstituted $C_n$-alkynyl" refers to a radical, having a linear or branched structure, further having at least one carbon-carbon triple bond, a total of n carbon atoms, at least one hydrogen atom, and no heteroatoms. For example, a heteroatom-unsubstituted $C_2$-$C_{10}$-alkynyl has 2 to 10 carbon atoms. The groups, —C≡CH, —C≡CCH$_3$, and —C≡CC$_6$H$_5$ are non-limiting examples of heteroatom-unsubstituted alkynyl groups. The term "heteroatom-substituted $C_n$-alkynyl" refers to a radical, having a single nonaromatic carbon atom as the point of attachment and at least one carbon-carbon triple bond, further having a linear or branched structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a heteroatom-substituted $C_2$-$C_{10}$-alkynyl has 2 to 10 carbon atoms. The group, —C≡CSi(CH$_3$)$_3$, is a non-limiting example of a heteroatom-substituted alkynyl group.

The terms "aromatic," "aromatic ring structure", "aromatic ring" or "aryl" includes heteroatom-unsubstituted aryl, heteroatom-substituted aryl, heteroatom-unsubstituted $C_n$-aryl, heteroatom-substituted $C_n$-aryl, heteroaryl (also called heteroaromatic (e.g., pyridinyl or indolyl)), heterocyclic aryl groups, carbocyclic aryl groups, biaryl groups, and single-valent radicals derived from polycyclic fused hydrocarbons (PAHs). The term "heteroatom-unsubstituted $C_n$-aryl" refers to a radical, having a single carbon atom as the point of attachment, wherein the carbon atom is part of an aromatic ring structure containing only carbon atoms, further having a total of n carbon atoms, 5 or more hydrogen atoms, and no heteroatoms. For example, a heteroatom-unsubstituted $C_6$-$C_{10}$-aryl has 6 to 10 carbon atoms. Non-limiting examples of heteroatom-unsubstituted aryl groups include phenyl (Ph), methylphenyl, (dimethyl)phenyl, —C$_6$H$_4$—CH$_2$CH$_3$, —C$_6$H$_4$CH$_2$CH$_2$CH$_3$, —C$_6$H$_4$CH(CH$_3$)$_2$, —C$_6$H$_4$CH(CH$_2$)$_2$, —C$_6$H$_3$(CH$_3$)CH$_2$CH$_3$, —C$_6$H$_4$CH=CH$_2$, —C$_6$H$_4$CH=CHCH$_3$, —C$_6$H$_4$C≡CH, —C$_6$H$_4$C≡CCH$_3$, naphthyl, and the radical derived from biphenyl. The term "heteroatom-substituted $C_n$-aryl" refers to a radical, having either a single aromatic carbon atom or a single aromatic heteroatom as the point of attachment, further having a total of n carbon atoms, at least one hydrogen atom, and at least one heteroatom, further wherein each heteroatom is independently selected from the group consisting of N, O, F, Cl, Br, I, Si, P, and S. For example, a heteroatom-unsubstituted $C_1$-$C_{10}$-heteroaryl has 1 to 10 carbon atoms. Non-limiting examples of heteroatom-substituted aryl groups include the groups: —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OC(O)CH$_3$, —C$_6$H$_4$NH$_2$, —C$_6$H$_4$NH$_3$, —C$_6$H$_4$N(CH$_3$)$_2$, —C$_6$H$_4$CH$_2$OH, —C$_6$H$_4$CH$_2$C(O)CH$_3$, —C$_6$H$_4$CH$_2$NH$_2$, —C$_6$H$_4$CF$_3$, —C$_6$H$_4$CN, —C$_6$H$_4$CHO, —C$_6$H$_4$CHO, —C$_6$H$_4$C(O)CH$_3$, —C$_6$H$_4$C(O)C$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, furanyl, thienyl, pyridyl, pyrrolyl, pyrimidyl, pyrazinyl, quinolyl, indolyl, and imidazoyl.

The term "acyl" includes straight-chain acyl, branched-chain acyl, cycloacyl, cyclic acyl, heteroatom-unsubstituted acyl, heteroatom-substituted acyl, heteroatom-unsubstituted $C_n$-acyl, heteroatom-substituted $C_n$-acyl, alkylcarbonyl, alkoxycarbonyl and aminocarbonyl groups. The term "heteroatom-unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, a heteroatom-unsubstituted $C_1$-$C_{10}$-acyl has 1 to 10 carbon atoms. The groups, —CHO, —C(O)CH$_3$, —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)C$_6$H$_4$CH$_2$CH$_3$, and —COC$_6$H$_3$(CH$_3$)$_2$, are non-limiting examples of heteroatom-unsubstituted acyl groups. The term "heteroatom-substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom, in addition to the oxygen of the carbonyl group, wherein each additional heteroatom is independently selected from the group consisting of N, O, F, Cl, Br, I, Si, P, and S. For example, a heteroatom-substituted $C_1$-$C_{10}$-acyl has 1 to 10 carbon atoms. The groups, —C(O)CH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —C(O)NH$_2$ (carbamoyl), —C(O)NHCH$_3$, —C(O)NHCH$_2$CH$_3$, —CONHCH(CH$_3$)$_2$, —CONHCH(CH$_2$)$_2$, —CON(CH$_3$)$_2$, and —CONHCH$_2$CF$_3$, are non-limiting examples of heteroatom-substituted acyl groups. In certain embodiments, a carboxylic ester is contemplated, which is defined as —C(O)-alkyl, as alkyl is defined herein. Thioacyl groups are also contemplated, wherein the oxygen of the acyl group as described in this paragraph is replaced by a sulfur. In any embodiment that employs an acyl group, a thioacyl group may be employed, and vice versa.

The term "alkoxy" includes straight-chain alkoxy, branched-chain alkoxy, cycloalkoxy, cyclic alkoxy, heteroatom-unsubstituted alkoxy, heteroatom-substituted alkoxy, heteroatom-unsubstituted $C_n$-alkoxy, and heteroatom-substituted $C_n$-alkoxy. The term "heteroatom-unsubstituted $C_n$-alkoxy" refers to a group, having the structure —OR, in which R is a heteroatom-unsubstituted $C_n$-alkyl, as that term is defined above. Heteroatom-unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$. The term "heteroatom-substituted $C_n$-alkoxy" refers to a group, having the structure —OR, in which R is a heteroatom-substituted $C_n$-alkyl, as that term is defined above. For example, —OCH$_2$CF$_3$ is a heteroatom-substituted alkoxy group.

The term "alkylamino" includes straight-chain alkylamino, branched-chain alkylamino, cycloalkylamino, cyclic alkylamino, heteroatom-unsubstituted alkylamino, heteroatom-substituted alkylamino, heteroatom-unsubstituted $C_n$-alkylamino, and heteroatom-substituted $C_n$-alkylamino. Any substituent herein may be further defined as alkylamino. The term "heteroatom-unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, a heteroatom-unsubstituted $C_1$-$C_{10}$-alkylamino has 1 to 10 carbon atoms. The term "heteroatom-unsubstituted $C_n$-alkylamino" includes groups, having the structure —NHR, in which R is a heteroatom-unsubstituted $C_n$-alkyl, as that term is defined above. A heteroatom-unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl. The term "heteroatom-substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a heteroatom-substituted $C_1$-$C_{10}$-alkylamino has 1 to 10 carbon atoms. The term "heteroatom-substituted $C_n$-alkylamino" includes groups, having the structure —NHR, in which R is a heteroatom-substituted $C_n$-alkyl, as that term is defined above.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, Selection and Use* (P. H. Stahl & C. G. Wermuth eds., Verlag Helvetica Chimica Acta, 2002), which is incorporated herein by reference.

II. Stem Cells

Stem cells are primal cells found in all multi-cellular organisms. They retain the ability to renew themselves through mitotic cell division and can differentiate into a diverse range of specialized cell types. Research in the human stem cell field grew out of findings by Canadian scientists Ernest A. McCulloch and James E. Till in the 1960s.

The three broad categories of mammalian stem cells are: embryonic stem cells, derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body, replenishing specialized cells.

As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from the umbilical cord blood or bone marrow are touted as promising candidates.

"Potency" specifies the differentiation potential (the potential to differentiate into different cell types) of the stem cell. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal which distinguishes them from non-stem cells.

A. Embryonic Stem Cells

Embryonic stem cell lines (ES cell lines) are cultures of cells derived from the epiblast tissue of the inner cell mass (ICM) of a blastocyst. A blastocyst is an early stage embryo—approximately 4 to 5 days old in humans and consisting of 50-150 cells. ES cells are pluripotent, and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells are grown on a layer of gelatin and require the presence of Leukemia Inhibitory Factor (LIF). Human ES cells are grown on a feeder layer of mouse embryonic fibroblasts (MEF's) and require the presence of basic Fibroblast Growth Factor (bFGF or FGF-2). Without optimal culture conditions or genetic manipulation embryonic stem cells will rapidly differentiate.

A human embryonic stem cell is also defined by the presence of several transcription factors and cell surface proteins. The transcription factors Oct-4, Nanog, and Sox2 form the core regulatory network which ensures the suppression of genes that lead to differentiation and the maintenance of pluripotency. The cell surface proteins most commonly used to identify hES cells are the glycolipids SSEA3 and SSEA4 and the keratan sulfate antigens Tra-1-60 and Tra-1-81. The molecular definition of a stem cell includes many more proteins and continues to be a topic of research.

After 20 years of research, there are no approved treatments or human trials using embryonic stem cells. Their tendency to produce tumors and malignant carcinomas, cause transplant rejection, and form the wrong kinds of cells are just a few of the hurdles that embryonic stem cell researchers still face. Many nations currently have moratoria on either ES cell research or the production of new ES cell lines. Because of their combined abilities of unlimited expansion and pluripotency, embryonic stem cells remain a theoretically potential source for regenerative medicine and tissue replacement after injury or disease.

The present invention contemplates the use of embryonic stem cells. Table 1 lists cellular markers that can be used to identify and separate embryonic stem cells for use in accordance with the present invention.

TABLE 1

Pluripotent Stem Cell Markers

| Cell Marker | Cell Type | Significance |
|---|---|---|
| Alkaline phosphatase | Embryonic stem (ES), embryonal carcinoma (EC) | Elevated expression of this enzyme is associated with undifferentiated pluripotent stem cell (PSC) |
| Alpha-fetoprotein (AFP) | Endoderm | Protein expressed during development of primitive endoderm; reflects endodermal differentiation |
| Bone morphogenetic protein-4 | Mesoderm | Pluripotent Stem Cells Growth and differentiation factor expressed during early mesoderm formation and differentiation |
| Brachyury | Mesoderm | Transcription factor important in the earliest phases of mesoderm formation and differentiation; used as the earliest indicator of mesoderm formation |
| Cluster designation 30 (CD30) | ES, EC | Surface receptor molecule found specifically on PSC |
| Cripto (TDGF-1) | ES, cardiomyocyte | Gene for growth factor expressed by ES cells, primitive ectoderm, and developing cardiomyocyte |
| GATA-4 gene | Endoderm | Expression increases as ES differentiates into endoderm |
| GCTM-2 | ES, EC | Antibody to a specific extracellular-matrix molecule that is synthesized by undifferentiated PSCs |
| Genesis | ES, EC | Transcription factor uniquely expressed by ES cells either in or during the undifferentiated state of PSCs |
| Germ cell nuclear factor | ES, EC | Transcription factor expressed by PSCs |
| Hepatocyte nuclear factor-4 (HNF-4) | Endoderm | Transcription factor expressed early in endoderm formation |
| Nestin | Ectoderm, neural and pancreatic progenitor | Intermediate filaments within cells; characteristic of primitive neuroectoderm formation |
| Neuronal cell-adhesion molecule (N-CAM) | Ectoderm | Cell-surface molecule that promotes cell-cell interaction; indicates primitive neuroectoderm formation |
| Oct-4 | ES, EC | Transcription factor unique to PSCs; essential for establishment and |
| Pax6 | Ectoderm | maintenance of undifferentiated PSCs Transcription factor expressed as ES cell differentiates into neuroepithelium |
| Stage-specific embryonic antigen-3 (SSEA-3) | ES, EC | Glycoprotein specifically expressed in early embryonic development and by undifferentiated PSCs |
| Stage-specific embryonic antigen-4 (SSEA-4) | ES, EC | Glycoprotein specifically expressed in early embryonic development and by undifferentiated PSCs |
| Stem cell factor (SCF or c-Kit ligand) | ES, EC, HSC, MSC | Membrane protein that enhances proliferation of ES and EC cells, hematopoietic stem cell (HSCs), and mesenchymal stem cells (MSCs); binds the receptor c-Kit |
| Telomerase | ES, EC | An enzyme uniquely associated with immortal cell lines; useful for identifying undifferentiated PSCs |
| TRA-1-60 | ES, EC | Antibody to a specific extracellular matrix molecule is synthesized by undifferentiated PSCs |
| TRA-1-81 | ES, EC | Antibody to a specific extracellular matrix molecule normally synthesized by undifferentiated PSCs |
| Vimentin | Ectoderm, neural and pancreatic progenitor | Intermediate filaments within cells; characteristic of primitive neuroectoderm formation |

B. Adult Stem Cells

Adult stem cells, a cell which is found in a developed organism, has two properties: the ability to divide and create another cell like itself, and also divide and create a cell more differentiated than itself. Pluripotent adult stem cells are rare and generally small in number but can be found in a number of tissues including umbilical cord blood. Most adult stem cells are lineage restricted (multipotent) and are generally referred to by their tissue origin (mesenchymal stem cell, adipose-derived stem cell, endothelial stem cell, etc.). A great deal of adult stem cell research has focused on clarifying their capacity to divide or self-renew indefinitely and their differentiation potential.

While embryonic stem cell potential remains untested, adult stem cell treatments have been used for many years to successfully treat leukemia and related bone/blood cancers through bone marrow transplants. The use of adult stem cells in research and therapy is not as controversial as embryonic stem cells, because the production of adult stem cells does not require the destruction of an embryo. Consequently, more U.S. government funding is being provided for adult stem cell research.

The present invention contemplates, in particular, peripheral blood mononuclear cells as a source for cardiogenic stem cells, and bone marrow stromal cells as a source of neurogenic stem cells.

i. Cardiogenic Stem Cells

Evidence for potential stem cell-based therapies for heart disease has been provided by studies showing that human adult stem cells, taken from the bone marrow, are capable of giving rise to vascular endothelial cells when transplanted into rats. Such stem cells demonstrated plasticity, meaning that they become cell types that they would not normally be. The cells were used to form new blood vessels in the damaged area of the rats' hearts and to encourage proliferation of preexisting vasculature following the experimental heart attack.

Like the mouse stem cells, human hematopoietic stem cells can be induced under the appropriate culture conditions to differentiate into numerous tissue types, including cardiac muscle. When injected into the bloodstream leading to the damaged rat heart, these cells prevented the death of hypertrophied or thickened but otherwise viable myocardial cells and reduced progressive formation of collagen fibers and scars. Furthermore, hematopoietic cells can be identified on the basis of highly specific cell markers that differentiate them from cardiomyocyte precursor cells, enabling such cells to be used alone or in conjunction with myocyte-regeneration strategies or pharmacological therapies.

Table 2, below, lists cell surface markers that can be used to identify cardiogenic stem cells. In particular, Flk1' cells are contemplated.

TABLE 2

Cardiac Progenitor Markers

| Cell Marker | Cell Type | Significance |
| --- | --- | --- |
| MyoD and Pax7 | Myoblast, myocyte | Transcription factors that direct differentiation of myoblasts into mature myocytes |
| Myogenin and MR4 | Skeletal myocyte | Secondary transcription factors required for differentiation of myoblasts from muscle stem cells |
| Myosin heavy chain | Cardiomyocyte | A component of structural and contractile protein found in cardiomyocyte |
| Myosin light chain | Skeletal myocyte | A component of structural and contractile protein found in skeletal myocyte | ii. Neurogenic Stem Cells

The adult mammalian central nervous system (CNS) is composed primarily of three differentiated cell types—neurons, astrocytes and oligodendrocytes. Astrocytes and oligodendrocytes provide a critical supporting role for neuronal function. Neurons responsible for forming connections and are the communicating cells of the nervous system. The limits on adult mammals' ability to replace non-functional CNS tissue makes CNS death due to injury or disease devastating. Thus, research on brain repair has traditionally focused on keeping neurons alive following injury and promoting their ability to extend processes and establish functional cell connections. This focus was based on the belief that the adult mammalian CNS was incapable of generating new brain cells. However, the early 1990's brought the discovery of stem cells existed in the embryonic and adult CNS, opening up the way for research on the use of these cells in neuronal therapies and CNS tissue repair.

Neural stem cells have been isolated from nearly all regions of the embryonic mouse CNS, including the septum, cortex, thalamus, ventral mesencephalon and spinal cord. Cells from all these CNS regions exhibit the same general features—extensive proliferative ability, self-renewal and differentiation of the progeny into neurons, astrocytes and oligodendrocytes. In the adult mouse, neural stem cells appear to be located primarily in the sub-ventricular zone (SVZ) of the forebrain and in the sub-granular layer of the dentate gyms of the hippocampal formation. A recent study indicates the cells from the sub-granular layer may have a more limited proliferative potential, and that the hippocampal stem cells lie dorsal to the hippocampus in a collapsed ventricle.

While the role of neural stem cells in vivo is poorly understood, they do appear to exhibit properties similar to other stem cells. In the sub-ventricular region, for example, stem cells can be induced to proliferate and to repopulate the sub-ventricular zone following irradiation. Stem cell-derived subependymal progenitor cells are the source of new neurons in the olfactory bulb of rodents and in the association cortex of nonhuman primates under normal conditions. And recently, it has been shown that stem cell progeny in the hippocampal region are able to compensate for behavioral deficits following ischemic injury in rodents.

Table 3, below, lists various cell markers for neurogenic progenitor cells.

TABLE 3

Neurogenic Progenitor Markers

| Cell Marker | Cell Type | Significance |
| --- | --- | --- |
| CD133 | Neural stem cell, HSC | Cell-surface protein that identifies neural stem cells, which give rise to neurons and glial cells |
| Glial fibrillary acidic protein (GFAP) | Astrocyte | Protein specifically produced by astrocyte |
| Microtubule-associated protein-2 (MAP-2) | Neuron | Dendrite-specific MAP; protein found specifically in dendritic branching of neuron |
| Myelin basic protein (MPB) | Oligodendrocyte | Protein produced by mature oligodendrocytes; located in the myelin sheath surrounding neuronal structures |
| Nestin | Neural progenitor | Intermediate filament structural protein expressed in primitive neural tissue |
| Neural tubulin | Neuron | Important structural protein for neuron; identifies differentiated neuron |

TABLE 3-continued

Neurogenic Progenitor Markers

| Cell Marker | Cell Type | Significance |
| --- | --- | --- |
| Neurofilament (NF) | Neuron | Important structural protein for neuron; identifies differentiated neuron |
| Neurosphere | Embryoid body (EB), ES | Cluster of primitive neural cells in culture of differentiating ES cells; indicates presence of early neurons and glia |
| Noggin | Neuron | A neuron-specific gene expressed during the development of neurons |
| O4 | Oligodendrocyte | Cell-surface marker on immature, developing oligodendrocyte |
| O1 | Oligodendrocyte | Cell-surface marker that characterizes mature oligodendrocyte |
| Synaptophysin | Neuron | Neuronal protein located in synapses; indicates connections between neurons |
| Tau | Neuron | Type of MAP; helps maintain structure of the axon |

C. Cancer Stem Cells

Stem cells are functionally characterized by the ability to self renew and differentiate into distinct cell lineages. It has been established that embryonic stem (ES) cells, derived from the inner cell mass of the developing blastocyst, are pluripotent, undifferentiated cells with the potential to proliferate, self-renew, and generate new tissues. Such ES cells have now been isolated from both mouse and human embryos. In addition, stem cells have been identified within adult, differentiated tissues. These adult stem cells, sometimes also termed multi-potent adult progenitor cells (MAPCs), are believed to play essential roles in growth and tissue regeneration and have been identified in certain tissues, including the brain, epidermis, lung, breast, hematopoietic and neural systems. Gage, 2000; Abeyta et al., 2004; Tumbar et al., 2004; Zepeda et al., 1995; Dontu et al., 2003; Welm et al., 2002; Gudjonsson et al., 2002; Lagasse et al., 2001; Ramalho-Santos et al., 2002.

There is evidence that many common cancers, including skin and breast cancers, in addition to leukemias, can result from transforming events that occur in adult stem cells (Perez-Losada and Balmain, 2003; Al-Hajj et al., 2003; Reya et al., 2001). Indeed, functional parallels exist between tumorigenic and normal stem cells. Both cell types demonstrate significant proliferative potential, the ability to self-renew, and the ability to generate new tissues. However, tumorigenic stem cells lack the normal growth regulatory mechanisms that limit the uncontrolled proliferation of stem cells (Reya et al., 2001).

Tumorigenic stem cells arise in normal adult stem cell populations through the accumulation of multiple transforming mutations. As adult stem cells can persist and self-renew for the lifespan of the individual, these cells are more likely to accrue the genetic lesions necessary for malignant transformation. Such transformed tumorigenic stem cells, arising in normal adult stem cell populations, can initiate cancer development (Reya et al., 2001). Furthermore, tumorigenic stem cells may also play important roles in tumor evolution, metastatic invasion and local recurrence following treatment.

Cancer stem cells constitute only a small proportion of a tumor or a cancerous tissue. But the cancer stem cells have a unique ability to establish new colonies of cancer cells. For example, when mouse myeloma cells are obtained from mouse ascites, separated from normal hematopoietic cells, and put into in vitro colony-forming assays, only 1 in 10,000 to 1 in 100 cancer cells were able to form colonies (Park et al., 1971). Even when leukemic cells were transplanted in vivo, only 1-4% of cells could form spleen colonies (Bruce et al., 1963; Wodinsky et al., 1967; Bergsagel et al., 1968). Moreover it has been shown that a subset of cells from a population of seemingly homogeneous cancer cells is capable of proliferation and is clonogenic, while the remainder of cancer cells cannot undergo significant proliferation. Thus, workers have purified such a proliferative subset of leukemia cells as $CD34'CD38^-$ cells from patient samples (Bonnet and Dick, 1997). Despite the fact that these cells represented a small and variable proportion of acute myelogenic leukemia cells (0.2% in one patient), they were the only cells capable of transferring acute myelogenic leukemia (AML) from human patients to NOD/SCID mice in the vast majority of cases. Thus, not all AML cells had a similar clonogenic capacity. Only a small, identifiable subset was consistently enriched for the ability to proliferate and transfer disease.

As used herein, a cancer stem cell is a stem cell that has a cancerous phenotype. Cancer stem cells lack the normal growth regulatory mechanisms that limit the controlled proliferation of stem cells. Cancer stem cells constitute only a subset of cells from a population of seemingly homogeneous cancer cells. While cancer stem cells are capable of proliferation and are clonogenic, most cancer cells in a population of seemingly homogeneous cancer cells cannot undergo significant proliferation.

Compounds of the present invention may be used to treat cancer. For example, compounds of the present invention may be used to target cancer stem cells. In certain embodiments, combination therapy may be employed, wherein a compound of the present invention is administered to a cancer patient in addition to other therapy, such as surgery, chemotherapy and/or radiation therapy, wherein the compound of the present invention targets primarily the cancer stem cells and the chemo- or radiation therapy targets primarily the non-stem cell cancer cells. Combination therapy is discussed further below. Compounds of the present invention may also find use in on-going treatment after other cancer therapy (e.g., surgery, chemo- and/or radiation therapy) has been terminated. This approach would be designed to suppress cancer stem cells from forming cancerous tumors, and/or encourage stem cells with cancerous predilections to instead form non-cancerous cells. Determining whether a cancer patient possesses cancer stem cells, and thus could be a candidate for receiving compounds of the present invention in therapeutically effective amounts, could be determined, for example, by methods described in U.S. Publ. Appl. No. 2005/0277162, wherein Rex-1 is described as a cancer stem cell marker.

Other uses of compounds of the present invention in a cancer context contemplate administration of a compound of the present invention to a patient having a cancerous tumor. Curative surgery includes resection in which all or part of cancerous tissue is physically removed, excised, and/or destroyed. Tumor resection refers to physical removal of at least part of a tumor.

In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Accordingly, a compound of the present invention may be administered, for example, to treat a primary tumor, and following resection of the tumor, a compound of the present invention could continue to be administered to treat any residual, microscopic disease, be it comprised of cancer stem cells or cancer cells that are not stem cells. In this regard, treatment with a therapeutic amount of a compound of the present invention may increase the resectability of the tumor due to shrinkage at the margins or by elimination of certain particularly invasive portions. Additional treatments subsequent to resection may then serve to eliminate microscopic residual disease at the tumor site. The tumor may be a brain cancer tumor, for example.

Moreover, a compound of the present invention may be administered via placement of the compound directly at the site of the tumor bed such that the compound is released over time. For example, a compound of the present invention may be comprised in a wafer that is left in the tumor bed following resection of the tumor, wherein the wafer is attached to the edges of the resection cavity at the conclusion of surgical tumor removal. Such wafers have been employed in other contexts, such as biodegradable carmustine (BCNU) wafers for treatment of gliomas. Multiple wafers may be employed in such therapeutic intervention.

III. Detection of Cell Surface Markers

In accordance with the present invention, one will seek to obtain various stem cell populations by screening of cell populations for appropriate cell surface markers, as discussed above. Generally, this is performed by labeling or physically selecting cells that are bound by antibodies to cell determinants that identify the cells as stem, pluripotent or totipotent stem cells. It is particularly contemplated that antibodies will be of particular use in the various cell separation techniques described below.

A. Antibody Constructs

Antibodies directed against the various cell surface antigens are readily available from commercial sources. While available from commercial sources, it is also contemplated that monoclonal or polyclonal antibodies for use in the context of the invention may be constructed by a person of ordinary skill.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

B. Antibody Conjugates

The instant invention provides for the use of antibodies against various cell surface antigens which are generally of the monoclonal type, and that may be linked to at least one agent to form an antibody conjugate. It is conventional to link or covalently bind or complex at least one desired molecule or moiety. Such a molecule or moiety may be, but is not limited to a reporter molecule. A reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et al., 1993; Kreier et al., 1991). In addition, the variable domain is involved in antibody self-binding (Kang et al., 1988), and contains epitopes (idiotopes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired.

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might employ, by way of example, ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might employ, for example, $^{211}$astatine, $^{14}$-carbon, $^{51}$chromium, $^{36}$-chlorine, $^{57}$cobalt, $^{58}$cobalt, copper$^{67}$, $^{152}$t gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, $^{99m}$technicium and/or $^{90}$yttrium. $^{125}$I is often being preferred for use in certain embodiments, and $^{99m}$technicium and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

C. Methods of Conjugation

If desired, the compound of interest may be joined to an antibody via a biologically-releasable bond, such as a selectively-cleavable linker or amino acid sequence. Certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the moiety prior to binding at the site of action.

Additionally, any other linking/coupling agents and/or mechanisms known to those of skill in the art can be used to combine to components or agents with antibodies of the present invention, such as, for example, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, or combinations thereof.

Cross-linking reagents are used to form molecular bridges that tie together functional groups of two different molecules, e.g., a stabilizing and coagulating agent. However, it is contemplated that dimers or multimers of the same analog can be made or that heteromeric complexes comprised of different analogs can be created. To link two different compounds in a step-wise manner, hetero-bifunctional cross-linkers can be used that eliminate unwanted homopolymer formation.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single-chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

IV. Cell Separation Techniques

Methods of separating cell populations and cellular subsets are well known in the art and may be applied to the cell populations of the present invention. Cells purified in this fashion may then be used for stimulation and cell replacement therapy, such as in tissue regeneration purposes. Embryonic stem cells, as well as stem cells for neuronal, endothelial, cardiac and other cell types are believed by the inventors to be useful in accordance with the present invention. Stimulating those stem cells from a quiescent condition with compounds of the present invention should promote differentiation. They may also be treated with particular combinations with previously known growth and differentiation factors and then cultured to expand and/or differentiate. The following description sets forth exemplary methods of separation for stem cells based upon the surface expression of various markers.

A. Fluorescence Activated Cell Sorting (FACS)

FACS facilitates the quantitation and/or separation of subpopulations of cells based upon surface markers. Cells to be sorted are first tagged with a fluorescently labeled antibody or other marker specific ligand. Generally, labeled antibodies and ligands are specific for the expression of a phenotype specific cell surface molecule. The labeled cells are then passed through a laser beam and the fluorescence intensity of each cell determined. The sorter distributes the positive and negative cells into label-plus and label-minus wells at a flow rate of approximately 3000 cells per second.

The use of multiple fluorescent tags exciting at different wavelengths allows for sorting based upon multiple or alternate criteria. Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red. Thus, for example, a single PBMC sample may be analyzed with alternatively labeled anti-Ig antibody, anti-CD3 antibody, anti-CD8 antibody and anti-CD4 antibody to screen for the presence of B cells and T cells within the sample, as well as distinguishing specific T cell subsets.

FACS analysis and cell sorting is carried out on a flow cytometer. A flow cytometer generally consists of a light source, normally a laser, collection optics, electronics and a computer to translate signals to data. Scattered and emitted fluorescent light is collected by two lenses (one positioned in front of the light source and one set at right angles) and by a series of optics, beam splitters and filters, which allow for specific bands of fluorescence to be measured.

Flow cytometer apparatus permit quantitative multiparameter analysis of cellular properties at rates of several thousand cells per second. These instruments provide the ability to differentiate among cell types. Data are often displayed in one-dimensional (histogram) or two-dimensional (contour plot, scatter plot) frequency distributions of measured variables. The partitioning of multiparameter data files involves consecutive use of the interactive one- or two-dimensional graphics programs.

Quantitative analysis of multiparameter flow cytometric data for rapid cell detection consists of two stages: cell class characterization and sample processing. In general, the process of cell class characterization partitions the cell feature into cells of interest and not of interest. Then, in sample processing, each cell is classified in one of the two categories according to the region in which it falls. Analysis of the class of cells is very important, as high detection performance may be expected only if an appropriate characteristic of the cells is obtained.

Not only is cell analysis performed by flow cytometry, but so too is sorting of cells. In U.S. Pat. No. 3,826,364, an apparatus is disclosed which physically separates particles, such as functionally different cell types. In this machine, a laser provides illumination which is focused on the stream of particles by a suitable lens or lens system so that there is highly localized scatter from the particles therein. In addition, high intensity source illumination is directed onto the stream of particles for the excitation of fluorescent particles in the stream. Certain particles in the stream may be selectively charged and then separated by deflecting them into designated receptacles. A classic form of this separation is via fluorescent tagged antibodies, which are used to mark one or more cell types for separation.

Additional and alternate methods for performing flow cytometry and fluorescent antibody cell sorting are described in U.S. Pat. Nos. 4,284,412; 4,989,977; 4,498,766; 5,478,722; 4,857,451; 4,774,189; 4,767,206; 4,714,682; 5,160,974; and 4,661,913, herein expressly incorporated by reference.

B. Micro-Bead Separation

Cells in suspension may be separated to very high purity according to their surface antigens using micro-bead technologies. The basic concept in micro-bead separations is to selectively bind the biomaterial of interest (e.g., a specific cell, protein, or DNA sequence) to a particle and then separate it from its surrounding matrix. Micro-bead separation involves contacting a cell suspension with a slurry of micro-beads labeled with a cell surface specific antibody or ligand. Cells labeled with the micro-beads are then separated using an affinity capture method specific for some property of the beads. This format facilitates both positive and negative selection.

Magnetic beads are uniform, superparamagnetic beads generally coated with an affinity tag such as recombinant streptavidin that will bind biotinylated immunoglobulins, or other biotinylated molecules such as, for example, peptides/proteins or lectins. Magnetic beads are generally uniform micro- or nanoparticles of $Fe_3O_4$. These particles are superparamagnetic, meaning that they are attracted to a magnetic field but retain no residual magnetism after the field is removed. Suspended superparamagnetic particles tagged to a cell of interest can be removed from a matrix using a magnetic field, but they do not agglomerate (i.e., they stay suspended) after removal of the field.

A common format for separations involving superparamagnetic nanoparticles is to disperse the beads within the pores of larger microparticles. These microparticles are coated with a monoclonal antibody for a cell-surface antigen. The antibody-tagged, superparamagnetic microparticles are then introduced into a cellular suspension. The particles bind to cells expressing the surface antigen of interest and maybe separated out with the application of a magnetic field. This may be facilitated by running the suspension over a high gradient magnetic separation column placed in a strong magnetic field. The magnetically labeled cells are retained in the column while non-labeled cells pass through. When the column is removed from the magnetic field, the magnetically retained cells are eluted. Both, labeled and non-labeled fractions can be completely recovered.

C. Affinity Chromatography

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed elsewhere in this document.

V. Stem/Progenitor/Differentiated Cell Culture

Cell culture facilitates the maintenance and propagation of cells in vitro under controlled conditions. Cells may be cultured in a variety of types of vessels constructed of, for example, glass or plastic. The surfaces of culture vessels may be pre-treated or coated with, for example, collagen, polylysine, or components of the extracellular matrix, to facilitate the cellular adherence. Some sophisticated techniques utilize entire layers of adherent cells, feeder cells, which are used to support the growth of cells with more demanding growth requirements.

Cells are normally cultured under conditions designed to closely mimic those observed in vivo. In order to mimic the normal physiological environment cells are generally incubated in a $CO_2$ atmosphere with semi-synthetic growth media. Culture media is buffered and contains, among other things, amino acids, nucleotides, salts, vitamins, and also a supplement of serum such as fetal calf serum (FCS) horse serum or even human serum. Culture media may be further supplemented with growth factors and inhibitors such as hormones, transferrin, insulin, selenium, and attachment factors.

As a rule, cells grown in vitro do not organize themselves into tissues. Instead, cultured cells grow as monolayers (or in some instances as multilayers) on the surface of tissue culture dishes. The cells usually multiply until they come into contact with each other to form a monolayer and stop growing when they come into contact with each other due to contact inhibition.

Anchorage-dependent cells show the phenomenon of adherence, i.e., they grow and multiply only if attached to the inert surface of a culture dish or another suitable support. Such cells cannot normally be grown without a solid support. Many cells do not require this solid surface and show a phenomenon known as Anchorage-independent growth. Accordingly, one variant of growing these cells in culture is the use of Spinner cultures or suspension cultures in which single cells float freely in the medium and are maintained in suspension by constant stirring or agitation. This technique is particularly useful for growing large amounts of cells in batch cultures.

Anchorage-independent cells are usually capable of forming colonies in semisolid media. Some techniques have been developed that can be used also to grow anchorage-dependent cells in spinner cultures. They make use of microscopically small positively-charged dextran beads to which these cells can attach.

The starting material for the establishment of a cell culture typically is tissue from a suitable donor obtained under sterile conditions. The tissues may be minced and treated with proteolytic enzymes such as trypsin, collagenase of dispase to obtain a single cell suspension that can be used to inoculate a culture dish. In some cases dispersion of tissue is also effectively achieved by treatment with buffers containing EDTA. A particular form of initiating a cell culture is the use of tiny pieces of tissues from which cells may grow out in vitro.

Primary cell cultures maintained for several passages may undergo a crisis. Ascrisis is usually associated with alterations of the properties of the cells and may proceed quickly or extend over many passages. Loss of contact inhibition is frequently an indication of cells having lost their normal characteristics. These cells then grow as multilayers in tissue culture dishes. The most pronounced feature of abnormal cells is the alteration in chromosome numbers, with many cells surviving this process being aneuploid. The switch to abnormal chromosome numbers is usually referred to as cell transformation and this process may give rise to cells that can then be cultivated for indefinite periods of time by serial passaging. Transformed cells give rise to continuous cell lines.

In certain aspects of the instant invention, cells are cultured prior to contact with differentiating agents. They may also be cultured after contact, i.e., after they have been induced to differentiate toward a given or specific phenotype. Cells will be cultured under specified conditions to achieve particular types of differentiation, and provided various factors necessary to facilitate the desired differentiation.

VI. Stimulatory Factors

A. Cell Growth and Differentiation Factors

Cell growth and differentiation factors are molecules that stimulate cells to proliferate and/or promote differentiation of cell types into functionally mature forms. In some embodiments of the invention, cell growth and differentiation factors may be administered in combination with compounds of the present invention in order to direct the administered cells to proliferate and differentiate in a specific manner. One of ordinary skill would recognize that the various factors may be administered prior to, concurrently with, or subsequent to the administration of compounds of the present invention. In addition, administration of the growth and/or differentiation factors may be repeated as needed.

It is envisioned that a growth and/or differentiation factor may constitute a hormone, cytokine, hematapoietin, colony stimulating factor, interleukin, interferon, growth factor, other endocrine factor or combination thereof that act as intercellular mediators. Examples of such intercellular mediators are lymphokines, monokines, growth factors and traditional polypeptide hormones. Included among the growth factors are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factors-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte/macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; IL-13, IL-14, IL-15, IL-16, IL-17, IL-18. As used herein, the term growth and/or differentiation factors include proteins from natural sources or from recombinant cell culture and biologically active equivalents of the native sequence, including synthetic molecules and mimetics.

B. Post-Stimulation Purification of Induced Cells

Following stimulation, it may be desirable to isolate stem cells that have been induced to undergo differentiation from those that have not. As discuss above, a variety of purification procedures may be applied to cells to effect their separation, and a number of these rely on cell surface markers.

i. Cardiomyocytes

U.S. Patent Publication No. 2005/0164382, incorporated herein by reference, describes methods of obtaining cardiomyoctyes as well as various cardiomyocyte markers including cTnI, cTNT, ventricular myosin, connexin43, sarcomeric myosin heavy chain (MHC), GATA-4, Nkx2.5, N-cadherin, P1-adrenoceptor (β1-AR), ANF, MEF-2A, MEF-2B MEF-2C, MEF-2D creatine kinase MB (CK-MB), myoglobin, or atrial natriuretic factor (ANF).

ii. Neuronal Cells

A number of neuronal markers have been used to identify various classes of cells that are of neuronal origin. For example, glial fibrillary acidic protein and S100 protein are used to identify astrocytes, GAP-43, microtubule associated protein 2 neuronal specific enolase, synaptophysin, tryptophan hydroxylase, β-tubulin and vimentin/LN6 are used to identify neuronal cells generally, and myelin basis protein can be used to identify oligoodendrocytes.

VII. Methods of Treatment

The present invention contemplates a variety of uses for the compounds of the present invention. In particular, they can be used to treat individuals that have undergone trauma, injury, disease or other destruction or damage to cardiac or neuronal tissue. In particular, the invention is directed to the treatment of damaged heart muscle in the context of cardiac hypertrophy, myocardial ischemia and cardiac failure.

In one embodiment, the invention contemplates the administration of the compounds directly into an affected subject. Traditional routes and modes of administration may be utilized depending the clinical situation and the tissue target of the therapy. Alternatively, the invention may rely on an ex vivo approach, where stem cells are stimulated with compounds of the present invention outside an organism and then administered, optionally after culturing to expand the cells, to a recipient. The cells may be heterologous to the recipient, or they may have previously been obtained from that recipient, i.e. autologous.

In another embodiment, the present invention contemplates the use of compounds of the present invention to induce differentiation in cells that have become pathologically de-differentiated, i.e., hyper- or neoplastic cells, such as cancer cells. Particular embodiments of this aspect of the invention involved the treatment of individuals have neuronal cancers, such as gliomas and glioblastomas, including glioblastoma multiforme.

VIII. Pharmaceutical Compositions

It is envisioned that, for administration to a host, compounds of the present invention and stimulated/differentiated cells will be suspended in a formulation suitable for administration to a host. Aqueous compositions of the present invention comprise an effective amount of a compound and/or cells dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

Compounds and/or cells for administration will generally be formulated for parenteral administration, e.g., formulated for injection via the intravenous, intramuscular, sub-cutaneous, intralesional, or even intraperitoneal routes. The preparation of an aqueous composition that contains cells as a viable component or ingredient will be known to those of skill in the art in light of the present disclosure. In all cases the form should be sterile and must be fluid to the extent that easy syringability exists and that viability of the cells is maintained. It is generally contemplated that the majority of culture media will be removed from cells prior to administration.

Generally, dispersions are prepared by incorporating the compounds and cells into a sterile vehicle which contains the basic dispersion medium and the required other ingredients for maintaining cell viability as well as potentially additional components to effect proliferation, differentiation or replacement/grafting in vivo. Upon formulation, solutions will be administered in a manner compatible with the dosage formulation or in such amount as is therapeutically effective. Some variation in dosage will necessarily occur depending on the condition of the subject being treated. The person responsible for administration will, in any event, determine the appropriate dose for the individual subject.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Chemical libraries and medicinal chemistry. The UTSW compound library used in this screen was purchased in two components, 47,000 unique compounds selected from the DiverSet™ small-molecules library (ChemBridge, Inc; San Diego, Calif.), 100,000 unique compounds from Chemical Diversity Labs, Inc. (San Diego, Calif.). This collection of compounds was additionally filtered to exclude compounds containing reactive groups and compounds likely to be insoluble or cytotoxic.

Assay development. An Nkx2.5-luc transgene was constructed by replacing the two coding sequence exons of Nkx2.5 locus from the ATG with the coding sequence of luc (from pGL3-basic vector, Promega) in an ~180,000 base pair-long BAC (FIG. 1A). The recombinant BAC DNA was introduced into pluripotent P19CL6 cells using Lipofectamine-2000 (Invitrogen) and neo$^R$ clones were selected, and tested for chemically inducible luc activity with sodium butyrate (NaB). #5-1, a clonal stem cell line with low basal and at least a 4-fold higher NaB-inducible luciferase activity compared to vehicle control (DMSO), yielding a Z' value of ~0.7 in 384-well plate format (Zhang et al. 1999), was chosen for the HTS.

HTS for chemical inducers of Nkx2.5-luc in P19CL6. Approximately 147,000 unique compounds were screened using clone #5-1 P19CL6 Nkx2.5-luc cells in 384-well white plates. To ensure pluripotency at the time of compound screening, each P19CL6 #5-1 cell batch was pre-screened for uniform high-level Oct3/4 expression by immunofluorescence cell staining Cells were plated using an automated dispenser at 1,200 cells/well in 70 μl media/well in 10% fetal calf-serum MEMα media. Parallel plating onto clear-bottom plates was done to ensure the viability and appropriate cell density for large-scale screens. On day 3, 0.7 μl of library compounds at 5 μM in pure DMSO (1% final DMSO concentration) was dispersed robotically (384-pin array Biomek FX high-precision robot) and the plates were incubated for an additional 48 hrs before measuring luciferase activity.

Primary and secondary screening hit selection. Screening the entire 147,000 UTSW compound library at 5 μM with clone #5-1 reporter cells resulted in ~3,000 primary "hits," using a luc activity of >2 times the plate median as the cut-off for positive score. Secondary screening using #5-1 cells at 1.7, 5, and 15 μM, identified 66% of these hits as repeat positives, and from these positive hits, the inventors placed 150 compounds with the best dose response into a candidate hit list. Among these candidates, 10 major sub-groups with common core structural motifs emerged (Table 4). Computer-based chemo-informatic analysis of the library and the positive hits from the screen, as well as the negative ones, revealed that, (e.g., although there were four positive Shz hits) (FIG. 11), there were also more than 30 structurally-related Shzs in the library that were negative in the primary screen.

TABLE 4

Top-10 Hit List

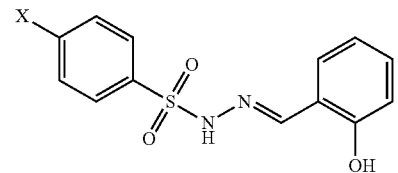

Biaryl sulfonyl-hydrazones
(N = 4)

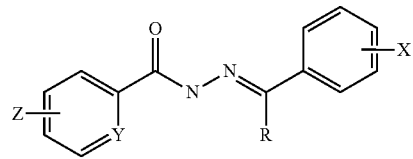

Y = N, CH
Biaryl acyl-hydrazones
(N = 6)

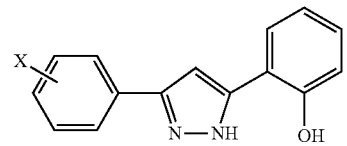

3,5-disubstituted
pyrazoles (N = 4)

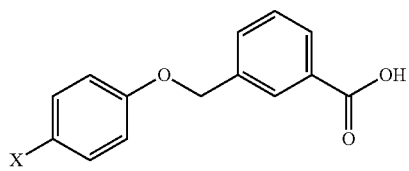

Aryl ether benzoic acids
(N = 6)

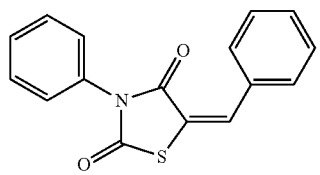

Thiazolidinediones (N = 2)

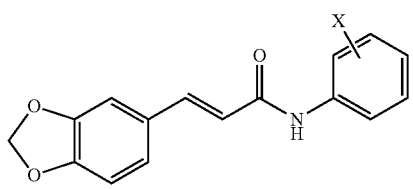

(Cinnamic amides (= 2)

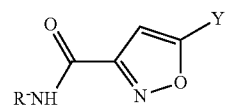

3,5-disubstituted
isoxazoles (N = 5)

TABLE 4-continued

Top-10 Hit List

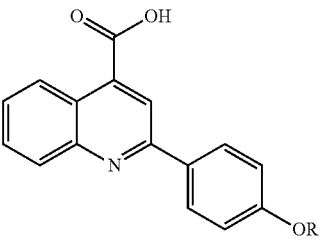

Quinolinecarboxylic acids
(N = 3)

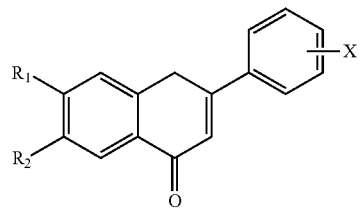

Flavonoids
(N = 3)

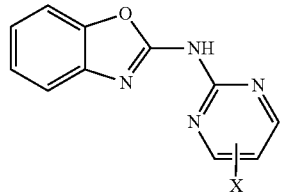

2-Aminobenzoxazoles
(N = 2)

Each of these compound families was independently identified multiple times in the primary screen using Nkx2.5-luc P19CL6 cells, and then re-identified in a secondary, confirmatory screen using the same reporter cells. X, Y, R, $R_1$, $R_2$ are additional chemical side groups.

Reporter gene assays. All reporter gene assays were done in a 96-well format, and each data point represents the average of 12 replicates, with 5,000 cells/well in a volume of 200 µL. Cos and P19CL6 cells were transfected using Lipofectamine-2000 and serial dilutions of compound were added the day following transfection and luc assays performed two days later.

Pre-treatment of M-PBMCs and rat cryoinjury model. Human M-PBMCs cells were cultured in X-vivo 20 media with Shz at 2.5 or 5 µM or vehicle (vol./vol. equivalent DMSO control) for three days, then washed and resuspended in fresh X-vivo 20 media for an additional 7 days. The cells were either harvested in Trizol (Invitrogen) for RNA isolation, washed with PBS and fixed on chamber slides for immunohistochemistry, or trypsinized (0.05% trypsin) and counted for in vivo delivery. Athymic nude rats (8-10 weeks) (Harland) lacking cell-mediated immunity were utilized to minimize rejection of the human cells.

PCR amplication and sequencing of human cDNAs from rat chimeric hearts. High-stringency PCR conditions to enrich for human-specific cDNAs in rat chimeric hearts were as follows: Nkx2.5 (94° C.×3 min, 94° C.×15 sec, 65° C.×30 sec, 72° C.×15 sec, 72×3 min, 40 cycles) and cTnI (94° C.×3 min, 94° C.×15 sec, 63° C.×15 sec, 72° C.×15 sec, 72° C.×3 min, 40 cycles). Following PCR for human Nkx2.5 and cTnI cDNAs, bands were excised and DNA was recovered and ligated to a TA cloning vector (pCR2.1 TOPO vector) (Invitrogen). Bacterial clones containing presumptive human cDNA inserts were subject to a second round of PCR amplification using M13 forward and reverse primers contained within the TOPO vector. For both Nkx2.5 and cTnI, >50 random clones were picked and sequenced. On average, ~1/25 clones contained the human sequence and ~24/25 clones were either vector or rat sequence. Statistics. Statistical analysis was carried out using Microsoft Excel. The unpaired two-tailed Student's t-test was used to generate P-values for all datasets. All error bars are expressed as standard error of the mean.

Cell culture. P19CL6 is a sub-line of P 19EC cells, originally generated by. Habara-Ohkubo (1996), and were grown in MEMα containing 10% fetal calf serum and antibiotics. H9c2 cells were grown in DMEM containing 10% fetal calf serum and antibiotics. SM1 ES cells are grown in standard mouse ES cell media (DMEM with 20% fetal bovine serum, LIF, β-mercaptoethanol, antibiotics, nucleosides, amino acids and glutamine) on irradiated SNL-STO mouse feeder cells. LIF and feeder cells were removed from the culture system for ES cell differentiation experiments. To obtain M-PBMCs, apheresis blood was obtained from normal human bone marrow transplantation donors, consented by the blood bank to contribute extra cells for research purposes, following conventional GCSF mobilization (Carter Blood Bank, Dallas, Tex.), and all cells were used within 24 hrs of collection. M-PBMCs were isolated by ficoll gradient centrifugation (Ficoll-Paque, Amersham Pharmacia Biotech), washed and counted following RBC lysis using ammonium chloride lysis solution (150 mM $NH_4Cl$, 10 mM $KHCO_3$ and 0.1 mM EDTA), then re-suspended in X-vivo 20, serum-free media (BioWhittaker/Lonza, Wakersville, Md.), at high cell density ($2 \times 10^6$ cells/ml). For in vivo experiments, the cells were labeled with 4',6-diamidino-2-phenylindole (DAPI, 100 µM) overnight and cellular viability (consistently >95%) was confirmed by Trypan Blue exclusion.

Total RNA extraction, cDNA preparation, and real time RT-PCR. Trizol reagent RNA preparation (Invitrogen) and cDNA synthesis with the SuperScript II kit, were used following manufacturer's protocol (Invitrogen). For real-time reverse transcriptase (RT) PCR, reactions were carried out essentially as described (Zhao et al., 2001). The relative amount of the tested message was normalized to the level of the internal control message, GAPDH. Primer sequences are available upon request.

Immunohistochemical cell staining and protein blotting. Cells were fixed with 4% paraformaldehyde, followed by immunohistochemical (IHC) staining as described (Hshieh et al., 2004). Labeled cells were visualized using a Nikon TE2000-U inverted microscope (Nikon, Inc.) and a CoolSnap digital camera (Photometrics, Inc.). DAPI nuclear stain was used to identify individual cells. The following primary antibodies were used for cell/tissue staining: Anti-Luciferase pAb (L-0159, Sigma), α-actinin (clone EA-53, Sigma), Nkx2.5 (H-114, rabbit pAb, Santa Cruz), sarcomeric α-tropomyosin (CH1 mAb; Iowa Hybridoma Bank), GATA4 (H-112, rabbit pAb, Santa Cruz), Oct3/4 (C-10, mAb, Santa Cruz), MEF2A (C-21, Santa Cruz), and human cardiac TnI (mAb, T8665-16C, USBiological). Secondary antibodies (Jackson ImmunoResearch) were routinely used at 1:250 dilution. For protein blots, lysates were prepared from P19CL6 or H9c2 cells using RIPA buffer (Tris-Hcl, 50 mM, pH 7.4; NP-40, 1%; Na-deoxycholate, 0.25%; NaCl, 150 mM; EDTA, 1 mM; PMSF, 1 mM; Aprotinin, leupeptin, pepstatin, 1 μg/ml; Na₃VO₄, 1 mM; NaF, 1 mM). Protein concentration in centrifugation-clarified cell lysates was measured by (BCA Protein Assay Kit, Pierce) and equal amounts of protein were separated on a 4-12% SDS-PAGE and transferred to Hybond PVDF (Amersham Biosciences). Protein blots utilized the Novex MiniCell gel system with 4-20% Tris-Glycine gels (Invitrogen) and Hoeffer Semi-Phor transfer method (Pharmacia Biotech). Primary Abs for protein blotting included: sarcomeric α-tropomyosin (CH1 mAb; Iowa Hybridoma Bank), GAPDH (mAb 374, Chemicon), Phospho-Smad 1/5/8 (Cell Signaling), Phospho-ERK1/2 (Thr 202/204) (Cell Signaling); β-Catenin (E-5, mAb, Santa Cruz); Oct3/4 (C-10, mAb, Santa Cruz), Phospho-Elk (Cell Signaling), Phospho-Mek (Cell Signaling), Phospho-Raf1 (Cell Signaling). Immunoreactive bands were visualized using HRP- or AP-conjugated secondary antibodies, followed by ECL (Amersham Biosciences) or BCIP/NBT detection (KPL, Gaithersburg, Md.).

Rat cryoinjury model. Baseline left ventricular fractional shortening (FS) was obtained in un-anesthetized rats using a Vivid7 Pro echocardiography machine equipped with an 11 mHz transducer (GE). Fractional shortening was calculated from M-mode echocardiographic images by measuring left ventricular end diastolic dimension (LVEDD) and left ventricular end systolic dimension (LVESD) as follows: FS=LVEDD-LVESD]/LVEDD-100. On the day prior to scheduled cryoablative surgery, DAPI-stained human PBMCs were washed, counted and resuspended in X-vivo 20. Rats were anesthetized in an airtight chamber using 5% isofluorane, endotracheally intubated, and ventilated using a volume controlled ventilator with 100% O₂, supplemented with 2% vaporized isofluorane (Harvard Apparatus). Following lateral thoracotomy and pericardiectomy, myocardial injury was induced using a liquid nitrogen super-cooled probe applied for 10 seconds to the mid anterior free wall of the left ventricle. Five minutes following cryoinjury, human cells were injected into the healthy myocardium at three sites adjacent to the well-demarcated cryo-injury zone. Each site received 15 μL of cells (~30,000 cells) using a 30-gauge needle equipped with a protective sleeve to prevent inadvertent injection of the cells into the ventricular cavity, bringing the total number of cells injected per animal to 9–10×10⁴. Serial left ventricular functional assessment (fractional shortening) was then carried out in un-anesthetized animals at days 3, 7, 14, and 21, by investigators blinded to whether animals had received drug-treated or control cells. Rat hearts were harvested following CO₂ inhalation euthanasia. The hearts were either rapidly frozen in liquid nitrogen and stored at −80° C. for RNA isolation, or fixed with 4% PFA and paraffin embedded for IHC.

Example 2

Results

Figure 6B:
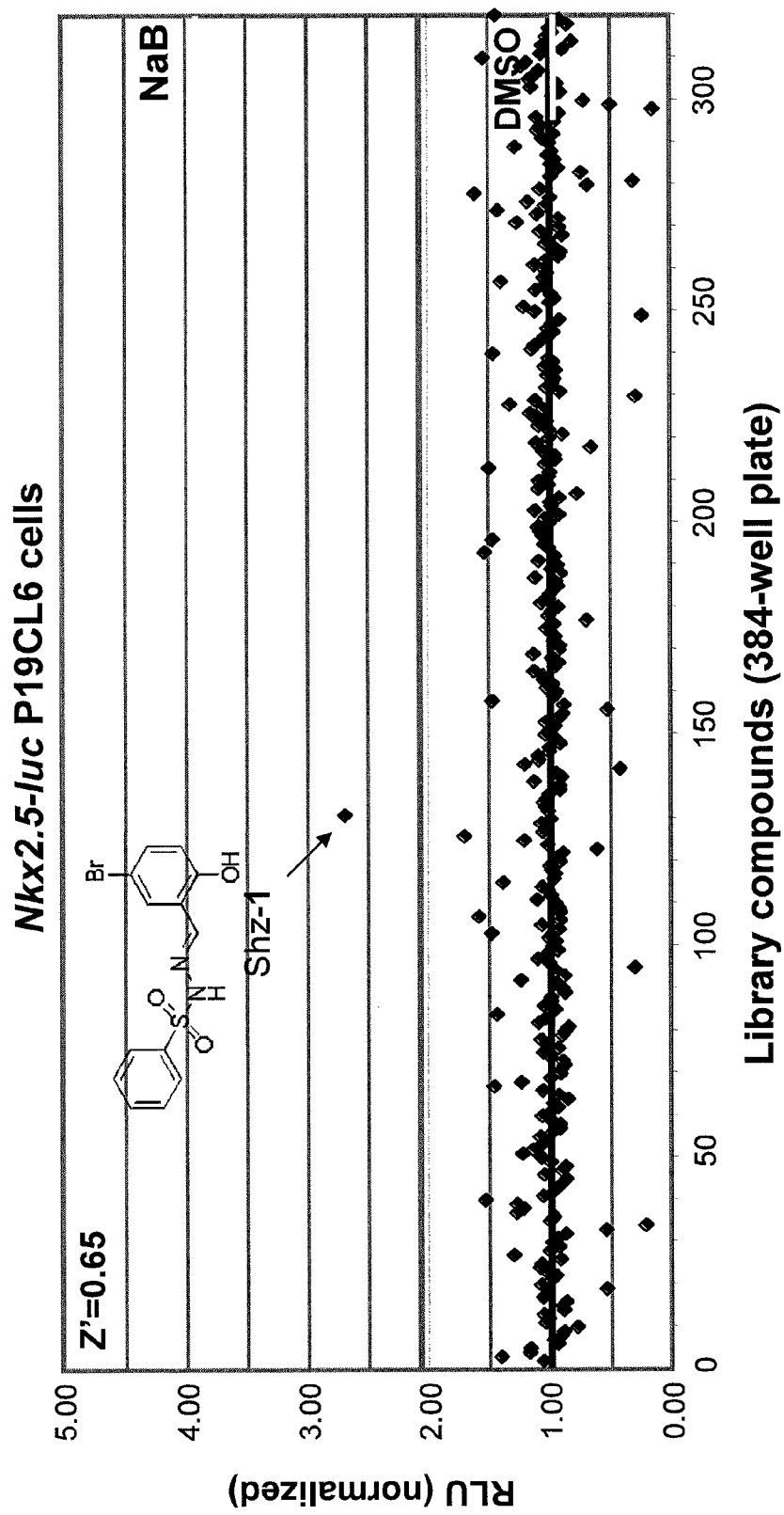
Figure 7:
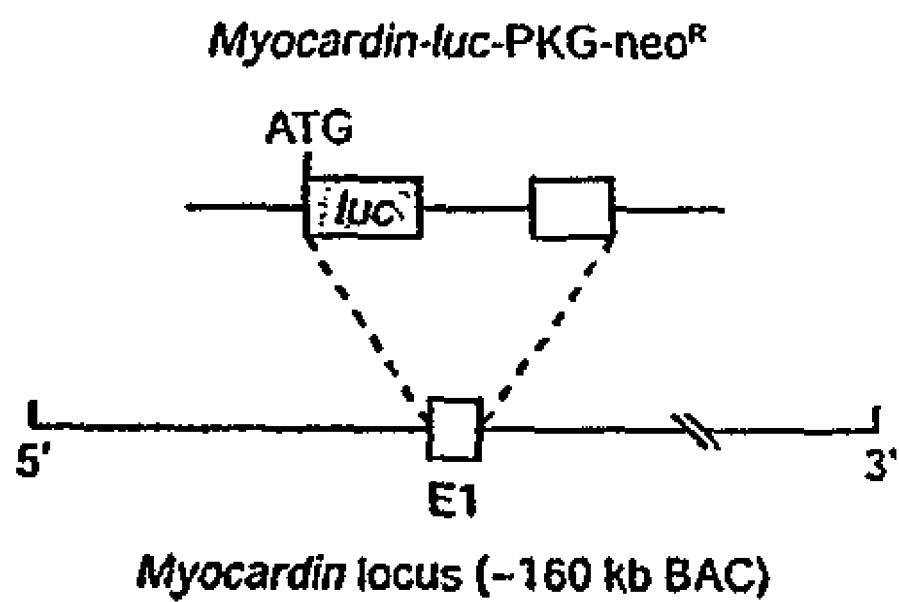
FIG. 7—Schematic of reporter transgene with luciferase inserted by homologous recombination into the myocardin locus on an ~160 kb mouse BAC.

Cardiogenic small-molecule screen. To identify cardiogenic small-molecules, the inventors screened ~147,000 compounds in the UTSW chemical library for activators of the firefly luciferase gene (luc), inserted by homologous recombination (*E. coli* recombineering) into the Nkx2.5 locus on a 180-kilobase mouse BAC (FIG. 1A), stably integrated into the genome of P19 mouse pluripotent embryonal carcinoma cells, sub-clone CL6 (P19CL6) (Habara-Ohkubo, 1996). The inventors confirmed that the expression pattern of this recombinant Nkx2.5-luc BAC faithfully mirrored the endogenous gene by generating transgenic mice, which had luc activity exclusively in adult myocardium using bioluminescence and biochemical assay (FIG. 1B and FIG. 6A). The positive control compound for the Nkx2.5-luc BAC P 19CL6 reporter cells was the histone deacetylase (HDAC) inhibitor, sodium butyrate (NaB), which strongly and reliably activated this transgene, demonstrated by luciferase immunostaining (FIG. 1C) and in high throughput mode luc assay (FIG. 6B, green line). NaB also activated expression of the endogenous Nkx2.5 locus in P19CL6 cells, demonstrated by real-time RT-PCR for Nkx2.5 transcripts (FIG. 1D) and by immunohistochemistry (IHC) for NKX2.5 protein (FIG. 1E). Indeed, NaB efficiently produced spontaneously beating cardiomyocytes in P19CL6 cell cultures (data not shown), and thus could serve as a positive control for the cardiogenic small-molecule in this assay. Importantly, dimethyl sulfoxide (DMSO)—the solvent for the chemical library compounds—at vehicle concentration and brief exposure time for the primary screen (1.0% vol./vol.) did not induce the Nkx2.5-luc BAC reporter above background levels (FIG. 6B, yellow line). The strongest positive hits from the primary screen were selected and re-screened using a dose response strategy, and more than one half of these candidates remained firmly positive. Using chemo-informatics, the inventors clustered these hits into a list of families with chemically distinctive and synthetically tractable core structural motifs (Table 4, above). The diversity of chemical structures among this list, ranged from thiazolidinediones to flavonoids, implies that multiple unique proteins or biochemical reactions involved in Nkx2.5 gene regulation and/or cardiac fate were successfully targeted in this small-molecule screen.

Validation of sulfonyl-hydrazone hits. As a starting point, the inventors chose to explore the Shz small-molecule family, one of the most promising leads in this hit collection, in greater detail. Of note, this screen had independently identified four structurally distinct biologically active Shz small-molecules, and, equally important, many biologically inactive variants, a few of which are shown (FIG. 11). To re-synthesize library compounds or create new Shz variants for structure-activity relationship studies, substituted benzenesulfonyl hydrazides were condensed with an aromatic aldehyde, and isolated as pure crystalline compounds whose structures were verified using NMR and mass spectrometry (FIG. 11). The sulfonyl hydrazone molecules used in this study are shown in (Table 5).

TABLE 5

Sulfonyl-Hydrazone Compounds Used

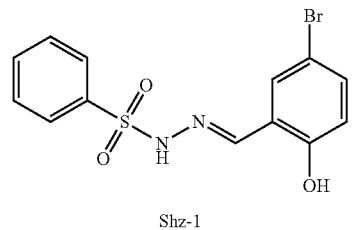

Shz-1

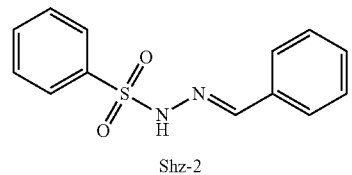

Shz-2

TABLE 5-continued

Sulfonyl-Hydrazone Compounds Used

Shz-3

Shz-4

Compounds Shz-1 (#120169) and Shz-2 (#153042) were positive and negative "hits," identified in the primary screen, and compounds Shz-3 and Shz-4 were synthesized at UTSW using the organic chemical reaction shown in (FIG. 11).

The inventors first examined the cardiogenic activity of Shz small-molecules by confirming dose-dependent activation of the Nkx2.5-luc BAC transgene in P19CL6 cells (FIG. 1F). Importantly, in this reporter gene stem cell assay, Shz-1 showed peak activity at 2.5 µM. The inventors also confirmed by real time RT-PCR, with normalization against GAPDH mRNA levels, that Shz-1 specifically activated the endogenous Nkx2.5 locus in parental P19CL6 cells in a dose responsive manner (FIG. 1G). In fact, the endogenous Nkx2.5 gene in P19CL6 cells was even more responsive to Shz-1 than the BAC transgene, peaking at 1.2 or even sub-µM drug concentrations (FIG. 1G). The close correspondence of Nkx2.5 BAC and native Nkx2.5 gene behavior in P19CL6 cells, like the cardiac-specific expression of the BAC in transgenic mice, provided additional reassurance that this reporter had served as a reliable biosensor of Nkx2.5 gene activation and cardiac fate.

It was also important to confirm that Shz small-molecules did not indiscriminately activate reporter (or endogenous) genes in stem cells. Shz small-molecules failed to induce a number of reporter genes, including the CMV promoter/enhancer, in P19CL6 cells (data not shown). Shz small-molecules also demonstrated cell type-specificity insofar as they only activated an Nkx2.5-luc reporter gene, containing ~3 kb of 5' regulatory sequence, in P19CL6 and not in Cos cells (data not shown).

Figure 8:
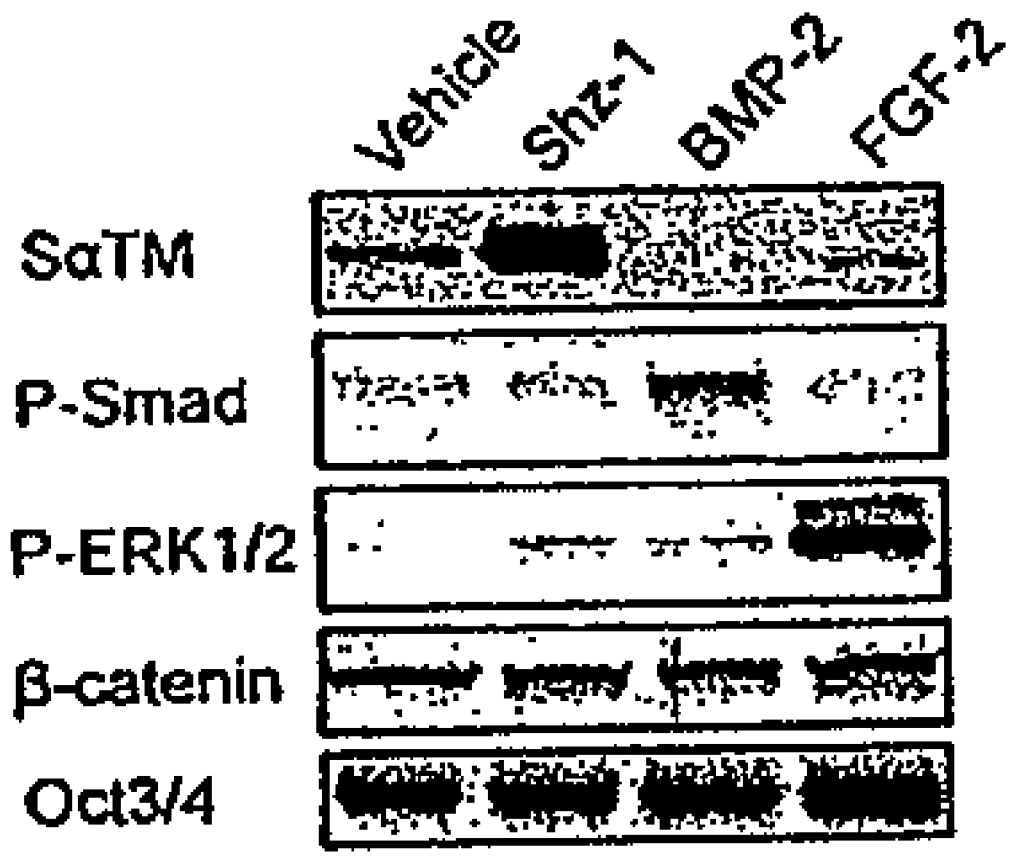
FIG. 8—P19CL6 cells were treated with vehicle, Shz-1 (2.5 µM), BMP-2 (50 ng/ml) or FGF-2 (20 ng/ml), harvested after 1 hour (P-Smad, P-ERK1/2) or 24 hours (SαTM, β-catenin, Oct3/4), and blotted with Abs as listed.

Activation of myocardin gene by Shz small-molecules. Myocardin is a serum response factor co-activator that stimulates the transcription of multiple muscle genes during cardiac and smooth muscle development, and serves as a very early marker, like Nkx2.5, of cardiac progenitor cells (Pipes et al., 2006; Creemers et al., 2006). For this reason, the inventors chose myocardin to establish a second set of stem cell reporter systems, including a myocardin-luciferase knock-in BAC (generated by E. coli recombineering) integrated as a transgene into the genome of P19CL6 cells (FIG. 8). In addition, the inventors introduced luciferase by homologous gene recombination directly into myocardin locus in the genome of SM1 mouse ES cells. For the myocardin-luc P19CL6 cells, the inventors tested Shz-3 and Shz-4 (Table 5), two of the Shz variants the inventors had designed and synthesized. Whereas Shz-3 strongly activated the myocardin-luc transgene in P19CL6 cells, Shz-4 was inactive (FIG. 2A). This result, in addition to more extensive structure-activity relationship data that will be presented elsewhere, confirmed that small changes in Shz structure could profoundly impact biological activity. Shz-1 specifically activated the myocardin-luciferase knock-in gene in SM1 ES cells (FIG. 2B). Finally, as for Nkx2.5, the inventors confirmed that Shz small-molecules activated the native myocardin gene in parental P19CL6 cells (FIG. 2C) and SM1 ES cells (FIG. 2D), using real-time RT-PCR with normalization versus GAPDH mRNA levels. Thus, like Nkx2.5, the myocardin gene could serve as a sensitive biosensor of chemical cardiogenic signaling.

The inventors also demonstrated that Shz small-molecules induced expression of the mesodermal marker, brachyury-T, by real-time RT-PCR normalized for GAPDH in SM1 mouse ES cells (FIG. 2E). The specific induction of brachyury-T in mouse ES cells suggests that Shz small-molecules also activate mesodermal genes, upstream of Nkx2.5 and myocardin in the normal developmental cascade. Taken together, these reporter gene and mRNA data establish that Shz small-molecules specifically activate brachyury-T and two key early cardiogenic program genes, Nkx2.5 and myocardin, in pluripotent mouse stem cells.

Activation of sarcomeric α-tropomyosin expression by Shz small-molecules. In stem cells, protein expression is a more robust marker of lineage-specific differentiation than mRNA, which can be promiscuously expressed and detected by methods that introduce amplification bias. The inventors observed that sarcomeric α-tropomyosin (SαTM), a highly specific protein marker of striated muscle cells and a very early marker of stem cell cardiogenesis (Muthuchamy et al., 1993), was strongly induced by Shz small-molecules in P19CL6 cells. Staining with the CH1 SαTM-specific mAb identified large clusters of cardiac progenitor cells, found exclusively in Shz small molecule-treated cultures (FIG. 2F). The absence of multi-nucleated myotubes or MyoD immunostaining, and differentiation in high serum media, argued against these Shz small-molecule induced SαTM positive clusters being skeletal muscle-derivatives, a formal possibility with the CH1 mAb (data not shown). The inventors confirmed induction of SαTM in P19CL6 cells by protein blotting (FIG. 2G and FIG. 8), and, again, like the stem cell reporter and mRNA assays, Shz-1 activity was already maximal at 2.5 µM. Of note, the inventors also observed a rapid and robust induction of SαTM in H9c2 cells, a continuous cell line derived from the embryonic rat ventricular myocardium that has selected features of a cardiac progenitor cell (FIGS. 12A-B). Indeed, in response to Shz small-molecules, SαTM positive H9c2 cells acquired a cellular morphology strikingly reminiscent of binucleated cardiomyocytes from the newborn rat heart (FIG. 12A). Shz-specific induction of SαTM in H9c2 cells was also confirmed by protein blotting (FIG. 12B).

Collectively, these gene expression studies establish that Shz small-molecules can potently activate an important subset of early cardiac genes and phenotypic differentiation in pluripotent stem cells, providing at least an initial chemical trigger for activation of the cardiac genome and cell fate.

Chemical phenotype of sulfonyl-hydrazone induced cardiogenic progenitors. The inventors interrogated the effects of Shz drug exposure on a number of pathways by phosphoprotein blotting and found that Shz small-molecules could trigger ERK1/2 pathway (e.g., Elk, Mek, and Raf1) activation in P19CL6 (FIG. 13A) and H9c2 cells (data not shown), suggesting a possible role for MAPK signal transduction in the chemical pathway leading to the genome. The MEK inhibitor, U0126, effectively blocked ERK1/2 phosphorylation in P19CL6 cells (FIG. 13B), but had no effect upon the dose-responsive Shz small molecule-mediated activation of the Nkx2.5-luc BAC reporter in P19CL6 (FIG. 13C). Likewise, U0126 could not attenuate the ability of Shz small-molecules to induce endogenous Sα-TM protein in P19CL6 cells (data not shown). Moreover, the inventors tested whether pre-treatment with a variety of different pathway-specific inhibitors, including AG566, PD 098059, Wortmannin, Ly 294002 (see Bush et al., 2004, for full list), could attenuate the Shz-1 mediated induction of Sα-TM by protein blot, and could not find an effective inhibitor of Shz small-molecule signaling in these cells (data not shown).

Importantly, it was essential to experimentally confirm whether the mechanism of activation of Nkx2.5 or other cardiac genes by Shz small molecules involved BMP, FGF and Wnt pathways, key circuits in cardiogenic signaling. The highlights of these functional and biochemical experiments are summarized in (FIG. 3 and FIG. 8). BMP-2 induced Smad-1 phosphorylation (FIG. 8) and activated the Nkx2.5-luc BAC in these reporter stem cells (FIG. 3A), and this activation was attenuated by Noggin, the BMP antagonist. Shz-1, on the other hand, activated Nkx2.5-luc independent of Smad-1 phosphorylation (FIG. 8) and was only weakly blocked by Noggin (FIG. 3A). BMP-2 also induced GATA-4 expression in these cells, but Shz-1 did not (FIG. 3B). At one hour, FGF-2 was a much stronger activator than Shz-1 of ERK1/2 phosphorylation in P19CL6 cells, and FGF-2 also induced Oct3/4 expression in these cells, detected both by increased signal by immunostaining and protein blot (FIG. 3B and FIG. 8). In contrast to BMP-2 and FGF-2, Shz-1 alone induced Sα-TM, an early phenotypic marker of cardiomyogenesis. Finally, to interrogate whether Shz-1 activated cardiac genes by modulating Wnt signaling, the inventors performed several additional experiments. First, the inventors compared expression level of total cellular β-catenin in drug treated versus control P19CL6 cells and found no difference at 1 hr (data not shown) or 24 hrs (FIG. 8). Secondly, the inventors studied whether Shz-1 could modulate the super-TOP-flash (STF) reporter gene system in a stable reporter cell line that directly measures activity of canonical Wnt pathway. This cell line constitutively expresses Wnt3a and reports Wnt3a-mediated accumulation of β-catenin as activity of a stably transfected STF reporter gene in mouse L fibroblasts. Shzs had no effect at any dose on β-catenin accumulation or on activity of the STF reporter gene in this cell system, suggesting that the Shz mechanism does not involve Wnt signaling. Taken together, these results demonstrate that the mechanism of Shz-mediated cardiac fate signaling is distinct from BMP-2, FGF-2 and Wnts, and suggest that chemical compounds like Shz-1 and these factors may have non-redundant, even complementary, functional roles in cardiogenesis. Moreover, by excluding BMP-2, FGF-2 and Wnts, this candidate-based approach to mechanism and target discovery could now focus on other pathways.

Shz small-molecule enhancement of human M-PBMCs for myocardial repair. Although this chemical screen and initial characterization of Shz small-molecules had all been done in embryonic-type stem cells, for clinical goals and therapeutic targets, the inventors set out to extend these finding to adult stem/progenitor cells, and chose GCSF-mobilized PBMCs as the first test system. The inventors studied the effects of Shz on the growth, differentiation and survival of human M-PBMCs in a standard culture model and as a cellular inoculum in the cryo-injured rat heart. Using apheresis, the inventors collected GCSF-mobilized PBMCs from anonymous normal donors ("leftover" cells from bone marrow transplants) and cultured them in serum-free chemically-defined X-vivo 20, a cell culture media optimized to support growth/survival of human stem/progenitor cells, which are included in unfractionated PBMC population. The inventors tested cells from several donors, independently, with only minor variability in cell yield and viability. The results of several experiments yielded similar findings.

Figure 9:
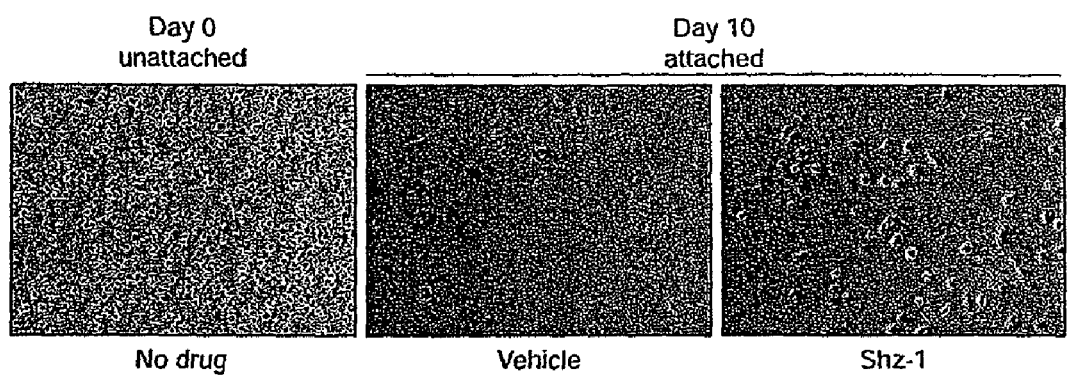
FIG. 9—Low-magnification light microscopy comparing relative attachment/survival human M-PBMCs. Timse are day zero (left panel), day 10 with vehicle for first 3 days (middle panel) or day 10 with Shz-1 (10 µM) for first 3 days (right panel). Scale bar=25 µm.

PBMCs from the circulation attach, poorly, if at all, to tissue culture dishes. Yet, when M-PBMCs were treated for the first three days following harvest with escalating concentrations of Shz-1, the inventors observed a dose-response increase in the number of cells that stably attached to the plate (FIG. 4A and FIG. 9). In contrast to drug treated cells, few cells attached in vehicle control experiments, even starting from high-density cultures (FIG. 9). The differential cell attachment in response to drug exposure was quantitated by counting the number of typical cells in at least ten representative low power fields (lpf) and then averaging these numbers (FIG. 4B). Initially, the inventors observed little proliferation of these cells; a 24-hour pulse of bromodeoxyuridine on day 9 to mark DNA synthesis demonstrated only rare BrdU-positive cells (data not shown). On the other hand, after several weeks in culture in X-vivo 20 without additional additives, the inventors did observe limited proliferation of Shz-1 treated human M-PBMCs, with the formation of very small cell colonies (data not shown). Therefore, Shz-1 primarily enhanced the attachment and survival rather than the proliferation of a pre-existing cell population in cultured human M-PBMCs.

Shz-1 treated human M-PBMCs also specifically expressed several cardiac marker mRNAs and proteins, demonstrated by RT-PCR and immunostaining, with cells from several donors using several different Shz small molecules (FIGS. 4C-D, 5C, inset). In one experiment, the inventors observed specific induction of Nkx2.5 and ANP transcripts in human M-PBMCs treated for 3 days with Shz-3 then 7 days in drug-free X-vivo 20 media (FIG. 4C). In a second independent experiment, the inventors observed specific induction of cTnI transcripts in human M-PBMCs treated, using the same 3+7 day protocol, with Shz-1 (FIG. 4D). The inventors also confirmed expression of cTnI protein following Shz-1 induction in these cells by mAb staining (FIG. 5C, inset).

Figure 10:
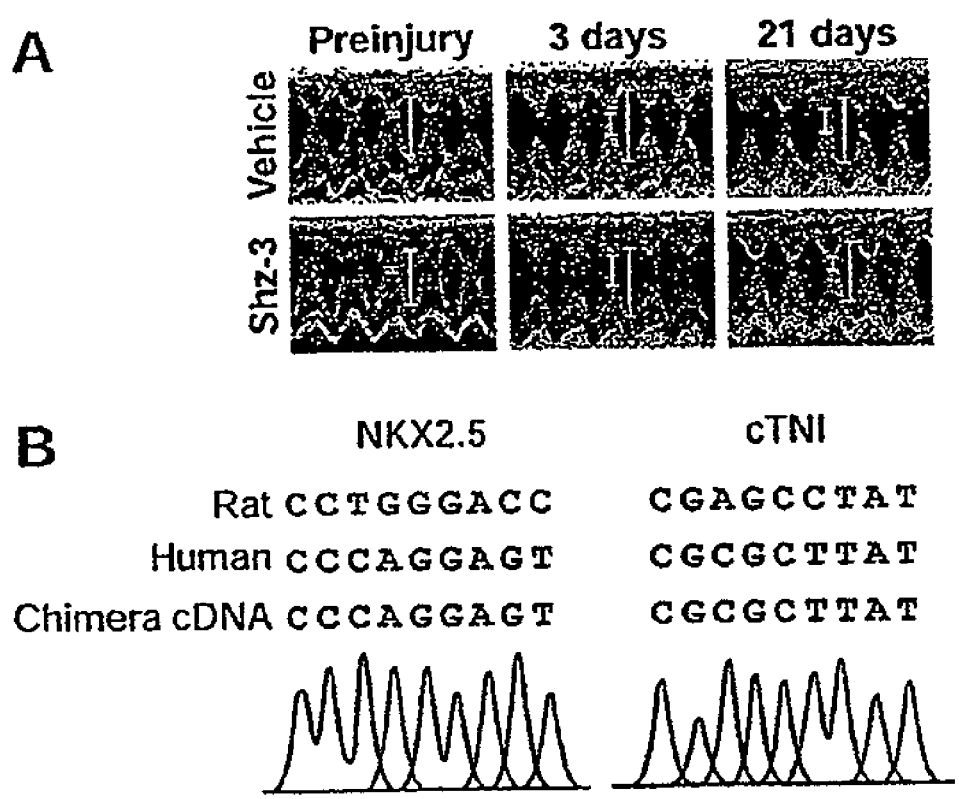
FIGS. 10A-B—(FIG. 10A) M-mode echocardiography at mid ventricle of hearts that received vehicle treated or Shz-3 treated cells. Three time points are shown: Normal awake left ventricular function (preinjury), 3 days post injury (maximum observed decline in left ventricular function), and 21 days.
Figure 14B:
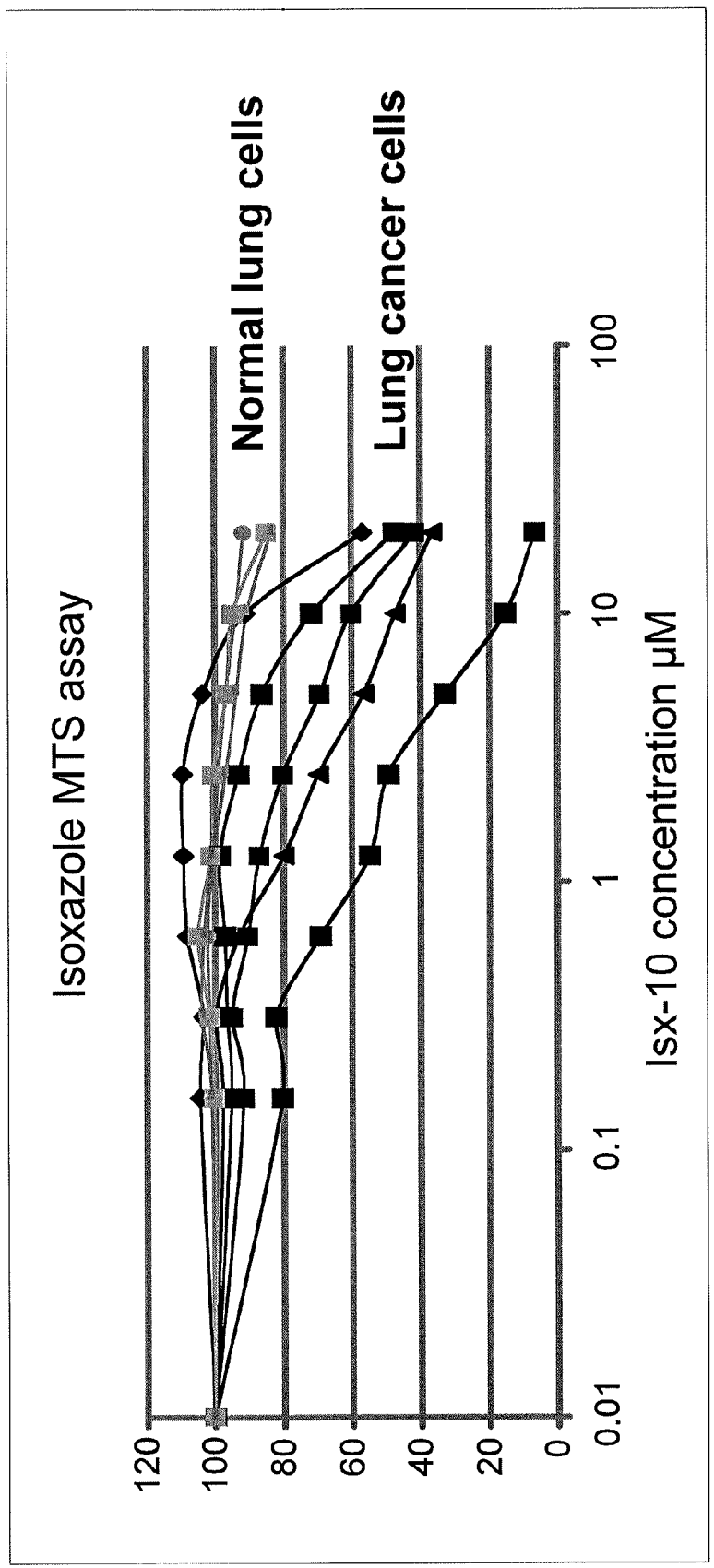
Figure 14C:
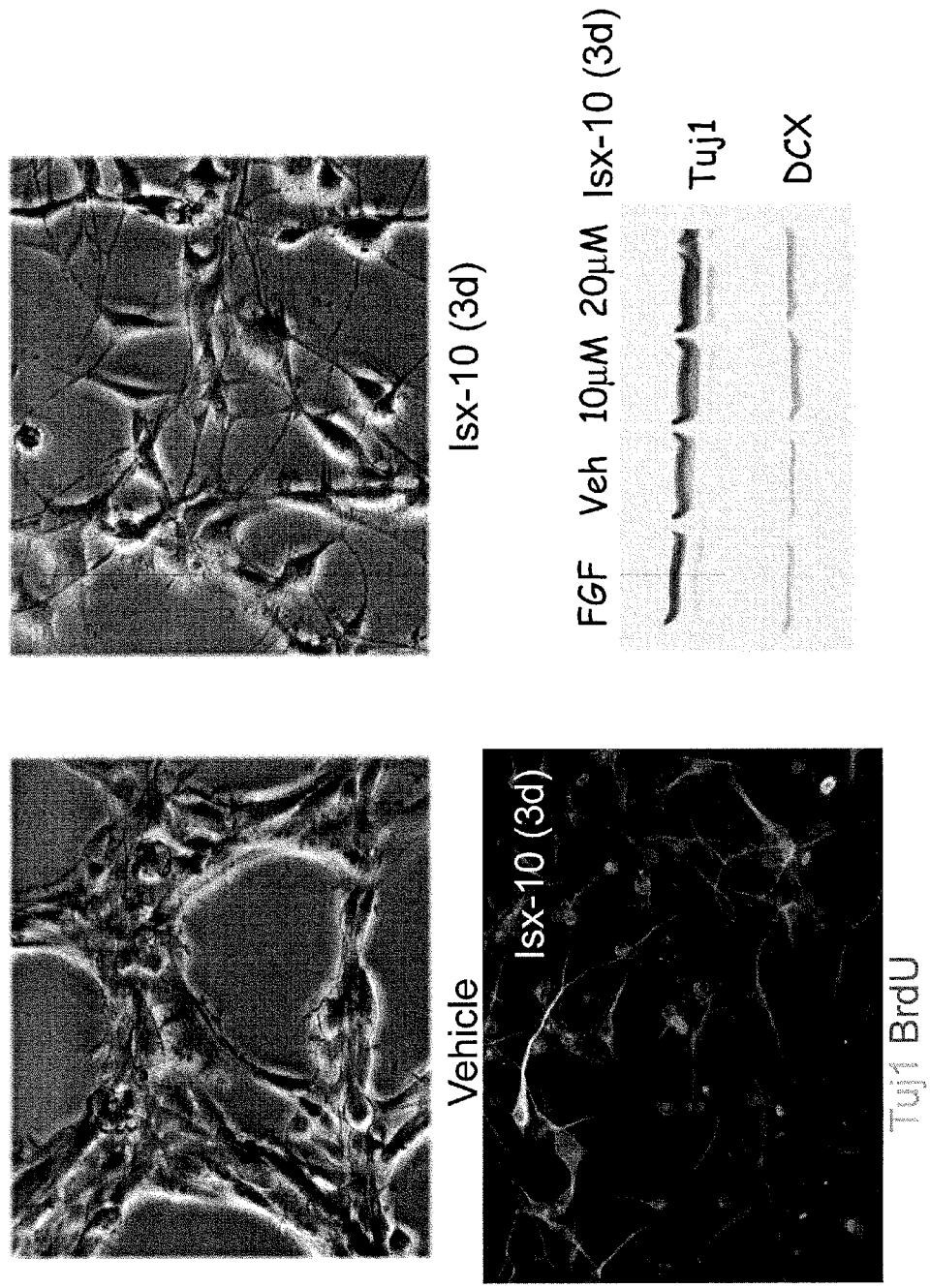

Given the attachment/differentiation/survival effects of Shz small-molecules on human M-PBMCs in vitro, the inventors tested whether drug-enhanced cells would make suitable xenografts in a rat heart cryo-injury model (FIG. 5A). Unfractionated PBMCs harvested form healthy donors following GCSF-mobilization cells were treated in vitro with Shz drug for three days. The drug was then removed and the cells cultured for an additional seven days in drug-free media (as in FIGS. 4A-D). For the final 12 hrs, cells to be used for xenograft injection were labeled with a DAPI nuclear stain, then both attached and unattached cells were harvested and assayed by Trypan Blue to assure high viability (>90%). DAPI-labeled human cells pre-treated with Shz-3 or vehicle control were then engrafted at three sites, ~30,000 cells each site, by needle injection into healthy myocardium adjacent to a cryo-injury on the anterior left ventricular wall in athymic nude rats (N=4 rats in each group). An additional control group received injection of media alone with no cells, as a sham operative control. All rats survived the burn protocol and cell engraftment, and the inventors interrogated cardiac function by serial echocardiography on days 3, 7, 14 and 21 after cryoinjury and cell engraftment, and compared these results to baseline echocardiograms for each rat (FIG. 10A). At the time of study and data analysis, the echocardiographers were blinded as to whether the rat was a control or an experimental subject. At three days, after successful recovery from surgery, the standardized cryoinjury had caused a ~15-20% decrease in overall LV fractional shortening, and this result was highly reproducible from animal-to-animal. By 21 days, rats that had received myocardial injection of media alone showed no appreciable improvement in LV function (FIG. 5B). Moreover, rats that had received vehicle treated cells showed only modest improvement in LV function (FIG. 5B). In striking contrast, rats that had received Shz-3 enhanced cells demonstrated a significant improvement in LV function at 7 days, and returning to normal pre-injury contractile function levels by day 21 (FIG. 5B). The difference in contractile function between rats that had received Shz-3 or vehicle treated cells was highly significant on day 7 post injury (P=0.00183) and remained highly significant on day 14 (P=0.00023), and day 21 (P=0.00024) (FIG. 5B). Thus, Shz drug enhanced cells conferred a significant improvement in cardiac function after cryo-injury but control/vehicle treated cells did not.

To show that the improvement in LV function following engraftment of drug treated human cells was associated with survival of human xenograft cells in the rat myocardium, the inventors performed immunostaining of the chimeric myocardium. Indeed, colonies of Shz-3 treated human cells, whose nuclei were clearly marked by DAPI staining, could be definitively identified using a human-specific cTnI mAb in the needle track and invading adjacent myocardium (FIG. 5C, right panel). For control, serial tissue sections were stained with a second mAb against α-actinin, which exclusively identified the host cardiomyocytes (FIG. 5C, left panel). Collectively, the mutually exclusive species-specific staining pattern obtained with these two muscle mAbs (cTnI-→human and α-actinin-→rat) strongly argues against fusion between human cells and host rat myocardium as a predominant mechanism, if it occurs at all in this system (FIG. 5C).

To provide additional molecular evidence that Shz small-molecule treated human cells were still viable and expressing human cardiac genes in chimeric myocardium, the inventors assayed for rare human-specific transcripts (of highly conserved cardiac mRNAs) amidst abundant rat cardiomyocyte transcripts (FIG. 5D; FIG. 10B). First, the inventors did high stringency RT-PCR using conditions optimized to preferentially amplify the human versus rat Nkx2.5 or cTnI cDNAs (FIG. 5D). For both Nkx2.5 and cTnI, a PCR band was more abundant in chimeric myocardium from rats that had been injected with Shz-3 treated cells than their counterparts that had been injected with cells treated with vehicle alone (FIG. 5D). The inventors further cloned and sequenced RT-PCR products generated from the chimeric myocardium of rats injected with Shz small-molecule treated human M-PBMCs and identified human cDNA sequences from this chimeric tissue (FIG. 10B), providing strong evidence that human cells were viable and synthesizing cardiac mRNAs, one month after engraftment into the injured rat heart. Thus, the cell-mediated functional recovery enhanced by drug was associated with increased expression of human cardiac mRNAs by xenograft M-PBMCs in the injured rat heart.

Example 3

Discussion

The inventors report a successful chemical library screen for chemical activators of the early cardiac genome in pluripotent stem cells and characterize a promising family of small-molecules that can both promote cardiac regenerative therapies and serve as mechanistic tools to gain insight into the biology that underlies cell fate decisions in stem cells. The Shz small-molecules were among the strongest inducers of the Nkx2.5 BAC reporter gene system to emerge from this primary screen of almost 150,000 compounds using genetically engineered P19CL6 pluripotent stem cells. the inventors tested Shz small-molecules in a number of confirmatory stem cell cardiac reporter gene assays, and validated their bioactivity by demonstrating specific induction of cardiac mRNAs and proteins. Most remarkably, Shz small-molecules activated the human cardiac genome in adult M-PBMCs, one of the most clinically viable sources of stem cells for cardiac therapy. Indeed, Shz small-molecules dose-dependently enhanced the growth, differentiation and survival of M-PBMC-derived cells that expressed a subset of cardiac genes. Engraftment of drug-induced human M-PBMCs improved cardiac function in a rat myocardial cryoinjury model significantly better than control M-PBMCs treated with vehicle alone. Thus, from a chemical screen based on one of the earliest genes known to be involved in cardiac fate, the inventors have identified a novel class of small-molecules that can enhance the cardio-regenerative potential of adult human PBMCs, which correlates with the ability of Shz drugs to chemically activate the expression of early cardiac genes.

The inventors' goal of drug discovery in cardiac cell therapy is a small-molecule that can modulate stem cells to induce cardiac fate commitment. To begin to identify these molecules, the inventors designed a chemical screen to recover small-molecules targeting Nkx2.5, a signature gene of the cardiovascular master stem cell (Wu et al., 2006; Moretti et al., 2006; Garry & Olson, 2006). In this regard, the design of this screen was fundamentally different from previous cardiogenic small-molecule screens that targeted the 5' regulatory sequences of two very late/definitive markers of cardiac differentiation, α-myosin heavy chain (Takahashi et al., 2003) or atrial natriuretic factor (Wu et al., 2004), neither of which have known functional roles in assigning stem cells to a cardiac fate, but are rather markers of late cardiogenic differentiation. An additional important distinction of this screen was the use of an artificial chromosome, a chromatin domain encompassing all of the transcriptional and epigenetic regulatory sequences necessary for cardiac-specific expression of the Nkx2.5 gene.

The inventors speculate that the Shz small molecule-induced sarcomeric α-tropomyosin positive P19CL6 cell clusters (FIG. 2F) are colonies of "cardioblasts," committed to the cardiac cell fate yet still highly proliferative. In future studies, the inventors will isolate, subclone and characterize the growth and differentiation properties of these Shz drug-induced cardiac progenitors, and determine the additional chemical signals necessary to drive these precursors towards functional and terminal cardiac differentiation, in vitro and in vivo.

The inventors' finding that Shz small-molecule pre-treated human M-PBMCs successfully engrafted into rat myocardium, remained viable, expressed human specific cardiac markers and conferred improved cardiac function, raises many important questions and possibilities, and could have immediate clinical implications. Future experiments will focus on characterization of the electrical and contractile properties of Shz small-molecule treated human M-PBMC. Additional studies will address the role of Shz small-molecules in recruitment and induction of resident cardiac stem/progenitor cells either by direct intramyocardial administration of the Shz small molecules or by intravenous injection. Preliminary pharmacokinetic studies in mice indicate that high plasma concentrations of Shz-1 can be achieved following single dose intravenous administration, even accumulating in myocardium, and lacking obvious organ system toxicity (data not shown). Thus, as the first agent identified in a small-molecule screen capable of enhancing myocardial regeneration with human M-PBMCs, the Shz class of compounds has significant clinical potential, either for ex vivo pre-treatment of stem cells or systemic administration.

Example 4

Materials and Methods

Cell culture and in vitro differentiation analysis. The hippocampal neural stem/progenitor cells (NPCs) were isolated from adult (8-10 weeks old) female Fisher 344 rats. NPCs were cultured in DMEM:F12 (Omega Scientific) with N2 supplement (Invitrogen) and basic fibroblast growth factor (20 ng/ml FGF-2) (PeproTech). The mouse whole brain neural stem/progenitors (MWB) were derived from adult (8-10 weeks old) C57BL/6 mice. The P19CL6 cells is a sub-line of P19EC cells, originally generated by the late Dr. Habara-Ohkubo, and were grown in MEMα(Invitrogen) containing 10% fetal bovine serum (Omega). For isoxazole experiments, NPCs or MWB neural progenitors were trypsinized and plated into N2 medium (Invitrogen) containing FGF-2 (rat NPCs) or FGF-2/EGF/heparin (MWB) overnight, and switched to fresh N2 medium containing different concentrations of isoxazole (5-20 µM) for 1-4 days. Standard NPC differentiation conditions were used for neurons, oligodendrocytes and astrocytes. To induce neuronal differentiation of P19CL6 cells, 1 µM all-trans retinoic acid (RA) was added to the culture media to form P19CL6 aggregates for 2-4 days, then media was replaced with fresh N2 medium and isoxazole was added for 4 days. In some cultures, BrdU (10 µM, Sigma) was added to label dividing cells, propidium iodide (1 µg/ml, Molecular Probes) or Hoescht 33342 (1 µg/ml, Sigma) were added to label dead or all cells, and Q-VD-OPh (2 µM, Enzyme Systems Products) was used to inhibit apoptosis. For CamK/PKC inhibitor experiments, NPCs were pre-treated with inhibitors (KN93 [1-10 µM], KN92 [1-10 µM] or Gö6976 [5-200 nM]) for 24 hrs, and 20 µM Isx was added for 24 or 48 hrs.

Reporter assay and compound treatment. All reporter gene assays were done in 96-well format, and each data point represents the average of 12 replicates. Reporter genes included NeuroD-, GluR2-, Nkx2.5-, 3XMRE-, NR1-, and pHDAC5:14-3-3-luciferase and each well contained ~25,000 cells in a volume of 100 µl. $5\times10^6$ cells NPCs were transfected with 5 µg DNA by electroporation (Amaxa) and plated in N2/FGF-2 media overnight. Compounds were added the day following transfection and luciferase assays were performed 24 or 48 hrs later. Typical dose of Isx in reporter assays was 20 µM unless noted otherwise. For MEF2C-engrailed experiments, NPCs were co-electroporated with two DNA constructs: 3 µg of MEF2C-engrailed plasmid (CAG-MEF2C-engrailed-IRES-GFP) or GFP control plasmid (CAG-GFP-IRES-GFP) plus 2 µg of various luciferase reporter plasmids. GFP expression was visualized 48 hours after electroporation to confirm >50% transduction efficiency before adding compounds and luciferase assays were performed an additional 24 hours later.

Immunocytochemistry and in vitro quantification. Cells were fixed with 4% paraformaldehyde, followed by immunocytochemical staining Labeled cells were visualized using a Nikon TE2000-U inverted microscope (Nikon, Inc.) and a CoolSnap digital camera (Photometrics, Inc.). Quantification of cell phenotypes was done by sampling 6-8 random fields in each well and counting a total of 250-500 cells at 20× magnification. 4',6-diamidino-2-phenylindole (DAPI) was used to identify individual cells. For quantification of live/dead cells, images were taken of cultures live-stained with propidum iodide and Hoescht 33342 at 20× magnification, and 500-1000 cells were counted by sampling 6-8 random fields in each well. The following primary antibodies were used: rabbit anti-Tuj1 (1:7500; Covance), mouse anti-Map2ab (1:250; Sigma);

guinea pig anti-GFAP (1:2500; Advanced Immunochemical, Inc.); rat anti-BrdU (1:400; Accurate). Secondary antibodies were all from Jackson ImmunoResearch and used at 1:250 dilution. The detection of BrdU in cultured cells required treatment in 2NHCL at 37° C. for 30 mins.

RT-PCR and protein blotting. Total RNA was isolated by Trizol reagent (Invitrogen) and RT-PCR performed. Primer sequences are available upon request. For protein blotting, whole cell lysates were prepared from NPCs cultured in undifferentiated conditions (FGF-2 or DMSO vehicle control) or from differentiating conditions (Isx). For protein blots, whole cell lysates were prepared from NPCs using RIPA buffer (Tris-Hcl, 50 mM, pH 7.4; NP-40, 1%; Na-deoxycholate, 0.25%; NaCl, 150 mM; EDTA, 1 mM; PMSF, 1 mM; aprotinin, leupeptin, pepstatin, 1 µg/ml; $Na_3VO4$, 1 mM; NaF, 1 mM). Protein concentration in centrifugation-clarified cell lysates were measured by the BCA Protein Assay Kit (Pierce) and equal amounts of protein were separated on a 4-12% SDS-PAGE and transferred to Hybond PVDF (Amersham Biosciences). Protein blots were done using the NuPage gel and transfer system with 4-20% Tris-Bis gels (Invitrogen). Primary Abs for protein blotting included: rabbit anti-Tuj1 (1:1000; Covance), mouse anti-Map2ab (1:100; Sigma); goat anti-doublecortin (1:100; Chemicon), mouse anti-GAPDH (1:5000; Chemicon), rabbit anti-MEF2C (1:500; Santa Cruz); rabbit anti GluR2/3 (1:250; Chemicon); rabbit anti-phosphorylated HDAC5 (1:500; gift from T. McKinsey); rabbit anti-NRSF (1:200; Upstate); rabbit anti-CREB (1:100; Cell Signaling); rabbit anti-NR1 (1:500; Chemicon); rabbit anti-phosphorylated CamK (1:200; Cell Signaling). Immunoreactive bands were visualized using HRP- or AP-conjugated secondary antibodies, followed by ECL (Amersham Biosciences) or BCIP/NBT detection (KPL, Gaithersburg, Md.).

Adenoviral infection. NPCs or Cos cells were infected with adenovirus at a multiplicity of infection of 10 particles/cell for 24 or 48 hrs. For reporter gene experiments, NPCs were electroporated with luciferase constructs and mixed with virus before plating in N2 medium with FGF-2. After 48 hrs, cells were replaced with N2 medium containing Isx compounds and cultured for an additional 24 hours. To visualize GFP on glass slides, NPCs were plated in N2 medium with FGF-2 and infected with adenovirus for 48 hrs, then media was replaced with N2 medium plus vehicle or Isx, and cultured for an additional 24 hrs. In some experiments, Cos cells were plated in IMDM medium (Invitrogen) containing 10% FBS and infected with adenovirus, and cultured for an additional 24 hrs.

$Ca^{2+}$ imaging. NPCs were loaded with 5 µM Fura2-AM (Molecular Probes) in artificial cerebrospinal fluid (ACSF) (140 mM NaCl, 5 mM KCL, 1 mM MgCL2, 2 mM $CaCl_2$, 10 mM HEPES (pH 7.3) for 45 mins at 37° C. For imaging experiments the coverslips were mounted onto a recording/perfusion chamber (RC-26G, Warner Instrument) maintained at 37° C. (PH1, Warner Instrument) positioned on the movable stage of an Olympus IX-70 inverted microscope, and perfused with ACSF media by gravity flow. Compounds (Isx 20 µM) or DMSO (vol/vol) were added and recording was started (time 0). For Isx plus inhibitor experiments, NPCs were pre-treated with a "cocktail" inhibitor (5 µM each of AP5/CNQX/Nifedipine) or 2 μM MK801 for 5 mins before isoxazole treatment. Cells were intermittently excited by 340 nm and 380 nm UV light (DeltaRAM illuminator, PTI) using a Fura-2 dichroic filter cube (Chroma Technologies) and a 60×UV-grade oil-immersed objective (Olympus) and collected at 10 sec intervals and shown as 340/380 ratios at timepoints as indicated.

Statistical analysis. Results were analyzed for statistical significance using two-tailed Student's t test and all error bars are expressed as standard deviations. Values of $p<0.05$ were considered significant.

Example 5

Results

Isoxazole-induced neuronal differentiation in adult hippocampal neural stem/progenitor cells. The inventors screened a pre-selected collection of synthetic small organic molecules (Sadek et al., manuscript submitted) for compounds that could chemically activate the neuronal gene program in P19 embryonal carcinoma cells using semi high-throughput luciferase assays as described in Examples 1 and 2. Among the candidate small molecules capable of inducing our neuronal reporter gene, neuroD, a key bHLH transcription factor involved in neuronal cell fate determination and differentiation (REF), the inventors identified several compounds belonging to the structural class of 3,5-disubstituted isoxazole (Isx), molecules not previously associated with biological activity. Isx treatment induced at least a 8-fold increase in both NeuroD and GluR2 luciferase reporters, compared to a modest 2-fold increase in reporter activity with the pleiotropic chemical inducers retinoic acid and forskolin, until now gold standards for neuronal induction (FIG. 15A-B).

Isoxazoles at 20 μM concentration were effective inducers of neuronal differentiation in NPCs within 4 days, inducing morphological changes such as cell clustering, cell flattening and extension of processes, and induction of neuronal lineage-specific markers like TuJ1 and Map2ab, when compared to control cells treated with vehicle alone. Morphological changes became evident within hours of drug exposure, while an increase in the percentage of Tuj1+ neurons dramatically increased between 1 and 4 days compared to vehicle alone. NPCs that differentiated into definitive neuronal cells were scored on the basis of morphological criteria (elaboration of neuronal processes), as well as immunoreactivity with various neuronal markers (e.g., Tuj1) (FIGS. 15C-F). Isx treatment could also efficiently convert undifferentiated pluripotent embryonic stem cells (P19 embryonal carcinoma) as well as adult mouse whole brain (MWB) neural progenitors, suggesting that neuronal differentiation by isoxazoles is not just specific to adult rat hippocampal NPCs.

Figure 15G:
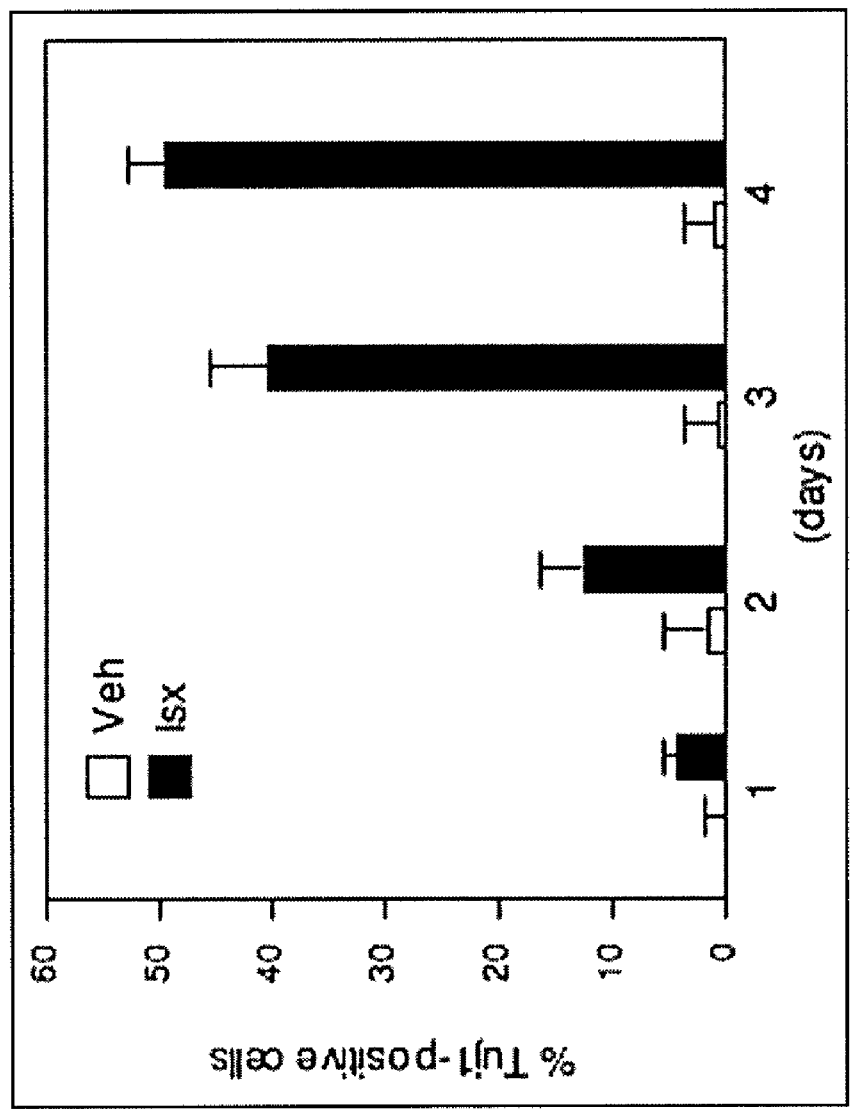

In addition to promoting neuronal differentiation, Isx dominantly suppressed glial differentiation in NPCs, even in the presence of strong gliogenic signals such as LIF and BMP2.50 ng/ml LIF and 50 ng/ml BMP2 normally induced the differentiation of NPCs in 4-day cultures into Tuj1+ neurons and GFAP+ astrocytes, however treatment of cells with Isx completely suppressed astrocyte differentiation, and instead promoted neuronal differentiation (FIG. 15G). Moreover, Isx treatment also suppressed IGF-I induced oligodendrocyte differentiation. Taken together, these data suggest that Isx is a potent activator of the neurogenic lineage in stem cells.

Figure 15H:
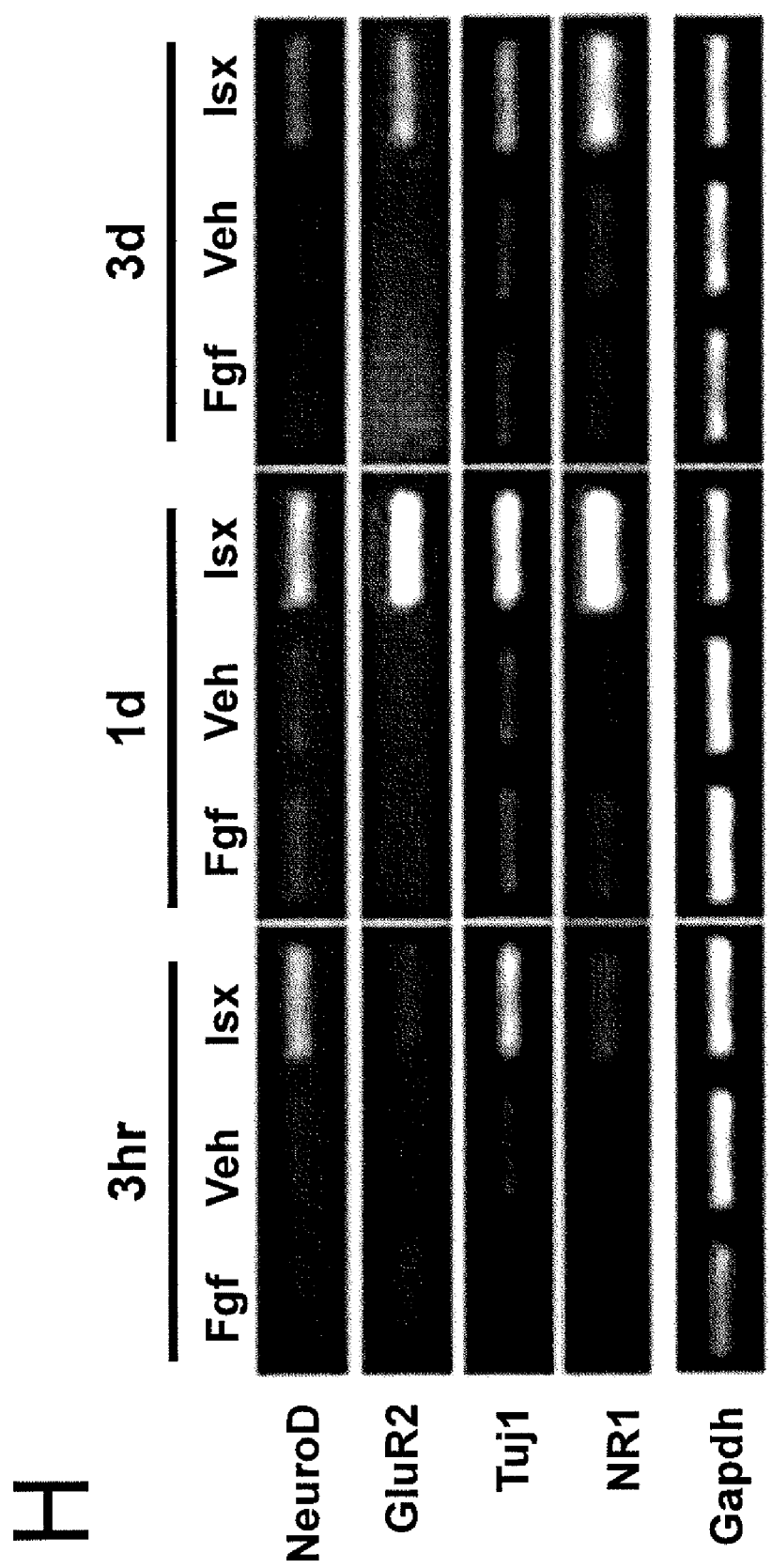
Figure 15I:
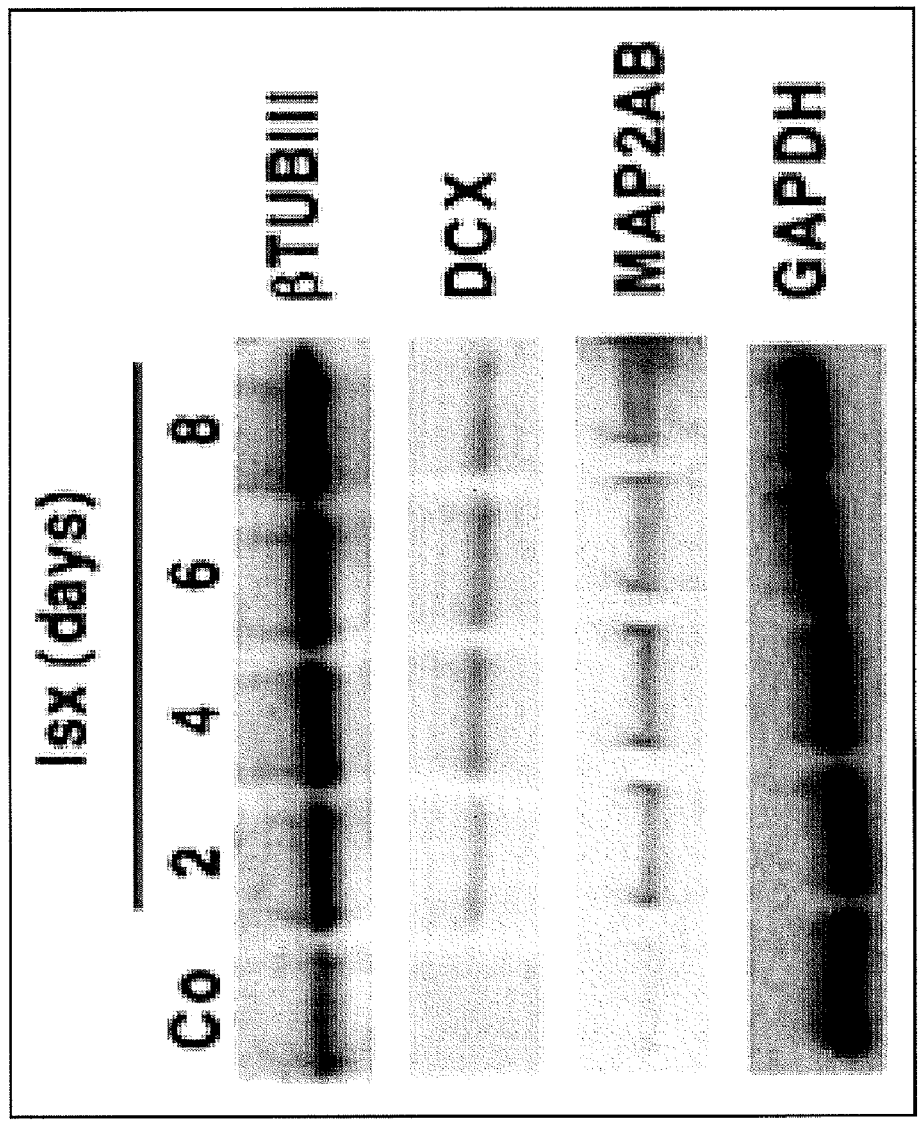

Using semi-quantitative reverse transcriptase polymerase chain reaction (RT-PCR), the inventors observed increased neuroD, GluR2, β III-tubulin (Tuj1) and NMDA receptor subunit 1 (NR1) mRNA levels, all genes associated with neuronal commitment, differentiation, and/or maturation (FIG. 15H). Indeed, by mRNA, significant changes in gene expression were evident even after 3 hrs of Isx treatment. Notably, many of these neuronal transcripts tested were highest at 1 day, with lower levels by 4 days, suggesting a temporal regulation of neuronal gene expression by Isx. Gapdh levels did not change with Isx treatment and was used as an internal control (FIG. 15H). Furthermore, the inventors never observed the expression of astrocytic and oligodendrocytic markers in the presence of Isx Isx treatment also induced a gradual increase in the level of neuronal protein expression over time, including βTUBIII and Doublecortin (DCX), which are expressed in immature neurons, as well as microtubule associated protein-2AB (Map2AB), which is expressed in more mature neurons (FIG. 15I). Neuronal protein expression was normalized for total protein concentration as well as to GAPDH. These data strongly support that Isx small molecules acts specifically and dominantly to induce neuronal differentiation and suppress glial differentiation.

Isoxazole-induced neuronal differentiation is due to instructive effects and a subsequent proliferation of committed neuroblasts. Although these results established Isx as an inducer of neuronal differentiation of multipotent NPCs, it is important to assess the instructive versus selective effects of Isx. Stem cells can self-renew to give rise to more stem cells, or commit to a particular lineage and differentiate into cells of a mature phenotype, or die, and Isx may mediate a net increase in neuronal cells by acting at multiple levels. The results suggest a biphasic response of NPCs to Isx treatment: (1) the initial cell death associated with Isx-treatment and FGF-2 withdrawal does not distinguish between neuronal and non-neuronal cells within the first two days, and (2) continued Isx treatment might additionally promote the survival of differentiated neurons, in addition to inducing neuronal cell fate choice.

Next, the inventors determined whether proliferation of progenitors might contribute to the Isx-mediated neuronal differentiation. There was a gradual decrease in dividing cells in vehicle-treated cultures over time, most likely due to FGF-2 withdrawal. In contrast, Isx-treatment exhibited an initial drop in BrdU incorporation compared to vehicle controls (~10% compared to ~40% on the first day), suggesting that Isx does not have a major proliferation effect on NPCs. Interestingly, Isx-treated progenitor cells did show a slight increase in BrdU cells between 1 and 2 days, suggesting that there might be a secondary effect of Isx on NPC proliferation.

To determine if Isx has an effect on cells already committed to the neuronal lineage but still retained the ability to divide (neuroblasts), the inventors assessed the proliferation of Tuj1+ cells with Isx treatment. Indeed, an increase in the number of Tuj1+ cells that were also BrdU+ with Isx during the 4-day period was observed. Vehicle treated cultures did not produce BrdU+ cells that were also Tuj1+, while a significant number of Tuj1+ cells in Isx-treated cultures were BrdU+, suggesting that Isx-mediated neuronal differentiation is due to instructive effects on neuronal cell fate, as well as a subsequent proliferation of committed neuroblasts.

Isoxazole treatment triggers the release of intracellular $Ca^{2+}$ in NPCs. At the core of the 3,5 disubstituted Isx small molecule is a chemical structure shared by molecules known to affect neurotransmission, such as α-amino-3-hydroxy-5-methyl isoxazole-4-proprionic acid (AMPA) and 5-aminomethyl-3-hydroxy-isoxazole (Muscimol). Treatment of NPCs with 25 μM AMPA or 50 μM Muscimol failed to induce morphologic neuronal differentiation, although there was some neuronal gene activation as evidenced by an increase in neuroD-luciferase activity and GluR2/3 protein expression with 15 or 50 μM Muscimol, respectively, suggesting that there may be a degree of specificity of Isx neurotransmitter-like effects in stem/progenitor cells. Based on studies by others, the inventors hypothesized that Isx might also regulate

[Ca$^{2+}$]$_i$ levels in NPCs. The relatively slow kinetics of [Ca$^{2+}$]$_i$ release after Isx treatment, compared to other strong inducers of [Ca$^{2+}$]$_i$ such as ionomycin, was reminiscent of transcription factor activation consistent with "excitation" of NPCs leading to neuronal gene expression and neurogenesis. Indeed, the inventors did observe a small but significant decrease in NeuroD-luciferase in NPCs treated for 24 hrs with Isx plus cocktail inhibitor (P=0.0002) as well as Isx plus MK801 (P=0.0003), suggesting that the Isx-mediated Ca$^{2+}$ release involved the concerted actions of high-voltage Ca$^{2+}$ channels as well as NMDA receptors.

Isx-mediated neuronal differentiation is coupled to MEF2 activation in NPCs. A number of transcription factors, including CREB, NFAT, and MEF2 are activated by a slow and sustained release of intracellular Ca$^{2+}$ in neuronal cells. Thus, the inventors next assessed Isx effects on a set of Ca$^{2+}$-activated reporter transgenes. NFAT and MCIP are two cellular transcription factors regulated by the Ca$^{2+}$-activated phosphatase, calcineurin. To monitor NFAT and MCIP activities, they used luciferase reporters bearing the NFAT and MCIP regulatory regions (NFAT- and MCIP-luc) (REF). They observed a strong induction of both NFAT- and MCIP-luc with 24 hours of Isx treatment. The induction of NFAT and MCIP by Isx was dependent on calcineurin activity, since treatment of NPCs with two calcineurin inhibitors, FK506 (1.25-20 µM) and CsA (1.25-20 µM), blocked Isx activation in a dose-dependent manner.

Isoxazoles were originally identified in a cardiogenic small molecule screen of pluripotent embryonal carcinoma cells (P19CL6), based on the activation of the NK-2 class homeodomain protein (Nkx2.5). In light of Nkx2.5 role in neuronal cell differentiation, the inventors confirmed that Isx treatment triggered the activation of a rat Nkx2.5-luciferase transgene in NPCs. Recently, it was suggested that Nkx2.5 and myocyte enhancer factor-2C (MEF2C) could reciprocally regulate each other's expression and induce cardiogenesis in P19EC cells, as well as neurogenesis in P19 cells. Moreover, Ca$^{2+}$ signaling strongly influences the activity of MEF2 proteins through voltage-sensitive Ca$^{2+}$ channels triggering phosphorylation and calcineurin-mediated dephosphorylation leading to MEF2-dependent transcription, and calcineurin has recently been shown to control neuronal synapse formation via a MEF2-regulated transcriptional mechanism. The inventors thus examined whether there was a connection between Isx-mediated neuronal differentiation and MEF2. Indeed, Isx treatment induced a MEF2 promter as compared to vehicle alone, and was blocked by calcineurin inhibitors FK506 and CsA in a dose-dependent manner similar to what was seen with NFAT and MCIP.

To further examine the role of MEF2 proteins in NPCs, the inventors determined the levels of MEF2 isoforms in NPCs treated with Isx for 2- and 4-days, compared to vehicle treatment. There are four MEF2 isoforms in all, with MEF2A, 2C, and 2D having the highest expression in the adult brain. MEF2C mRNA levels, and to a lesser extent MEF2A, appeared to be up-regulated with Isx treatment, suggesting a possible role of MEF2A and 2C in neuronal lineage progression of NPCs. Despite the increase in mRNA levels, the inventors did not observe an induction of MEF2A or 2C protein after Isx treatment up to 64 hrs, which is the timeframe that neuronal differentiation is occurring as evident the expression of two mature neuronal markers Map2AB and GluR2/3.

MEF2 activation is due to phosphorylation and export of HDAC5. Post-transcriptional/translational regulation of MEF2 is commonly mediated by CaMK-mediated phosphorylation, calcineurin-dependent dephosphorylation, calreticulin-dependent translocation into the nucleus, and/or through its interaction with class II histone deacetylases (HDACs). Unlike MEF2A and 2C mRNA levels that were induced with Isx treatment, the activation of MEF2 by isoxazoles did not appear to be regulated at the level of phosphorylation or dephosphorylation or translocation since MEF2A and MEF2C protein levels are relatively unchanged between nuclear or cytoplasmic fractions with drug treatment. The inventors thus considered the possibility that MEF2 activity was controlled by epigenetic mechanisms, held in a repressed state in NPCs through its interaction with class II HDACs.

There are three classes of histone deacetylases (HDACs) expressed in vertebrates. Class I HDACs are ubiquitously expressed, whereas class II HDACs have tissue-specific patterns of expression with highest levels in brain, heart and skeletal muscle. Class III HDACs are related to the Sir2 family proteins in yeast. Importantly, recent findings show that class IIa HDACs (HDAC-4, -5, -7, and -9) act as signal-responsive repressors of cardiac hypertrophy and that hypertrophic stimulus induced phosphorylation of class II HDACs in a Ca$^{2+}$/calmodulin kinase (CaMK) dependent fashion that causes export from the nucleus resulting in derepression of target gene expression. To examine the subcellular distribution of HDAC5 in NPCs, the inventors took advantage of a phospho-specific HDAC5 antibody. NPCs treated with vehicle or Isx for 1 day have similar levels of phos-HDAC5 in the nucleus, whereas higher levels of phos-HDAC5 in the cytoplasm are observed with Isx treatment while total HDAC5 levels are unchanged. Next, the inventors observed that Isx treatment slightly increased cytoplasmic accumulation of HDAC4, whereas phospho-HDAC4 (using an antibody that cross-reacts with phospho XX of HDAC4) did not appear to change or increase with drug treatment and remained cytoplasmic, suggesting that phosphorylation of HDAC5 compared to HDAC4 was more sensitive to Isx effects.

In addition to MEF2 proteins, another key transcription factor that is activated by Ca$^{2+}$-dependent signaling in neuronal cells is the nuclear CREB transcription factor, which remained unchanged between vehicle and Isx-treated cells, and served as normalization controls for nuclear extracts. GAPDH was used as a loading control for cytoplasmic extracts.

To visualize the subcellular distribution of HDAC5, NPCs were infected with an adenovirus expressing GFP-HDAC5 (AdGFP-HDAC5) and stimulated with vehicle or Isx for 1 day. In unstimulated cells, 80-90% of the cells contained GFP-HDAC5 in both nuclear and cytoplasmic compartments, reflecting a basal level of nuclear export consistent with what is observed in other cell types. In contrast, Isx triggered nuclear export of HDAC5 (60% cytoplasmic localization versus 35% both nuclear and cytoplasmic). Phosphorylation of serines 259 and 498 in HDAC5 creates docking sites for 14-3-3 chaperone proteins, which shuttle HDAC5 to the cytoplasm. Conversely, HDAC5 S259/498A (S-A mutant) was found mostly in the nuclear compartment regardless of Isx treatment. To further confirm the subcellular distribution of phospho-HDAC5, NPCs were co-infected with adenovirus expressing HDAC5-Flag and CMV-GFP (to monitor transgene expression in live cells). NPC lysates were immunoprecipitated with a Flag antibody and protein blotted with phospho-HDAC5 and Flag antibody. Indeed the majority of overexpressed Flag-HDAC5 was found in the cytoplasmic fraction after a 2-day Isx treatment, when probed with both the phospho-HDAC5 and Flag antibodies. Total lysates was also immunoblotted with CREB and GFP antibodies to verify the separation of nuclear and cytoplasmic fractions. Finally, to determine whether Isx treatment could induce hyperphosphorylation of HDAC5 in a different cell type, the inventors also found a significant increase in the percentage of Cos cells that exhibited cytoplasmic localization of HDAC5 after drug treatment (from 80.9% Nuc and 13.6% Cyto in vehicle-treated cells to 39.5% Nuc and 46.2% Cyto in Isx-treated cells).

The inventors next directly examined HDAC5 and MEF2 effects on an endogenous MEF2 target gene, NR1, since the inventors did observe an induction of NR1 mRNA with Isx treatment. Indeed an NR1 promoter luciferase construct that contains a functional MEF2-binding site (TTATTTATTTAG (SEQ ID NO:1), −805 to −796) was induced with Isx treatment in a dose-dependent manner. Adenovirus over-expression of HDAC5 suppressed NR1-luciferase activity by at least two-fold compared to infection of a control GFP adenovirus (AdCMV-GFP), in both vehicle- and Isx-treated NPCs. The HDAC5 S-A mutant also suppressed NR1 activity in vehicle- and Isx-treated NPCs. Similar results were seen with an additional MEF2 reporter 3XMRE-luc (data not shown). NPCs were infected with a control GFP adenovirus at equivalent titers to the HDAC5-GFP WT and S-A adenoviruses to confirm a transduction efficiency of nearly 80-90%. These data suggest Isx de-repression/activation of MEF2 in NPCs is associated with class II HDAC, such as HDAC5, transcriptional regulation of neuronal target genes.

To further confirm this, the inventors co-transfected NPCs with a construct encoding a repressor form of MEF2C in NPCs, where the repressor domain of engrailed is fused to MEF2C(CAG-MEF2C-ENG), there was significantly less activation of NR1-luciferase in vehicle-treated cultures compared to over-expression of a CAG-GFP control plasmid. More interestingly, this was sufficient to block Isx-activation of NR1-luciferase. In addition, the inventors measured the neuronal reporter gene NeuroD-luciferase. As with NR1-luciferase, there was significantly less NeuroD activity in both vehicle- and Isx-treated NPCs when HDAC5 (WT), HDAC5 (S-A), or the dominant repressor MEF2C-eng was over-expressed, compared to NPCs that expressed a control GFP plasmid. Taken together, these results suggest that the initial up-regulation of NR1 and NeuroD, and potentially other $Ca^{2+}$-activated neuronal genes after Isx treatment is coupled to MEF2 activation in NPCs.

Isx triggered HDAC5 export and neuronal differentiation is CamK-dependent. As mentioned previously, Class II HDACs are considered signal-responsive repressors during cardiac hypertrophy and nucleocytoplasmic shuttling of HDACs enables MEF2 to associate with HATs. Shuttling of class II HDACs is dependent on phosphorylation of two serine-containing motifs found at their N-termini, when phosphorylated, these motifs are associated with 14-3-3 that masks a nuclear localization sequence. The kinase(s) that phosphorylate class II HDACs and transmit various extracellular signals down to the genome have been mainly attributed to CaM kinases (CaMK) and protein kinase D (PKD), which is phosphorylated and activated by protein kinase C (PKC). To further define the signaling pathways leading to phosphorylation and nuclear export of HDAC5, the inventors tested inhibitors of CaMK and PKC for their abilities to block Isx-induced neuronal differentiation. A specific inhibitor of CaMK (KN93) was extremely effective in blocking Isx-mediated reporter gene expression (3XMRE- and NeuroD-luciferase). In contrast, Gö6976, a specific inhibitor of the $Ca^{2+}$-dependent PKC isozymes did not significantly affect Isx-induced reporter gene expression. Most importantly, KN93 blocked HDAC5 phosphorylation in Isx-treated NPCs, while Gö6976 did not. Autophosphorylation of CaMK is usually required for maximal activity and results in the formation of $Ca^{2+}$-independent enzymes that is usually associated with its ability to respond to different frequencies of $Ca^{2+}$ spikes, which is critical in neuronal cells for learning and memory processes.

* * * * * * * * *

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

X. References

The following references, to the extent that they provide exemplary procedural or other details supplementary to those set forth herein, are specifically incorporated herein by reference.

U.S. Pat. No. 3,817,837
U.S. Pat. No. 3,826,364
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,284,412
U.S. Pat. No. 4,366,241
U.S. Pat. No. 4,472,509
U.S. Pat. No. 4,498,766
U.S. Pat. No. 4,661,913
U.S. Pat. No. 4,680,338
U.S. Pat. No. 4,714,682
U.S. Pat. No. 4,767,206
U.S. Pat. No. 4,774,189
U.S. Pat. No. 4,857,451
U.S. Pat. No. 4,938,948
U.S. Pat. No. 4,989,977
U.S. Pat. No. 5,021,236
U.S. Pat. No. 5,141,648
U.S. Pat. No. 5,160,974
U.S. Pat. No. 5,196,066
U.S. Pat. No. 5,478,722
U.S. Pat. No. 5,563,250
U.S. Pat. No. 5,856,456
U.S. Pat. No. 5,880,270
U.S. Publ. Appl. No. 2005/0277162
Abeyta et al., *Hum. Mol. Genet.*, 13(6):601-608, 2004.
Akashi et al., *J. Exp. Med.*, 198:1035-1042, 2003.
Akashi et al., *Nature*, 404:193-197, 2000.
Al-Hajj et al., *Proc. Natl. Acad. Sci. USA*, 100:3983-3988, 2003.
Antibodies: A Laboratory Manual, Cold Spring Harbor Laboratory, 1988.
Arbibe et al., *Nat. Immunol.*, 1:533-540, 2000.
Assmus et al., *Circ Res* 100, 1234-1241, 2007.
Assmus et al., *NEJM* 355, 1222-1232, 2006.
Atherton et al., *Biol. of Reproduction*, 32:155-171, 1985.
Bauer et al., *Proc Natl. Acad. Sci. USA*, 98:9237-9242, 2001.
Berberian et al., *Science*, 261:1588-1591, 1993.
Bergsagel et al. *Cancer Res.*, 28:2187-2196, 1968.
Beutler, and Rietschel, *Nat. Rev. Immunol.*, 3:169-176, 2003.
Blander and Medzhitov, *Science*, 304:1014-1018, 2004.
Bonnet and Dick, *Nature Med.*, 3, 730-737, 1997.
Bruce et al., *Nature*, 199:79-80, 1963.
Bush et al., *Proc. Natl. Acad. Sci. USA* 101, 2870-2875, 2004.
Campbell, In: *Monoclonal Antibody Technology, Laboratory Techniques in Biochemistry and Molecular Biology*, Burden and Von Knippenberg (Eds.), 13:75-83, Amsterdam, Elseview, 1984.

Cario et al., *J. Immunol.*, 164:966-972, 2000.
Casadevall et al., *Infect. Immun.*, 67:3703-3713, 1999.
Chaudhary et al., *Blood*, 91:4020-4027, 1998.
Chen et al., *Mol BioSystems* 2, 18-24, 2006.
Christensen and Weissman, *Proc. Natl. Acad. Sci. USA*, 98:14541-14546, 2001.
Cleary et al., *Trends Microbiol.*, 4:131-136, 1994.
Creemers et al., *Development* (Cambridge, England) 133, 4245-4256, 2006.
Dell'Era et al., *Circ Res* 93, 414-420, 2003.
Dholakia et al., *J. Biol. Chem.*, 264, 20638-20642, 1989.
Dimmeler et al., *J Clin Invest* 108, 391-397, 2001.
Dimmeler et al., *J Clin Invest* 115, 572-583, 2005.
Ding & Schultz, *NatureBiotech* 22, 833-840, 2004.
Divanovic et al., *Nat. Immunol.*, 6:571-578, 2005.
Dontu et al., *Genes Dev.*, 17:1253-1270, 2003.
Doyle et al., *J. Exp. Med.*, 199:81-90, 2004.
Du et al., *EurCytokine Network*, 11:362-371, 2000.
Ferrandon et al., *Semin. Immunol.*, 16:43-53, 2004.
Gage, *Science*, 287:1433-1438, 2000.
Garry & Olson, *Cell* 127, 1101-1104, 2006.
Gay et al., *Nature*, 351:355-356, 1991.
Gefte et al., *Somatic Cell Genet.*, 3:231-236, 1977.
Geissmann et al., *Immunity*, 19:71-82, 2003.
Gilliet et al., *J. Exp. Med.*, 195:953-958, 2002.
Goding, *In: Monoclonal Antibodies: Principles and Practice*, $2^{nd}$ Ed., Orlando, Fla., Academic Press, 60-61, 65-66, 71-74, 1986.
Gudjonsson et al., *Genes Dev.*, 16:693-706, 2002
Habara-Ohkubo, A., *Cell Struct Funct* 21, 101-110, 1996.
Hayashi et al., *J. Immunol.*, 171:5130-5139, 2003.
Hayashi et al., *Nature*, 420:1099-1103, 2001.
Haynes et al., *J. Virol.*, 75(22):10730-7, 2001.
Hemmi et al., *Nature*, 408:740-744, 2000.
Henderson and Calame, *Annu. Rev. Immunol.*, 16:163-200, 1998.
Heumann et al., *Curr. Opin. Microbiol.*, 1:49-55, 1998.
Hoshino et al., *J. Immunol.*, 162:3749-3752, 1999.
Hsieh et al., *Proc. Natl. Acad. Sci. USA* 101, 16659-16664, 2004.
Igarashi et al., *Immunity*, 17:117-130, 2002.
Iwasaki et al., *Immunity*, 19:451-462, 2003.
Iwasaki-Arai et al., *J. Exp. Med.*, 197:1311-1322, 2003.
Janeway, *Immunol. Today*, 13:11-16, 1992.
Kadowaki et al., *J. Exp. Med.*, 194:863-869, 2001.
Kang et al., *Science*, 240:1034-1036, 1988.
Karsunky et al., *J. Exp. Med.*, 198:305-313, 2003.
Kawada and Ogawa, *Blood*, 98:2008-2013, 2001.
Khatoon et al., *Ann. of Neurology*, 26, 210-219, 1989.
Kimoto et al., *Scand J Infect Dis.* 35(9):568-72, 2003.
King et al., *J. Biol. Chem.*, 269, 10210-10218, 1989.
Kohler and Milstein, *Eur. J. Immunol.*, 6:511-519, 1976.
Kohler and Milstein, *Nature*, 256:495-497, 1975.
Kohler et al., *Methods Enzymol.*, 178:3, 1989.
Kondo et al., *Cell*, 91:661-672, 1997.
Kondo et al., *Nature*, 407:383-386, 2000.
Kondo, et al., *Annu. Rev. Immunol.*, 21:759-806, 2003.
Kouro et al., *Blood*, 100:3672-3680, 2002.
Kreier et al., *In: Infection, Resistance and Immunity*, Harper and Row, New York, 1991.
Kreig, *Biochim. Biophys. Acta*, 1489:107-116, 1999.
Kurt-Jones et al., *Nat. Immunol.*, 1(5):398-401, 2000.
Lagasse et al. *Immunity*, 14:425-436, 2001.
Lenert et al., *Science*, 248:1639-1643, 1990.
Liew et al., *Nat. Rev. Immunol.*, 5:446-458, 2005.
Liu et al., *Proc. Natl. Acad. Sci. USA*, 100:15824-15829, 2003.
Means et al., *Cytokine Growth Factor Rev.*, 11:219-232, 2000.
Means et al., *J. Immunol.*, 163:6748-6755, 1999.
Medzhitov et al., *Mol. Cell*, 2:253-258, 1998.
Medzhitov et al., *Nature*, 388:394-397, 1997.
Miyake et al., *J. Immunol.*, 161:1348-1353, 1998.
Moretti et al., *Cell* 127, 1151-1165, 2006.
Muthuchamy et al., *Mol Cell Biol* 13, 3311-3323, 1993.
Nadal-Ginard & Fuster, *Nat Clin Pract Cardiovasc Med* 4, 1, 2007.
Nagai et al., *J. Immunol.*, 174:7043-7049, 2005.
Nagai et al., *Nat. Immunol.*, 3:667-672, 2002.
Nagai, et al., *Blood*, 99:1699-1705, 2002.
Nygren et al., *Nature Medicine* 10, 494-501, 2004.
Ohashi et al., *J. Immunol.*, 164(2):558-561, 2000.
O'Neill et al., *Immunol. Today*, 21:206-209, 2000.
O'Shannessy et al., *J. Immun. Meth.*, 99, 153-161, 1987.
Oshiumi et al., *Nat. Immunol.*, 4:161-167, 2003.
Owens and Haley, *J. Biol. Chem.*, 259:14843-14848, 1987.
Park et al., *J. Nat. Cancer Inst.*, 46:411-422, 1971.
Perez-Losada and Balmain, *Nat. Rev. Cancer*, 3:434-443, 2003.
Pipes et al., *Genes & Devel* 20, 1545-1556, 2006.
Poltorak et al., *Science*, 282:2085-2088, 1998.
Potter and Haley, *Meth. in Enzymol.*, 91, 613-633, 1983.
Qureshi et al., *J. Exp. Med.*, 189:615-625, 1999.
Ramalho-Santos et al., *Science*, 298:597-600, 2002.
Reya et al., *Nature*, 414:105-111, 2001.
Rosenzweig, A., *NEJM* 355, 1274-1277, 2006.
Rosmarin et al., *Exp. Hematol.*, 33:131-143, 2005.
Sasaki et al., *Proc. Natl. Acad. Sci. USA* 103, 14537-14541, 2006.
Sasso et al., *J. Immunol.*, 142:2778-2783, 1989.
Sato et al., *J. Exp. Med.*, 200:601-611, 2004.
Schachinger et al., *Nat Clin Pract Cardiovasc Med* 3 Suppl 1, S23-28, 2006.
Schachinger et al., *NEJM* 355, 1210-1221, 2006.
Schröder et al., *J Immunol.*, 165:2683-2693, 2000.
Sedger et al., *J. Immunol.*, 169:6193-6201, 2002.
Seeger et al., *Circulation* 111, 1184-1191, 2005.
Seeger et al., *Nature Clin Practice* 4 Suppl 1, S110-113, 2007.
Seong and Matzinger, *Nat. Rev. Immunol.*, 4:469-478, 2004.
Shigematsu et al., *Immunity*, 21:43-53, 2004.
Shimazu et al., *J. Exp. Med.*, 189:1777-1782, 1999.
Shorki et al., *J. Immunol.*, 146:936-940, 1991.
Silvermann et al., *J. Clin. Invest.*, 96:417-426, 1995.
Stein et al., *Cell*, 65:725-735, 1991.
Takahashi et al., *Circulation* 107, 1912-1916, 2003.
Takeda and Akira, *Int. Immunol.*, 17:1-14, 2005.
Takeda et al., *Nat. Immunol.*, 5:987-995, 2004.
Takeuchi et al., *Gene*, 231:59-65, 1999.
Takeuchi et al., *Immunity*, 11:443-451, 1999.
Taylor et al., *Crit. Care Med.*, 29:326-334, 2001.
Tsan et al., *J. Leukoc. Biol.*, 76:514-519, 2004.
Tumbar et al., *Science*, 303(5656):359-363, 2004.
Ueda et al., *J. Exp. Med.*, 199:47-57, 2004.
Ueda et al., *J. Exp. Med.*, 201:1771-1780, 2005.
Viriyakosol et al., *J. Biol. Chem.*, 276:38044-38051, 2001.
Welm et al., *Develop. Biology*, 245:42-56, 2002.
Wodinsky et al., *Cancer Chemother. Rep.*, 51:415-421, 1967.
Wojakowski et al., *Heart (British Cardiac Society)*, 2007.
Wu et al., *Cell* 127, 1137-1150, 2006.
Wu et al., *J Am Chem Soc* 126, 1590-1591, 2004.
Xie et al., *Cell*, 117:663-676, 2004.
Yamaguchi et al., *Circulation* 107, 1322-1328, 2003.
Yamamoto et al., *Science*, 301:640-643, 2003.
Yang et al., *J. Immunol.*, 163:639-643, 1999.
Yoshimura et al., *J. Immunol.*, 163:1-5, 1999.
Zepeda et al., *Somat. Cell Mol. Genet.*, 21:61-73, 1999.
Zhang et al., *J Biomol Screen* 4, 67-73, 1999.
Zhang et al., *Nature*, 425:836-841, 2003.
Zhao et al., *J Comp Neurol* 441, 187-196, 2001.
Zuniga et al., *Nat. Immunol.*, 5:1227-1234, 2004.

What is claimed is:

1. A compound having the formula:

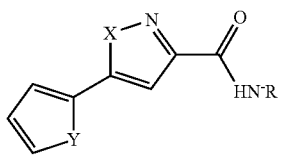

wherein X is NH, Y is O and R is substituted or unsubstituted $C_1$-$C_6$ alkenyl or a substituded or unsubstituted $C_2$-$C_6$ alkynyl.

2. The compound of claim 1, wherein R is a substituted or unsubstituted $C_2$-$C_6$ alkenyl.

3. The compound of claim 1, wherein R is a substituted or unsubstituted $C_2$-$C_6$ alkynyl.

* * * * *

UNITED STATES PATENT AND TRADEMARK OFFICE
CERTIFICATE OF CORRECTION

PATENT NO.        : 8,318,951 B2                                      Page 1 of 1
APPLICATION NO.   : 13/116574
DATED             : November 27, 2012
INVENTOR(S)       : Eric N. Olson et al.

It is certified that error appears in the above-identified patent and that said Letters Patent is hereby corrected as shown below:

In the Claims:

In column 55, claim 1, line 18, delete "having" and insert --of-- therefor.

In column 56, claim 1, line 18, delete "$C_1$-$C_6$" and insert --$C_2$-$C_6$-- therefor.

In column 56, claim 1, line 18, delete "substituded" and insert --substituted-- therefor.

Signed and Sealed this
Twenty-first Day of May, 2013

Teresa Stanek Rea
*Acting Director of the United States Patent and Trademark Office*